(12) United States Patent
Globerman et al.

(10) Patent No.: US 7,621,950 B1
(45) Date of Patent: Nov. 24, 2009

(54) EXPANDABLE INTERVERTEBRAL SPACER

(75) Inventors: Oren Globerman, Kfar-Shmaryahu (IL); Boaz Shenhav, Herzelia (IL); Ronen Shavit, Tel-Aviv (IL)

(73) Assignee: Kyphon SARL, Neuchatel (CH)

( * ) Notice: Subject to any disclaimer, the term of this patent is extended or adjusted under 35 U.S.C. 154(b) by 0 days.

(21) Appl. No.: 09/890,172

(22) PCT Filed: Jan. 27, 2000

(86) PCT No.: PCT/IL00/00058

§ 371 (c)(1),
(2), (4) Date: Jul. 25, 2001

(87) PCT Pub. No.: WO00/44319

PCT Pub. Date: Aug. 3, 2000

(30) Foreign Application Priority Data

Jan. 27, 1999 (IL) .................................. 128261

(51) Int. Cl.
*A61F 2/44* (2006.01)
(52) U.S. Cl. .............. 623/17.11; 623/17.16; 623/23.47; 411/34
(58) Field of Classification Search ................. 623/1.1, 623/1.2, 1.15, 17.11, 17.16, 23.44, 23.45, 623/23.47; 606/237, 594; 411/32, 33, 34, 411/37, 38
See application file for complete search history.

(56) References Cited

U.S. PATENT DOCUMENTS

| | | | |
|---|---|---|---|
| 817,973 A | 4/1906 | Hausmann | |
| 1,175,530 A | 3/1916 | Kirchhoff | |
| 2,067,458 A | 1/1937 | Nichols | |
| 2,918,841 A | 12/1959 | Poupitch | |
| 3,058,413 A | 10/1962 | Cavalieri | |
| 3,063,449 A | 11/1962 | Schultz | |
| 3,075,746 A | 1/1963 | Yablonski et al. | |
| 3,108,593 A * | 10/1963 | Glassman | .................... 606/127 |
| 3,224,744 A | 12/1965 | Broomall | |
| 3,381,566 A | 5/1968 | Passer | |
| 3,426,364 A | 2/1969 | Lumb | |
| 3,789,727 A | 2/1974 | Moran | |
| 3,846,846 A * | 11/1974 | Fischer | .................... 623/23.18 |
| 3,867,728 A * | 2/1975 | Stubstad et al. | .......... 623/17.16 |
| 3,875,595 A | 4/1975 | Froning | |
| 3,896,504 A | 7/1975 | Fischer | |

(Continued)

FOREIGN PATENT DOCUMENTS

AU    724544    11/1996

(Continued)

OTHER PUBLICATIONS

Translation of DE-1810799 patent to Metz, published Jun. 4. 1970.*

(Continued)

*Primary Examiner*—Paul Prebilic

(57) ABSTRACT

An expandable spacer, comprising: an axial tube having a surface, a proximal end and a distal end and a length, wherein, said surface defines a plurality of slits, said plurality of slits defining at least two axially displaced extensions, such that when said tube is axially compressed, said extensions extend out of said surface and define a geometry of an expanded spacer. Preferably the spacer is adapted to be inserted between two spinal vertebrae of a human.

51 Claims, 48 Drawing Sheets

U.S. PATENT DOCUMENTS

| | | | |
|---|---|---|---|
| 3,942,407 A | 3/1976 | Mortensen | |
| 3,976,060 A | 8/1976 | Hildebrandt et al. | |
| 4,011,602 A | 3/1977 | Rybicki et al. | |
| 4,079,917 A | 3/1978 | Popeil | |
| 4,115,346 A | 9/1978 | Gross et al. | |
| 4,170,990 A | 10/1979 | Baumgart et al. | |
| 4,185,072 A | 1/1980 | Puderbaugh et al. | |
| 4,204,531 A | 5/1980 | Aginsky | |
| 4,268,639 A | 5/1981 | Seidel et al. | |
| 4,274,163 A | 6/1981 | Malcom et al. | |
| 4,309,777 A | 1/1982 | Patil | |
| 4,313,434 A | 2/1982 | Segal | |
| 4,346,708 A | 8/1982 | LeVeen et al. | |
| 4,349,921 A | 9/1982 | Kuntz | |
| 4,453,539 A | 6/1984 | Raftopoulos et al. | |
| 4,475,856 A * | 10/1984 | Toomingas | 411/33 |
| 4,494,535 A | 1/1985 | Haig | |
| 4,522,200 A | 6/1985 | Stednitz | |
| D279,499 S | 7/1985 | Case | |
| 4,554,914 A | 11/1985 | Kapp et al. | |
| 4,558,693 A | 12/1985 | Lash et al. | |
| 4,562,598 A | 1/1986 | Kranz | |
| 4,627,434 A | 12/1986 | Murray | |
| 4,632,101 A | 12/1986 | Freedland | |
| 4,636,217 A | 1/1987 | Ogilvie et al. | |
| 4,653,487 A | 3/1987 | Maale | |
| 4,653,489 A | 3/1987 | Tronzo et al. | |
| 4,686,973 A | 8/1987 | Frisch | |
| 4,697,584 A | 10/1987 | Haynes | |
| 4,758,096 A | 7/1988 | Gunnarsson | |
| 4,759,769 A | 7/1988 | Hedman et al. | |
| 4,772,287 A | 9/1988 | Ray et al. | |
| 4,786,184 A | 11/1988 | Berezkina et al. | |
| 4,854,312 A | 8/1989 | Raftopoulos et al. | |
| 4,892,550 A | 1/1990 | Huebsch | |
| 4,904,260 A | 2/1990 | Ray et al. | |
| 4,932,969 A | 6/1990 | Frey et al. | |
| 4,935,029 A | 6/1990 | Matsutani et al. | |
| 4,961,647 A | 10/1990 | Coutts et al. | |
| 4,969,888 A | 11/1990 | Scholten et al. | |
| 4,973,301 A * | 11/1990 | Nissenkorn | 604/8 |
| 4,995,868 A | 2/1991 | Brazier | |
| 5,012,066 A | 4/1991 | Matsutani et al. | |
| 5,018,919 A | 5/1991 | Stephan | |
| 5,059,193 A * | 10/1991 | Kuslich | 606/61 |
| 5,059,199 A | 10/1991 | Okada et al. | |
| 5,074,871 A | 12/1991 | Groshong | |
| 5,078,919 A | 1/1992 | Ashley et al. | |
| 5,102,413 A | 4/1992 | Poddar | |
| 5,108,404 A | 4/1992 | Scholten et al. | |
| 5,112,333 A | 5/1992 | Fixel | |
| 5,116,335 A | 5/1992 | Hannon | |
| 5,122,400 A | 6/1992 | Stewart | |
| 5,123,926 A * | 6/1992 | Pisharodi | 623/17 |
| 5,131,382 A | 7/1992 | Meyer | |
| 5,171,248 A | 12/1992 | Ellis | |
| 5,171,278 A | 12/1992 | Pisharodi | |
| 5,209,753 A | 5/1993 | Biedermann et al. | |
| 5,236,445 A | 8/1993 | Hayhurst et al. | |
| 5,268,001 A | 12/1993 | Nicholson et al. | |
| 5,302,020 A | 4/1994 | Kruse | |
| 5,303,718 A | 4/1994 | Kajicek | |
| 5,333,951 A | 8/1994 | Wakoh | |
| 5,334,184 A | 8/1994 | Bimman | |
| 5,348,391 A | 9/1994 | Murray | |
| 5,356,382 A | 10/1994 | Picha et al. | |
| 5,376,123 A | 12/1994 | Klaue et al. | |
| 5,390,683 A | 2/1995 | Pisharodi | |
| 5,415,474 A | 5/1995 | Nelson et al. | |
| 5,423,850 A | 6/1995 | Berger | |
| 5,445,639 A | 8/1995 | Kuslich et al. | |
| 5,454,365 A * | 10/1995 | Bonutti | 600/204 |
| 5,480,400 A | 1/1996 | Berger | |
| 5,480,403 A | 1/1996 | Lee | |
| 5,494,349 A | 2/1996 | Seddon | |
| 5,501,695 A | 3/1996 | Anspach, Jr. et al. | |
| 5,514,137 A | 5/1996 | Coutts | |
| 5,518,498 A * | 5/1996 | Lindenberg et al. | 600/30 |
| 5,520,690 A | 5/1996 | Errico et al. | |
| 5,522,816 A | 6/1996 | Dinello et al. | |
| 5,522,899 A | 6/1996 | Michelson | |
| 5,534,028 A | 7/1996 | Bao et al. | |
| 5,549,380 A | 8/1996 | Lidgren et al. | |
| 5,549,381 A | 8/1996 | Hays et al. | |
| 5,549,679 A | 8/1996 | Kuslich | |
| 5,554,101 A | 9/1996 | Matula et al. | |
| 5,571,189 A | 11/1996 | Kuslich et al. | |
| 5,578,035 A | 11/1996 | Lin | |
| 5,591,197 A * | 1/1997 | Orth et al. | 623/1.16 |
| 5,601,557 A | 2/1997 | Hayhurst | |
| 5,609,637 A | 3/1997 | Biedermann et al. | |
| 5,637,097 A | 6/1997 | Yoon | |
| 5,645,598 A | 7/1997 | Brosnahan, III | |
| 5,658,310 A | 8/1997 | Berger | |
| 5,667,778 A | 9/1997 | Atala | |
| 5,683,451 A | 11/1997 | Lenker et al. | |
| 5,685,826 A | 11/1997 | Bonutti | |
| 5,690,606 A | 11/1997 | Slotman | |
| 5,693,100 A | 12/1997 | Pisharodi | |
| 5,697,977 A | 12/1997 | Pisharodi | |
| 5,702,448 A * | 12/1997 | Buechel et al. | 623/23.36 |
| 5,704,895 A | 1/1998 | Scott et al. | |
| 5,707,390 A | 1/1998 | Bonutti | |
| 5,720,753 A | 2/1998 | Sander et al. | |
| 5,725,341 A * | 3/1998 | Hofmeister | 411/32 |
| 5,725,529 A | 3/1998 | Nicholson et al. | |
| 5,752,969 A | 5/1998 | Cunci et al. | |
| 5,755,732 A | 5/1998 | Green et al. | |
| 5,759,186 A | 6/1998 | Bachmann et al. | |
| 5,782,713 A | 7/1998 | Yang | |
| 5,782,747 A | 7/1998 | Zimmon | |
| 5,782,830 A | 7/1998 | Farris | |
| 5,782,838 A | 7/1998 | Beyar et al. | |
| 5,782,917 A | 7/1998 | Carn | |
| 5,785,647 A | 7/1998 | Tompkins et al. | |
| 5,800,549 A | 9/1998 | Bao et al. | |
| 5,800,550 A | 9/1998 | Sertich | |
| 5,820,321 A | 10/1998 | Gruber | |
| 5,827,289 A | 10/1998 | Reiley et al. | |
| 5,842,785 A | 12/1998 | Brown et al. | |
| 5,865,802 A | 2/1999 | Yoon et al. | |
| 5,876,457 A * | 3/1999 | Picha et al. | 623/17 |
| 5,882,340 A | 3/1999 | Yoon et al. | |
| 5,893,850 A | 4/1999 | Cachia | |
| 5,911,721 A | 6/1999 | Nicholson et al. | |
| 5,968,044 A | 10/1999 | Nicholson et al. | |
| 5,972,015 A | 10/1999 | Scribner et al. | |
| 6,019,789 A * | 2/2000 | Dinh et al. | 623/1.15 |
| 6,039,761 A | 3/2000 | Li et al. | |
| 6,126,689 A | 10/2000 | Brett | |
| 6,127,597 A | 10/2000 | Beyar et al. | |
| 6,129,763 A * | 10/2000 | Chauvin et al. | 623/17.11 |
| 6,146,401 A | 11/2000 | Yoon et al. | |
| 6,149,651 A * | 11/2000 | Drewry et al. | 606/61 |
| 6,149,664 A | 11/2000 | Kurz | |
| 6,161,955 A | 12/2000 | Rademaker | |
| 6,168,597 B1 | 1/2001 | Biedermann et al. | |
| 6,187,015 B1 | 2/2001 | Brenneman | |
| 6,190,381 B1 | 2/2001 | Olsen et al. | |
| 6,214,016 B1 | 4/2001 | Williams et al. | |
| 6,214,037 B1* | 4/2001 | Mitchell et al. | 623/1.11 |
| 6,217,608 B1* | 4/2001 | Penn et al. | 623/1.16 |
| 6,224,604 B1 | 5/2001 | Suddaby | |
| 6,228,068 B1 | 5/2001 | Yoon | |

| US Patents | | | |
|---|---|---|---|
| 6,228,082 B1 | 5/2001 | Baker et al. | |
| 6,235,043 B1 | 5/2001 | Reiley et al. | |
| 6,241,734 B1 | 6/2001 | Scribner et al. | |
| 6,245,101 B1 * | 6/2001 | Drasler et al. | 623/1.15 |
| 6,248,110 B1 | 6/2001 | Reiley et al. | |
| 6,261,289 B1 | 7/2001 | Levy | |
| 6,264,659 B1 | 7/2001 | Ross et al. | |
| 6,325,812 B1 | 12/2001 | Dubrul et al. | |
| 6,348,055 B1 | 2/2002 | Preissman | |
| 6,350,271 B1 | 2/2002 | Kurz et al. | |
| 6,375,682 B1 | 4/2002 | Fleischmann et al. | |
| 6,383,188 B2 | 5/2002 | Kuslich et al. | |
| 6,383,190 B1 | 5/2002 | Preissman | |
| 6,447,478 B1 * | 9/2002 | Maynard | 604/95.05 |
| 6,500,182 B2 * | 12/2002 | Foster | 606/127 |
| 6,554,833 B2 | 4/2003 | Levy et al. | |
| 6,613,054 B2 | 9/2003 | Scribner et al. | |
| 6,662,969 B2 | 12/2003 | Peeler et al. | |
| 6,719,761 B1 | 4/2004 | Reiley et al. | |
| 6,780,175 B1 * | 8/2004 | Sachdeva et al. | 604/531 |
| 6,875,219 B2 | 4/2005 | Arramon et al. | |
| 6,957,747 B2 | 10/2005 | Peeler et al. | |
| 6,974,247 B2 | 12/2005 | Frei et al. | |
| 6,979,341 B2 | 12/2005 | Scribner et al. | |
| 6,994,465 B2 | 2/2006 | Tague et al. | |
| 7,029,163 B2 | 4/2006 | Barker et al. | |
| 7,097,648 B1 | 8/2006 | Globerman et al. | |
| 2002/0068939 A1 | 6/2002 | Levy et al. | |
| 2002/0068974 A1 | 6/2002 | Kuslich et al. | |
| 2002/0068975 A1 | 6/2002 | Teitelbaum et al. | |
| 2002/0072768 A1 | 6/2002 | Ginn | |
| 2002/0099385 A1 | 7/2002 | Ralph et al. | |
| 2002/0191487 A1 | 12/2002 | Sand | |
| 2003/0040718 A1 | 2/2003 | Kust et al. | |
| 2003/0109883 A1 | 6/2003 | Matsuzaki et al. | |
| 2003/0174576 A1 | 9/2003 | Tague et al. | |
| 2003/0181963 A1 | 9/2003 | Pellegrino et al. | |
| 2004/0054377 A1 | 3/2004 | Foster et al. | |
| 2004/0059283 A1 | 3/2004 | Kirwan et al. | |
| 2004/0167625 A1 | 8/2004 | Beyar et al. | |
| 2004/0208845 A1 | 10/2004 | Michal et al. | |
| 2004/0236313 A1 | 11/2004 | Klein | |
| 2004/0260303 A1 | 12/2004 | Carrison | |
| 2005/0060023 A1 * | 3/2005 | Mitchell et al. | 623/1.15 |
| 2005/0083782 A1 | 4/2005 | Gronau et al. | |
| 2005/0143827 A1 | 6/2005 | Globerman et al. | |
| 2006/0079905 A1 | 4/2006 | Beyar et al. | |
| 2006/0264967 A1 | 11/2006 | Ferreyro et al. | |
| 2006/0271061 A1 | 11/2006 | Beyar et al. | |
| 2007/0027230 A1 | 2/2007 | Beyar et al. | |
| 2007/0032567 A1 | 2/2007 | Beyar et al. | |
| 2007/0282443 A1 | 12/2007 | Globerman et al. | |
| 2009/0171390 A1 * | 7/2009 | Sankaran | 606/246 |

FOREIGN PATENT DOCUMENTS

| | | |
|---|---|---|
| AU | 9865136 | 9/1998 |
| DE | 1 810 799 | 6/1970 |
| DE | 1810799 | 6/1970 |
| DE | 87 16 073 | 3/1988 |
| DE | 4104092 | 8/1991 |
| DE | 196 12 276 | 10/1997 |
| DE | 19612276 | 10/1997 |
| EP | 0 044 877 | 2/1982 |
| EP | 0044877 | 2/1982 |
| EP | 0177781 | 4/1986 |
| EP | 0235905 | 9/1987 |
| EP | 0423916 | 4/1991 |
| EP | 0475077 | 3/1992 |
| EP | 0493789 | 7/1992 |
| EP | 0669100 | 8/1995 |
| EP | 0748615 | 12/1996 |
| EP | 1074231 | 2/2001 |
| EP | 1464292 | 10/2004 |
| EP | 1148850 | 4/2005 |
| EP | 1552797 | 7/2005 |
| EP | 1148851 | 5/2006 |
| FR | 2638972 | 5/1990 |
| FR | 2653006 | 4/1991 |
| FR | 2 674 119 | 9/1992 |
| FR | 2 712 486 | 5/1995 |
| FR | 2712486 | 5/1995 |
| FR | 2 722 679 | 1/1996 |
| FR | 2722679 | 1/1996 |
| GB | 408668 | 4/1934 |
| GB | 2114005 | 8/1983 |
| GB | 2197691 | 5/1988 |
| GB | 2268068 | 1/1994 |
| GB | 2413280 | 10/2005 |
| JP | 54-009110 | 1/1979 |
| JP | 02-122017 | 5/1990 |
| JP | 02-166235 | 6/1990 |
| JP | 8322848 | 12/1996 |
| SU | 662082 | 5/1979 |
| SU | 1011119 | 4/1983 |
| SU | 1049050 | 10/1983 |
| WO | WO 90/00037 | 1/1990 |
| WO | WO 92/14423 | 9/1992 |
| WO | WO 94/12112 | 6/1994 |
| WO | WO 95/13862 | 5/1995 |
| WO | WO 96/11643 | 4/1996 |
| WO | WO 96/19940 | 7/1996 |
| WO | WO 96/32899 | 10/1996 |
| WO | WO 96/37170 | 11/1996 |
| WO | WO 97/18769 | 5/1997 |
| WO | WO 97/28835 | 8/1997 |
| WO | WO 98/28035 | 7/1998 |
| WO | WO 98/38918 | 9/1998 |
| WO | WO 99/18894 | 4/1999 |
| WO | WO 99/39661 | 8/1999 |
| WO | WO 99/52446 | 10/1999 |
| WO | WO 00/06216 | 2/2000 |
| WO | WO 00/44319 | 8/2000 |
| WO | WO 00/44321 | 8/2000 |
| WO | WO 00/44946 | 8/2000 |
| WO | WO 01/08571 | 2/2001 |
| WO | WO 01/54598 | 8/2001 |
| WO | WO 02/02033 | 1/2002 |
| WO | WO 03/061495 | 7/2003 |
| WO | WO 03/101596 | 12/2003 |
| WO | WO 2004/019810 | 3/2004 |
| WO | WO 2004/071543 | 8/2004 |
| WO | WO 2004/075965 | 9/2004 |
| WO | WO 2004/080357 | 9/2004 |
| WO | WO 2004/110292 | 12/2004 |
| WO | WO 2004/110300 | 12/2004 |
| WO | WO 2005/032326 | 4/2005 |
| WO | WO 2005/048867 | 6/2005 |
| WO | WO 2005/051212 | 6/2005 |
| WO | WO 2005/110259 | 11/2005 |
| WO | WO 2006/011152 | 2/2006 |
| WO | WO 2006/039159 | 4/2006 |
| WO | WO 2006/090379 | 8/2006 |
| WO | WO 2007/015202 | 2/2007 |
| WO | WO 2007/036815 | 4/2007 |
| WO | WO 2007/148336 | 12/2007 |
| WO | WO 2008/004229 | 1/2008 |
| WO | WO 2008/032322 | 3/2008 |

OTHER PUBLICATIONS

Narushima, M.; JP 08-322848; Dec. 10, 1996 & Database WPI; Section PQ; Week 199708; Derwent Publications Ltd., London, GB; Class P31, AN 1997-081321; XP002154628.

Weissman, S. L. et al.; "Trochanteric Fractures of the Femur—Treatment with a Strong Nail and Early Weight-bearing;" Nov.-Dec. 1969; pp. 143-150; Clinical Orthopaedics and Related Research; No. 67; XP000964714.
Letter from Mathys & Squire containing Grounds of Opposition dated Jan. 19, 2006.
Letter from Mathys & Squire regarding Opposition dated May 15, 2006.
Edeland "Some Additional Suggestions for An Intervertebral Disc Prothesis", Journal of Biomedical Engineering, XP008072822, 7(1): 57-62, Jan. 1985. Figs.3a-3d.
Communication Pursuant to Article 94(3) EPC Dated Oct. 1, 2008 From the European Patent Office Re.: Application No. 00951812.7.
Communication Pursuant to Article 96(2) EPC Dated Mar. 20, 2007 From the European Patent Office Re.: Application No. 00951812.7.
Communication Pursuant to Article 96(2) EPC Dated Apr. 21, 2006 From the European Patent Office Re.: Application No. 98910912.9.
Communication Pursuant to Article 94(3) EPC Dated Oct. 1, 2008 From the European Patent Office Re.: Application No. 00951812.7.
Communication Pursuant to Article 96(2) EPC Dated Mar. 20, 2007 From the European Patent Office Re.: Application No. 00951812.7.
Communication Pursuant to Article 96(2) EPC Dated Mar. 20, 2007 From the European Patent Office Re.: Application No. 00951812.7.
Communication Pursuant to Article 96(2) EPC Dated Apr. 21, 2006 From the European Patent Office Re.: Application No. 98910912.9.
International Preliminary Examination Report Dated May 7, 2002 From the International Preliminary Examining Report Re.: Application No. PCT/IL00/00471.
International Preliminary Examination Report Dated Apr. 24, 2001 From the International Preliminary Examining Authority Re.: Application No. PCT/IL00/00056.
International Preliminary Report on Patentability Dated Apr. 26, 2007 From the International Bureau of WIPO Re.: Application No. PCT/IL2005/000812.
Invitation to Restrict or to Pay Additional Fees Dated Nov. 14, 2000 From the International Preliminary Examination Authority Re.: Application No. PCT/IL00/00056.
Official Action Dated Dec. 16, 2008 From the US Patent and Trademark Office Re.: U.S. Appl. No. 11/042,546.
Official Action Dated Dec. 22, 2008 From the US Patent and Trademark Office Re.: U.S. Appl. No. 10/182,352.
Official Action Dated Mar. 26, 2004 from the United States Patent and Trademark Office Re.: U.S. Appl. No. 09/890,172.
Official Action Dated Jun. 29, 2006 from the United States Patent and Trademark Office Re.: U.S. Appl. No. 10/182,352.

Written Opinion Dated Jan. 11, 2001 From the International Preliminary Examining Authority Re.: Application No. PCT/IL00/00056.
Written Opinion Dated Dec. 13, 2008 From the International Preliminary Examining Authority Re.: Application No. PCT/IL00/00471.
Baroud et al. "Injection Biomechanics of Bone Cements Used in Vertebroplasty", Biomedical Maerials and Engineering, 00: 1-18, 2004.
Canale et al. "Campbell's Operative Orthopaedics—vol. three—Ninth edition", Mosby: P. 2097,2121, 2184-2185, 2890-2896, 1998. Abstract.
Cole et al. "AIM Titanium Humeral Nail System", Sugical Technique, DePuy Orthopedics, 17 P., 2000.
Heini et al. "The Use of A Side-Opening Injection Cannula in Vertebroplasty", Spine, 27(1): 105-109, 2002.
Hernandez et al. "Influence of Powder Particle Size Distribution on Complex Viscosity and Other Properties of Acrylic Bone Cement for Vetebroplasty and Kyphoplasty", Journal of Biomedical Materials Research, Part. B: Applied Biomaterials, 77B: 98-103, 2006.
Ishikawa et al. "Effects of Neutral Sodium Hydrogen Phosphate on Setting Reaction and Mechanical Strength of Hydroxyapatite Putty", Journal of Biomedical Materials Research, 44: 322-329, 199, 1997 .
Ishikawa et al. "Non-Decay Type Fast-Setting Calcium Phosphate Cement: Hydroxyapatite Putty Containing An Increased Amount of Sodium Alginate", Journal of Biomedical Materials Research, 36: 393-399, 1997.
Krause et al. "The Viscosity of Acrylic Bone Cements", Jouirnal of Biomedical Materials Research, 16: 219-243, 1982.
Lewis "Properties of Acrylic Bone Cement: State of the Art Review", Journal of Biomedical Materials Research Applied Biomaterials, 38(2): 155-182, 1997 p. 158, § Viscosity, Table II.
Lewis "Toward Standardization of Methods of Determination of Fracture Properties of Acrylic Bone Cement and Statistical Analysis of Test Results", Journal of Biomedical Research: Applied Biomaterials, 53(6): 748-768, 2000.
Nussbaum et al. "The Chemistry of Acrylic Bone Cements and Implications for Clinical Use in Image-Guided Therapy", Journal of Vascular and Interventional Radiology, 15: 121-126, 2004.
Steen "Laser Surface Treatment", Laser Material Processing, Springer, 2nd Ed., Chap.6: 218-271, 2003.
Varela et al. "Closed Intramedullary Pinning of Metacarpal and Phalanx Fractures", Orthopedics, 13(2): 213-215, 1990. Abstract.
Weissman et al. "Trochanteric Fractures of the Femur. Treatment With A Strong Nail and Early Weight-Bearing", Clinical Orthopedics and Related Research, 67: 143-150, 1969. Fig.

* cited by examiner

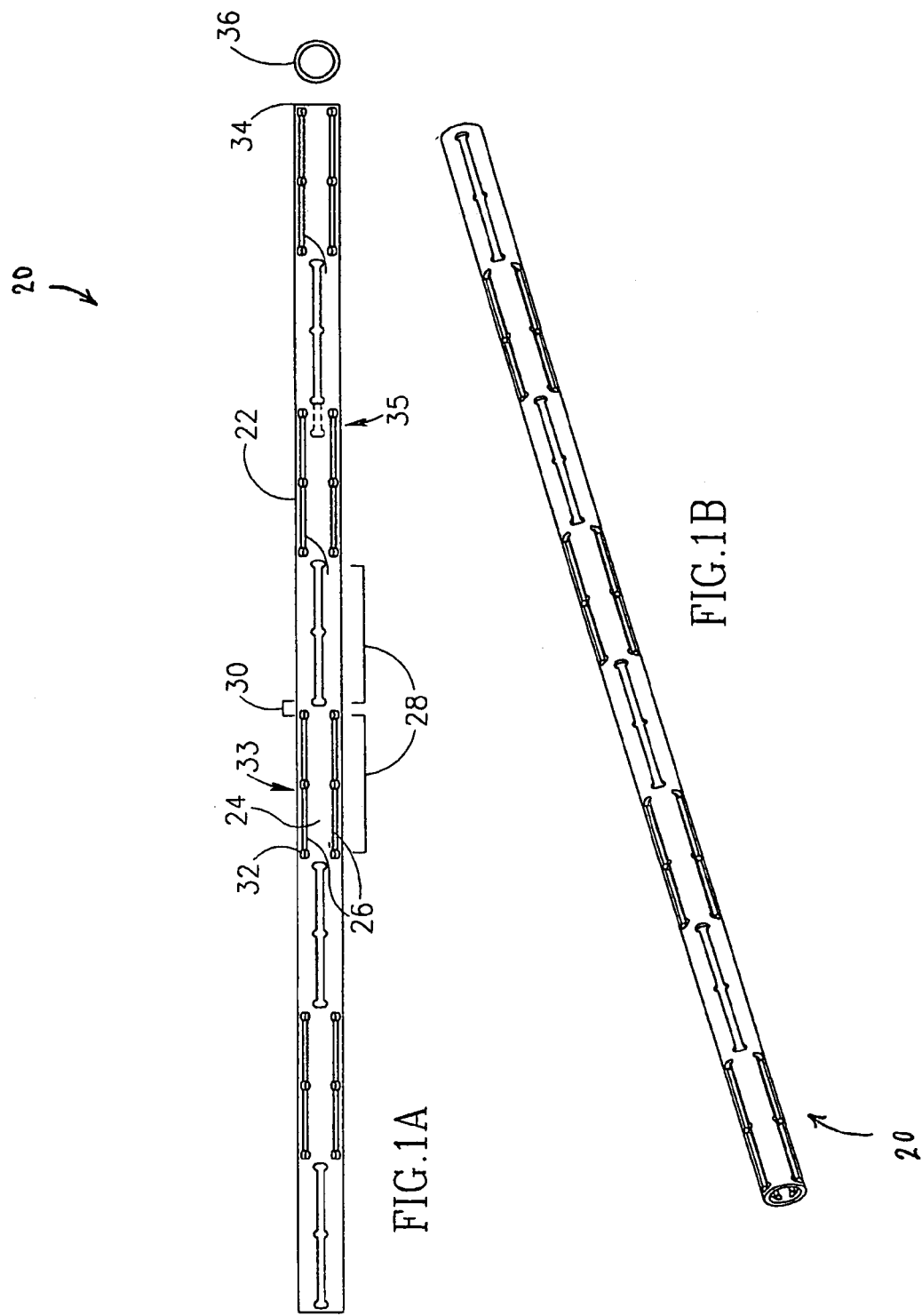

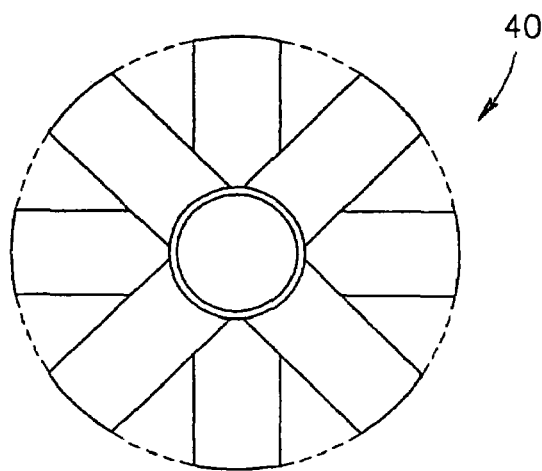
FIG. 1CA
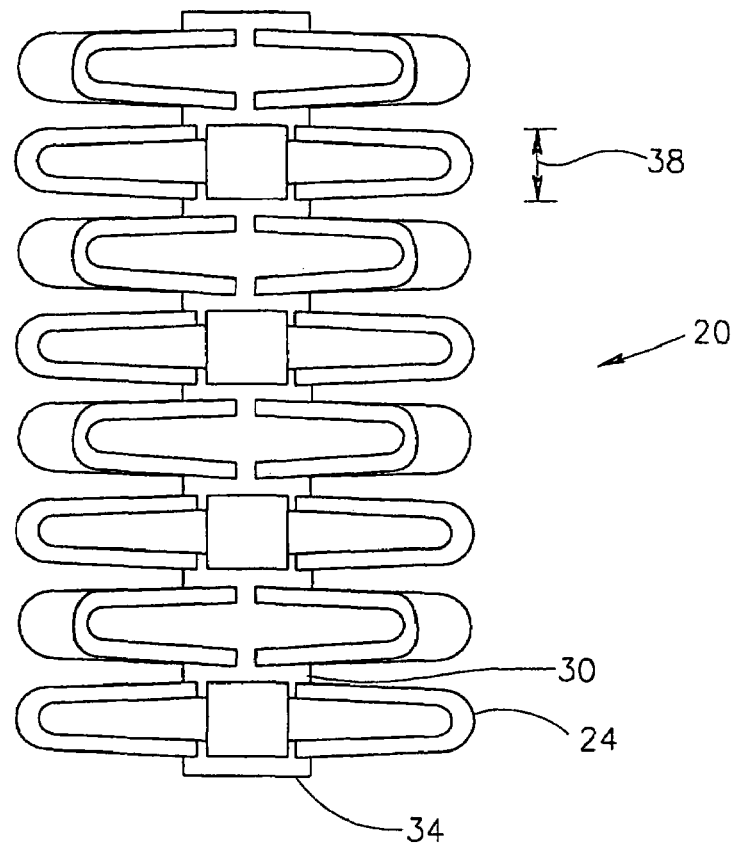
FIG. 1CAB

SECTION B-B

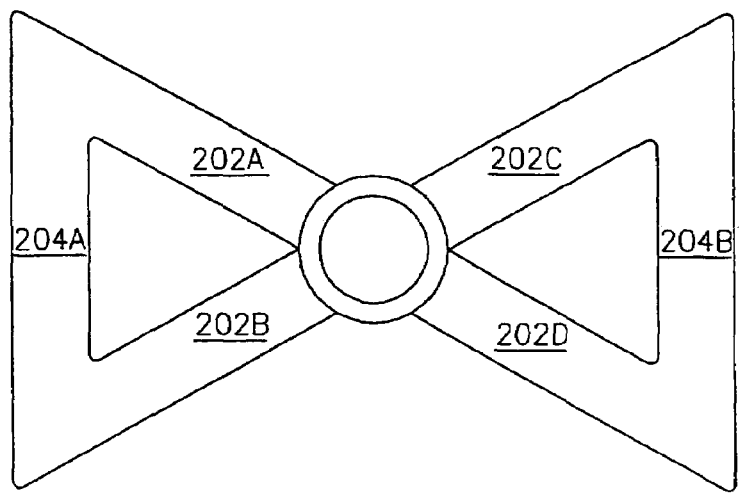
FIG.3C
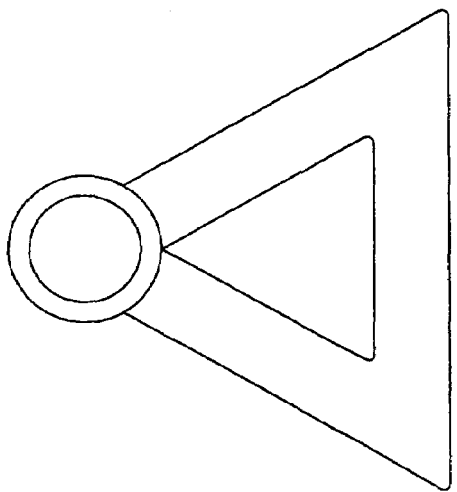
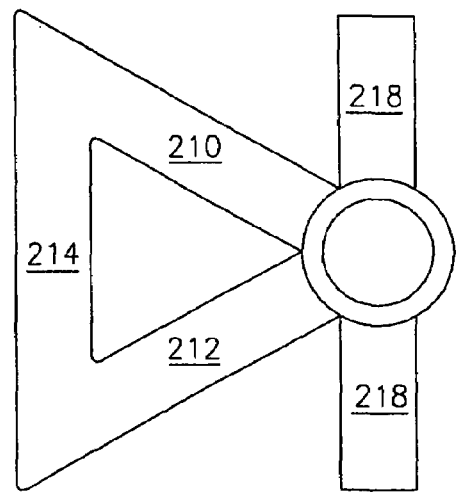
FIG.3D　　　　FIG.3E

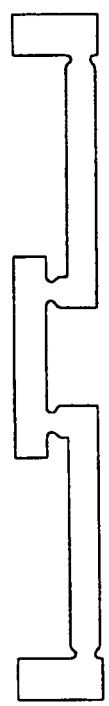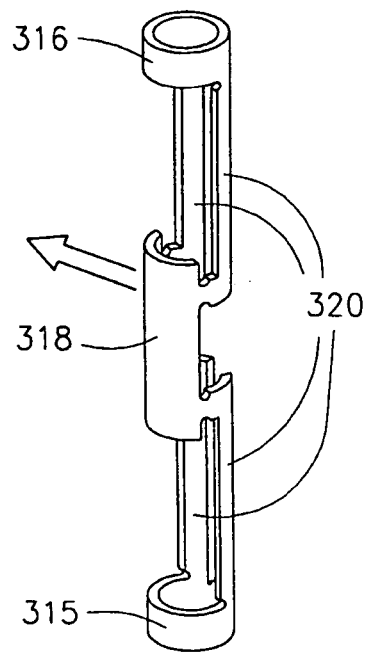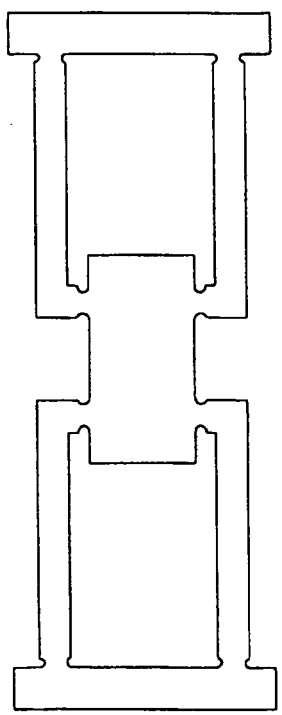
FIG.6XA
FIG.6XB
FIG.6XC

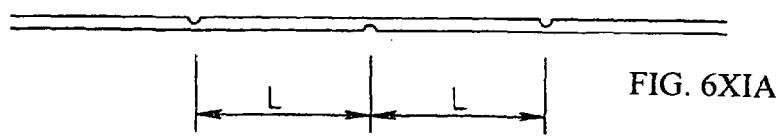
FIG. 6XIA
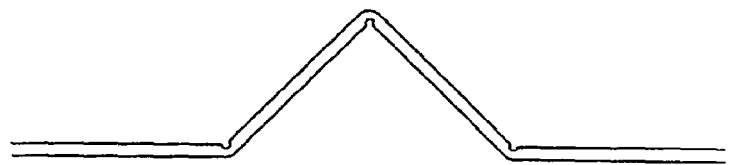
FIG. 6XIB
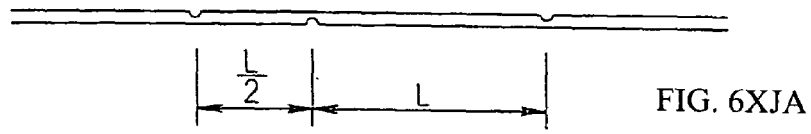
FIG. 6XJA
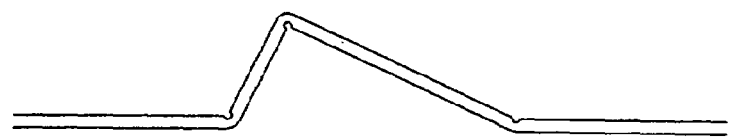
FIG. 6XJB
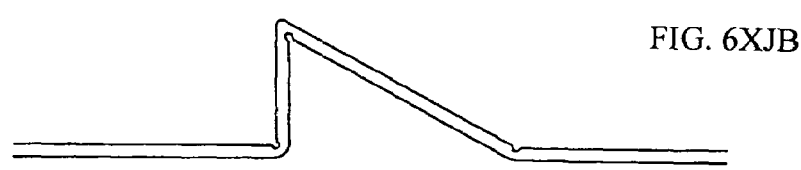
FIG. 6XJC
FIG. 6XJD

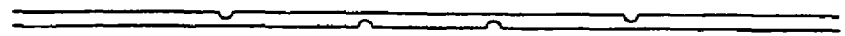
FIG. 6XKA
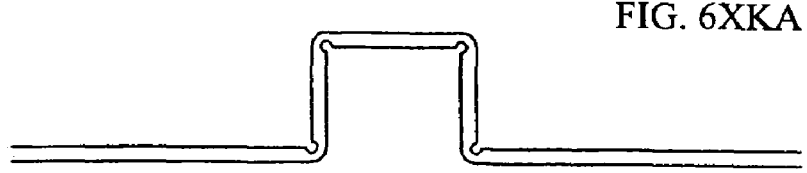
FIG. 6XKB
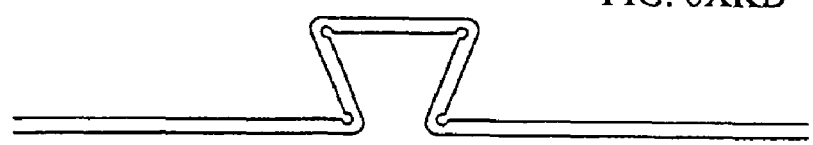
FIG. 6XKC
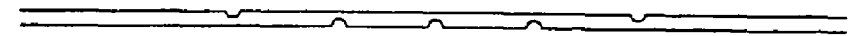
FIG. 6XLA
FIG. 6XLB

FIG. 8Aii

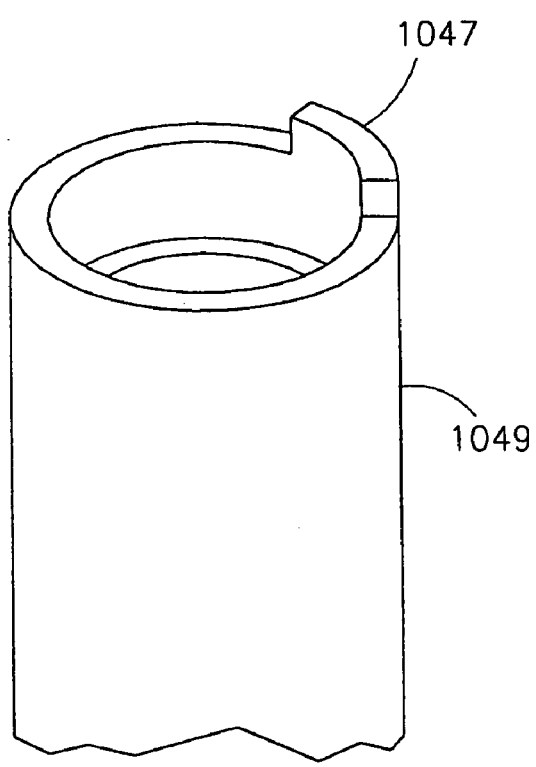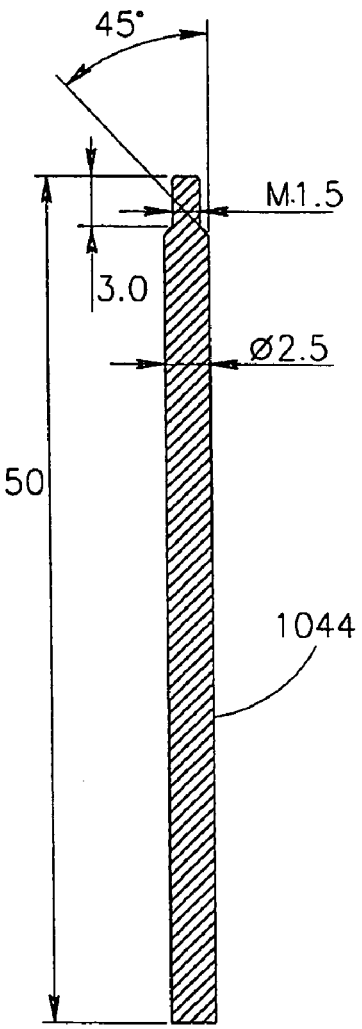
FIG.16C
FIG.16D

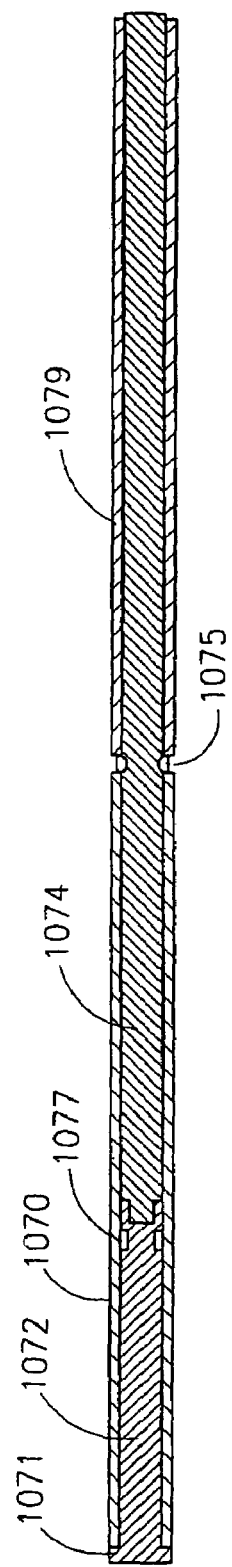
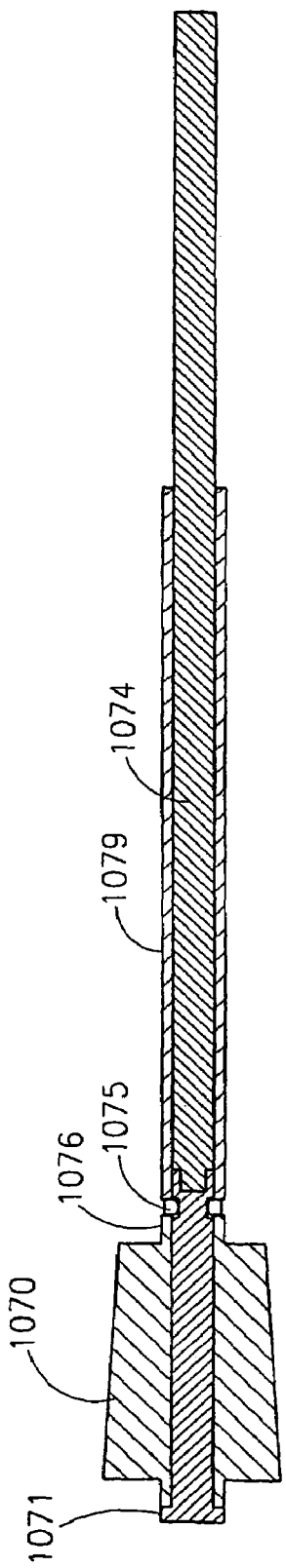

EXPANDABLE INTERVERTEBRAL SPACER

RELATED APPLICATIONS

This application is a U.S. national filing of PCT Application No. PCT/IL00/00058, filed Jan. 27, 2000. This application is also related to two PCT applications, PCT/IL00/00055, and PCT/IL00/00056, both designating the US and both filed on Jan. 27, 2000, the disclosures of which are incorporated herein by reference. This application is also related to PCT Application No. PCT/IB98/00523, the disclosure of which is incorporated herein by reference.

FIELD OF THE INVENTION

The present invention relates to expandable implants, especially for use as a spinal prosthesis.

BACKGROUND OF THE INVENTION

A common medical situation is that of a ruptured spinal disc. Material that exits the disc may press against the spinal cord, causing severe pain. A ruptured disc is typically treated by a surgical procedure, in which the damaged disc is partially or completely removed, and spinal fusion, in which at least the two vertebrae adjacent the removed disc are fused. Several approaches exist for spinal fusion. In one approach, the two vertebrae are connected using a plate and/or screws. In another approach, a spacer (also called a "cage device") is inserted between the two vertebrae, so that bone growth into the space will fuse the adjacent vertebra. Typically, the axis of the spacer is perpendicular to the axis of the spine and to the plane of the body. Sometimes the spacer includes a plurality of holes, to encourage bone growth into the spacer. PCT publication WO 98/38918, the disclosure of which is incorporated herein by reference, describes a spacer that is inserted in a collapsed condition and expanded to fill the inter-vertebral space. Another type of spacer, exemplified by U.S. Pat. No. 5,123,926 (and others) to Pisharodi, the disclosure of which is incorporated herein by reference, functions like a concrete anchoring screw, in that a portion of the spacer, usually a center portion thereof, expands by a relatively small amount to engage the adjacent vertebrae.

U.S. Pat. No. 5,800,549, the disclosure of which is incorporated herein by reference, describes a flexible disc replacement that is inserted using a syringe. However, this replacement does not fuse adjacent vertebrae, rather, it is designed to replace the form and function of a removed inter-vertebral disc.

One disadvantage of some of known fusion devices is that a relatively large entry hole in the body is required to insert the device. In some, a regular-sized surgical incision is required. In others, a minimally invasive laproscope-size hole is required, which typically larger than the fusion device size.

Another disadvantage of some known fusion devices is lies in a relative complexity of procedures for delivering the devices.

Another disadvantage of some known fusion devices is a requirement to trade/off the invasiveness of the procedure (e.g., do the spinal process need to be cut or the abdomen opened) and the surface contact area between the fusion device and the bone. Generally, if the contact surface is small, the fusion device embeds itself in the bone and the spine slowly shrinks.

SUMMARY OF THE INVENTION

An object of some preferred embodiments of the present invention is to provide an intra-vertebral spacer that can be inserted using a narrow diameter needle.

An aspect of some preferred embodiments of the invention is that a spacer having a first diameter is inserted and is then expanded to a second, much larger diameter. Preferably, the second diameter is greater than the first diameter by a factor of three, four, five or more. Thus, a spacer for an inter-vertebral space of a 12 mm height may be inserted using a needle having a 4 mm (inner) diameter. However, in some embodiments of the invention, a more modest diameter increase is achieved, for example, between 20% and 200% or 300%.

In a preferred embodiment of the invention, the radial expansion of the spacer is utilized to achieve a high intra-vertebral fill, without an overly invasive surgical procedure. Preferably, a high contact surface between the spacer and the vertebrae is achieved.

An aspect of some preferred embodiments of the invention relates to a family of geometrical structures useful for an expanding spacer. In a preferred embodiment of the invention, the spacer initially comprises a structure having a narrow diameter. When the spacer is expanded, the diameter increases. In a preferred embodiment of the invention, the diameter of the spacer increases at the expense of the length of the spacer, which is shortened. In a preferred embodiment of the invention, the spacer is modified by the expansion from a long, substantially straight object into a shorter object have a wave-like profile. The effective diameter of the modified spacer is that of the wave, which is significantly greater than the initial diameter.

In a preferred embodiment of the invention, the spacer is formed of a hollow tube having a plurality of axial slits formed on its surface. Preferably, the slits are arranged in pairs of parallel slits, each pair defining a spike, which spike is preferably formed when the material between the slits is folded perpendicular to the slits. When the tube is compressed, the spikes fold out, preferably in the shape of an inverted "V". Typically, though not in all embodiments of the invention, a spike comprises a short base, one or more (usually at least two) legs or sides and optionally a top which connects the ends of the legs. In some embodiments, for example the inverted "V", the spike defines a peak vertex instead of or in addition to the top.

In a preferred embodiment of the invention, a plurality of spikes are defined around the circumference of the tube, so that the tube "expands" in all directions. Preferably, all the spikes have the same length. Alternatively, the length of the spike may depend on an angular position of the spike on the circumference. In one example, the circumference includes eight spikes per axial-length unit of tube, the cross-section of the expanded tube having a shape of a square, with four equal-length spikes at the center of each side of the square and four, longer spikes, at the four corners of the square. In a preferred embodiment of the invention, the spacer comprises a plurality of consecutive tube segments, each segment including one or more spikes. In one example, a square cross-section is achieved by alternating segments of two types, one having shorter spikes (at square sides) and the other having longer spikes (at square corners). Alternatively, the spike lengths are not rotationally symmetric. Alternatively or additionally, the cross-section is not rotationally symmetric.

Alternatively or additionally, the spike lengths and/or geometry vary as a function of the axial position and possibly also the angular position of the spike along the spacer. In a preferred embodiment of the invention, the spike arrangement and/or length conforms to an expected shape of the inter-vertebral space.

A finished spacer, in accordance with some preferred embodiments of the invention, comprises a plurality of spikes that are provided into the body to provide a desired geometrical shape, for example to space apart two vertebrae. The tube body parts that do not expand, serve to interconnect the spikes, for example to prevent them from getting lost and/or for aiding in or performing guiding the final placement of the spikes, so that the desired final geometry is achieved. Thus, geometric constructs other than spikes may also be provided to a same effect.

In a preferred embodiment of the invention, each spike is defined by two parallel slits of equal length. Alternatively, the two slits are not of equal length. Alternatively or additionally, the slits are not parallel, for example the slits being staggered. Alternatively or additionally, at least some of the spikes may be defined by more than two slits, for example three or four slits.

In a preferred embodiment of the invention, the slits are parallel to the axis of the tube. Alternatively, at least some of the slits or pairs of slits are not parallel to the tube. In one embodiments of the invention, the slits define a spiral on the tube.

In a preferred embodiment of the invention, the extended spikes are substantially normal to the tube axis. Alternatively, at least some of the spikes are at an angle to the axis. In one example, the outside spikes are angled out, for example to better grasp surrounding bone tissue. In another example, at least some of the spikes are angled in, for example to exert compressive forces on a bone, for example to bring together a broken bone into which the spacer is inserted.

In a preferred embodiment of the invention, the spikes are substantially straight. Alternatively, at least some of the spikes are curved, for example in a plane which includes the spike and the tube axis and/or out of the plane. Alternatively to being curved, at least one spike may comprise a plurality of straight portions, each portion at an angle to another portion of the spike.

In a preferred embodiment of the invention, the spikes are normal to the tube surface. Alternatively, at least one of the spikes is not normal to the surface. In one example, the spikes exit the tube surface at a parallel or near-parallel angle to the tube surface.

In a preferred embodiment of the invention, the expanded spacer defines a generally cylindrical shape, whose axis is coincident with the axis of the tube. In some embodiments, the cross-section of the expanded spacer is other than a circle, (e.g., a rectangle), but such a spacer preferably has a main axis which is coincident with that of the tube. In other preferred embodiments of the invention, however, the main axis of the expanded spacer is not coincident with that of the tube. In one example, the axes may be parallel, for example if when viewing the spacer cross-section all the spikes on one side of the spacer are longer than those on an opposite side. In another example, the axes may be non-parallel or even non-planar. One situation where non-parallel axes are useful is when the spacer is inserted between the vertebrae at an oblique angle (e.g., from a posterior-lateral direction). In such an insertion, it is still desirable that the expanded spacer be parallel to the vertebral end-plates. In a preferred embodiment of the invention, the spike lengths on the spacer are arranged so that when a spacer is inserted at the oblique angle and then expanded, the axis of the expanded spacer profile is substantially aligned with one of the axes of the body. In some cases, two spacers are inserted at different oblique angles, so that they better fill the intra-vertebral space.

In a preferred embodiment of the invention, the cross-section of the tube is circular. Alternatively, the cross-section is that of a polygon, for example a square or a triangle, preferably one having a same number of sides as there are spikes around the circumference of the tube.

Alternatively to spikes being formed of a surface of a hollow tube, the tube itself (which need not be hollow), or a ribbon, may distort to form a wavy side profile.

An aspect of some preferred embodiments of the invention relates to forming the tube of a material having an uneven thickness and/or mechanical properties. In some embodiments, mechanical characteristics of a spacer are modified after the spacer (or a tube from which it is cut) is constructed. In other embodiments, such mechanical characteristics may be at least partly modified before the spacer is formed. In a preferred embodiment of the invention, increased thickness and/or strength is provided at points or areas where stress is concentrated when pressure is applied to the spikes in an expanded spacer. Alternatively or additionally, increased thickness and/or strength is provided at points where stress is concentrated when pressure is applied to the spikes in an expanded spacer. Alternatively or additionally, increased thickness and/or one or more protrusions are provided on one or more spikes to mechanically block a collapsing of the spikes after the tube is expanded. In one example, when the spacer comprises alternating segments of spikes, a segment may include one or more protrusions which strengthen the spikes on an adjacent segment. Alternatively or additionally, a lower strength and/or pre-stressing is applied to portions of the tube which are expected to fold (and/or stretch) when the tube is expanded. Alternatively or additionally, variations in thickness and/or strength and/or elasticity define portions of the spacer which better conform to surrounding tissue. In some embodiments of the invention, the spacer matches the geometry of the surrounding tissue. In other embodiments, the mechanical characteristics of the spacer are matched to the surrounding tissue, for example providing more give where the spacer is against a hard bone.

An aspect of some preferred embodiments of the invention relates to a inter-vertebral spacer having extending spikes, in which at least some of the spikes have a non-V shaped profile. In a preferred embodiment of the invention, the spikes have a flat top, possibly with small protrusions formed thereon, so that the spikes do not dig into the vertebrae. Alternatively or additionally, the spikes have concave sides, so that when are stressed, they do not collapse.

An aspect of some preferred embodiments of the invention relates to the expansion of a spacer. In a preferred embodiment of the invention, the expansion proceeds from one end of the spacer to the other end, with spikes at one segment of the spacer being fully extended before adjacent spikes are extended. Alternatively, all the spikes are extended at the same time. Alternatively, the order of extension is not controlled. Alternatively, first a first group of spikes are partially extended, then, after other spikes are at least partially extended, the first group of spikes are extended to a greater amount. In a preferred embodiment of the invention, the expansion of the spacer is controlled by a shaping element inserted therein and/or using an outer collar which limits or blocks the extension of the spikes. Possibly, the spacer includes an inner thread to engage the shaping element. Alternatively or additionally, the expansion is controlled by providing different parts of the spacer with different mechanical strengths, so that when expanded, the weaker parts expand first.

An aspect of some preferred embodiments of the invention relates to limiting an extension dimension of the spikes. Generally, a spike is defined by two sides of a folded strip of material, which, together with a base defined by section of the tube (or of its axis), form a triangle (or other shapes, as described below). Since the length of the two material sides of the spike are generally limited by the slits to a fixed amount, the final extended length of the spike (i.e., the triangle height) is inversely related to the length of the base. In some embodiments of the invention, the spacer is axially compressed so that the length of the base is substantially zero (excluding the thickness of the spike itself). Alternatively, in a preferred embodiment of the invention, an axial contraction of the tube is restricted, so that the length of the base is significant. Preferably, a protrusion in the spike, in one or both of the two sides of the spike, defines a minimal distance between the sides, and hence a minimum size base and a maximum length of a spike. Alternatively, the tube body itself may include a mechanical limitation to its contraction. In one example, two slits may define a section of material which, when the tube is expanded (and axially compressed) folds upon itself or protrudes inside the tube, rather than extending outward as a spike. The axial contraction is thus limited by the thickness of the folded material or by the material butting against the inside of the tube.

Alternatively to a spike being defined by two legs, a spike may be defined by three or more legs which are non-planar. In one example the three legs and the base form a spike having a tetrahedral shape. Alternatively, two legs and a top (rather than a base) may be used to define a spike having a rectangular or an upside-down triangle profile.

An aspect of some preferred embodiments of the invention relates to sections cut out of the tube, to control the spacer characteristics. In a preferred embodiment of the invention, the missing sections are used to define an expanded spacer geometry. In one example, a section of the tube which defines a spike is mostly missing from the spacer. When the spacer is expanded (and axially compressed) the two sides of the missing section advance until they abut and further axial contraction is impossible or meets a greater resistance. In another example, a missing section of the tube makes one side of the spacer weaker and causes the spacer to bend in that direction when expanded.

Alternatively or additionally, missing sections of the spacer (tube and/or spike portions) may exist for encouraging bone growth into the spacer.

Alternatively or additionally to missing sections of the spacer, one or more slits may be defined in the spacer to affect its expanded geometry, for example the geometry of the tube section, possibly independently of the spike geometry.

An aspect of some preferred embodiments of the invention relates to spacers which include struts, where each strut preferably interconnects two or more spikes, when the spacer is deployed. In a preferred embodiment of the invention, the struts are formed from the surface of the tube which also forms the spikes. Alternatively, the struts are provided by a second layer of material overlaid or under-laid on the layer from which the spikes are formed. The second layer is, in some preferred embodiments, attached to the first layer only at points where the struts are to be connected to the spikes, in the expanded spacer.

In a preferred embodiment of the invention, the struts interconnect spike peaks. Alternatively or additionally, the struts may connect spike sides, for example at their centers. Alternatively or additionally, the struts may connect sides with peaks. Alternatively or additionally, the spikes may connect spike portions with the tube itself. Preferably, although not required, the interconnected spikes and struts form triangular or tetrahedral shapes.

In a preferred embodiment of the invention, a single strut interconnects two spikes. In some embodiments, a single spike may be connected to more than one strut, for example, in a spacer having four spikes around its circumference, four struts may be provided to form a ring which encloses the spacer cross-section. Alternatively or additionally to radially interconnecting spikes, the struts may axially inter-connect spikes, for example forming a line of struts which is parallel to the axis of the spacer. Substantially any spike interconnection pattern may be provided, for example, a spiral strut path which interconnects spikes to define a spiral pattern on the expanded spacer (e.g., around the axis of the spacer).

In a preferred embodiment of the invention, the struts are parallel to the outline of the cross-section of the spacer, for example defining a rectangle if the spacer has a rectangular cross-section. In other embodiments, however, such parallelism is not required. For example, the struts may define a rectangle which is rotated at 45° relative to the spacer cross-section.

In a preferred embodiment of the invention, the struts are arranged in a radial symmetry. Alternatively or additionally, the struts are arranged in an axial symmetry. Alternatively, the struts are arranged asymmetrically. Preferably, the pattern of strut-asymmetry matches and/or is aligned with a pattern of spike asymmetry. Alternatively, the patterns do not match and/or are not aligned.

In a preferred embodiment of the invention, the struts structurally limit relative movement between spikes and/or spacer portions, preferably, by resisting movement of two points connected by spikes towards (and/or away from) each other. Alternatively or additionally, the struts may provide other structural support, for example, to limit relative outward movement of two points, to limit expansion of a portion of the spacer, to limit certain deformations of the spacer under stress and/or to limit spike extension.

Alternatively or additionally to using struts, one or more of these strut-functions may be provided by wires. As used herein the differences between wires and struts (both of which are examples of inter-connecting elements), are mainly in their relative rigidity and thicknesses. Additionally, struts usually maintain the same rigid configuration when the spacer is expanded and when it is collapsed (or folded at pre-defined points), while wires may change their configuration, for example being folded when the spacer is collapsed and being extended when the spacer is expanded. Alternatively or additionally to directly structural functions, the struts and/or wires may be used to effect a desired contact surface, for example, to enhance fusion with bone or to limit embedding or sinking of spikes in the surrounding bone.

In a preferred embodiment of the invention, the inter-connecting elements have a fixed cross-section. Alternatively, the cross-section and/or the mechanical-properties may vary along the length, width and/or thickness of an inter-connecting element. Possibly, different inter-connecting elements (e.g., different struts) may have different geometries and/or material properties.

An aspect of some preferred embodiments of the invention relates to locking mechanisms for an axially contracting spacer. In a preferred embodiment of the invention, the locking mechanisms lock an inner bolt of the spacer against an outer portion of the spacer. Preferably, the locking is activated by retracting a member used to contract the spacer. Alternatively, the locking is activated by advancing and/or rotating the member. In a preferred embodiment of the invention, the locking mechanism and/or a member freeing mechanism is primed by the spacer completing its axial contraction.

An aspect of some preferred embodiments of the invention relates to a tissue excavation tool, especially for disc removal. In a preferred embodiment of the invention, the tool comprises an elongate member having at the end thereof an expandable portion comprising a plurality of spikes. The tool may be inserted into the spine at a small diameter and the spikes are then extended. Tissue excavation is preferably performed by rotating the tool, so the spikes disintegrate the disc tissue. Preferably, the tool is hollow so the disintegrated tissue may be vacuumed out of the intra-verbal space. Alternatively or additionally, the tool may be bent, to reach locations out of line with from the entry point of the tool. Alternatively or additionally, a stylet is inserted into a hollow of the tool, to guide it to various locations in the inter-vertebral space. The tool is preferably formed of metal, however, it may be formed of other materials, for example plastic. The rotational speed of the tool may be, low, for example 100 RPM or high, for example 3000 RPM. In some embodiments the spikes have sharpened edges, while in other embodiments such sharpened edges are not required and/or not provided.

An aspect of some preferred embodiments of the invention relates to using an expandable tube-spikes structure for other uses, for example for bone anchoring, for tooth implanting, for supporting fractured bones, including for example long, short and bent bones, as an bone anchor (preferably inside the medullar channel) for a joint, such as a hip or finger joint, and/or for gradually modifying bone structure. In a preferred embodiment of the invention, the spacer is inserted into a bone to be modified and/or supported using a needle. In one example, the spacer is inserted in an unexpanded configuration and once the bone segments are aligned, for example using x-ray imaging techniques, the spacer is expanded to grasp the bone segments and possibly urge them together. In a preferred embodiment of the invention, the spacer may be removed once the bone is knit by collapsing the spacer and removing it using a thin cannula.

An aspect of some preferred embodiments of the invention relates to controlling the configuration of an implanted spacer using externally applied power and/or controls. In a preferred embodiment of the invention, the expansion of the spacer is increased and/or decreased responsive to such externally applied power and/or controls signals. Preferably, such increase and/or decrease is used to gradually bend, straighten, lengthen, shorten twist and/or otherwise model bones in which the spacer is implanted, for example ribs or leg bones. In one example, bones are bent and/or straightened, using a spacer whose bend is related to its axial length. Preferably, a spacer for bone modeling automatically extends/distorts by a predetermined amount each day, in response to an outside command or using a ratchet mechanism.

An aspect of some preferred embodiments of the invention relates to using an implanted spacer to report on internal physiological parameters. In one example, the spacer reports a degree of bone ingrowth, such as to enable a treating physician to monitor the healing process. In another example the spacer reports applied torque and pressure, such as to enable a treating physician to assess structural problems of the bone and/or the spacer. In a preferred embodiment of the invention, a sensor, for example a silicon pressure or strain sensor) is integrated with the spacer. Alternatively, the body of the spacer itself provides at least some of the sensing, for example, by vibration modes of the spacer changing responsive to bone ingrowth and/or by tracking (using medical imaging techniques) changes in the configuration of the device and especially configuration changes in designated pressure sensitive portions thereof. Such a pressure sensitive portion, can be, for example, a hollow bubble of metal which is compressed by external pressure from the growing bone. The shape of the bubble may be determined, for example using x-ray imaging or by analyzing resonance characteristics of the spacer.

There is thus provided in accordance with a preferred embodiment of the invention, an expandable spacer, comprising:

an axial tube having a surface, a proximal end, a distal end and a length, wherein, said surface defines a plurality of slits, said plurality of slits defining at least two axially displaced extensions, such that when said tube is axially compressed, said extensions extend out of said surface and define a geometry of an expanded spacer.

Preferably, said at least two axially displaced extensions comprises at least three extensions, which three extensions extend in at least three different directions from said tube. Alternatively or additionally, said at least two axially displaced extensions comprises at least four extensions, which four extensions extend in at least four different directions from said tube.

In a preferred embodiment of the invention, said slits are straight. Alternatively or additionally, said slits are curved.

In a preferred embodiment of the invention, said slits are narrow.

In a preferred embodiment of the invention, said slits have a non-trivial width for at least part of their length.

In a preferred embodiment of the invention, said slits are substantially parallel to said tube axis.

In a preferred embodiment of the invention, said slits are not parallel to said tube axis.

In a preferred embodiment of the invention, said slits are arranged in pairs of same length.

In a preferred embodiment of the invention, said slits are arranged in pairs of different lengths.

In a preferred embodiment of the invention, slits associated with one extension axially overlap slits associated with a second, axially displaced, extension.

In a preferred embodiment of the invention, said proximal end of said tube defines a proximal end-cap, which end-cap extends outside of a volume defined by the geometry of said extended extensions.

In a preferred embodiment of the invention, said distal end of said tube defines a distal end-cap, which end-cap extends outside of a volume defined by the geometry of said extended extensions. Alternatively, at least one of said extensions is flush with said proximal end of said tube. Alternatively, at least one of said extensions is flush with said distal end of said tube.

In a preferred embodiment of the invention, the spacer comprises at least one spur axially extending from said spacer, to engage tissue adjacent said spacer. Preferably, said at least one spur comprises at least two spurs axially extending from said spacer.

In a preferred embodiment of the invention, the spacer comprises an inner bolt. Preferably, said inner bolt has a smooth exterior. Alternatively, said inner bolt has a threaded exterior.

In a preferred embodiment of the invention, said bolt has a base, which base has an external diameter greater than an inner diameter of said tube, such that said base restricts axial motion of tube in one direction relative to the bolt.

In a preferred embodiment of the invention, said bolt has a head, which head locks against at least one end of said tube, to prevent axial expansion of said tube. Preferably, said head is adapted to engage at least one protrusions extending from said tube toward said bolt head. Alternatively, said head comprises at least one protrusions extending from said head toward said tube, to engage said tube. Alternatively, said head comprises a flange, flared to have an outer diameter greater than an inner diameter of said tube.

In a preferred embodiment of the invention, said bolt is adapted to engage a pole element for holding said bolt during deployment of said spacer. Preferably, said bolt has an inner thread for engaging said pole element. Alternatively, said bolt mechanically engages said pole element as long as a head of said bolt is constrained by said tube.

In a preferred embodiment of the invention, said spacer comprises a plurality of segments, each segment defining one or more extensions that extend from said spacer. Preferably, said segments comprises at least two segment types, each segment type defining extensions that extend in different directions relative to said tube. Preferably, said two segment types comprises a horizontal segment defining two extensions that extend along a line and a segment defining four extensions that extend at about ±45° to said two extensions.

In a preferred embodiment of the invention, an extension direction of at least one of said at least two extensions is normal to said tube.

In a preferred embodiment of the invention, an extension direction of at least one of said at least two extensions defines a sharp angle with said tube axis, in a plane containing said tube axis.

In a preferred embodiment of the invention, at least one of said at least two extensions does not extend along a direction perpendicular to said tube.

In a preferred embodiment of the invention, at least one of said at least two extensions has, in a plane containing said tube axis, a profile of a triangle, with the tip pointed away from said tube.

In a preferred embodiment of the invention, at least one of said at least two extensions has, in a plane containing said tube axis, a curved profile.

In a preferred embodiment of the invention, at least one of said at least two extensions has, in a plane containing said tube axis, a profile that narrows and then widens, along a direction away from the tube.

In a preferred embodiment of the invention, at least one of said at least two extensions has, in a plane perpendicular to said tube axis, a profile that narrows, along a direction away from the tube.

In a preferred embodiment of the invention, at least one of said at least two extensions has, in a plane perpendicular to said tube axis, a profile that narrows and then widens, along a direction away from the tube.

In a preferred embodiment of the invention, at least one of said at least two extensions has, in a plane perpendicular to said tube axis, a uniform profile.

In a preferred embodiment of the invention, at least one of said at least two extensions has, a pointed top profile. Alternatively, at least one of said at least two extensions has, a top profile substantially the same size as a base of said extension. Alternatively, at least one of said at least two extensions has, a top profile substantially the larger that a base of said extension.

In a preferred embodiment of the invention, said extensions are unevenly distributed along said axis. Alternatively, said extensions are evenly distributed along said axis.

In a preferred embodiment of the invention, said extensions are unevenly distributed along a circumference of said tube. Alternatively, said extensions are evenly distributed along a circumference of said tube.

In a preferred embodiment of the invention, said different ones of said extensions have different geometries. Alternatively or additionally, said extensions are distributed in a spiral pattern. Alternatively or additionally, said tube axis is coaxial with an axis of said expanded geometry.

In a preferred embodiment of the invention, said tube axis is parallel to an axis of said expanded geometry.

In a preferred embodiment of the invention, said tube axis is not-parallel to an axis of said expanded geometry. Preferably, said tube axis and said expanded geometry axis are designed for oblique insertion of a spacer to be aligned, in its expanded state with vertebra.

In a preferred embodiment of the invention, said spacer has an expanded geometry cross-section of a circle.

In a preferred embodiment of the invention, said spacer has an expanded geometry cross-section of a rectangle.

In a preferred embodiment of the invention, a cross-section of said expanded geometry varies along an axis of said expanded geometry.

In a preferred embodiment of the invention, a cross-section diameter of said expanded geometry varies along an axis of said expanded geometry. Preferably, said cross-section is rectangular and wherein said cross-sectional diameter increases along said expanded geometry axis.

In a preferred embodiment of the invention, a cross-section diameter of said tube varies along an axis of said tube. Alternatively or additionally, a cross-section of said tube varies along an axis of said tube.

In a preferred embodiment of the invention, said tube has a circular cross-section.

In a preferred embodiment of the invention, said tube has an elliptical cross-section.

In a preferred embodiment of the invention, said tube has a rectangular cross-section. Alternatively or additionally, said tube axis is bent, when the spacer is unexpanded.

In a preferred embodiment of the invention, said tube axis is straight when the spacer is unexpanded. Alternatively or additionally, said tube axis is bent when the spacer is expanded.

In a preferred embodiment of the invention, said tube axis is straight when the spacer is expanded.

In a preferred embodiment of the invention, the spacer comprises a ratchet mechanism to maintain said spacer in an expanded configuration.

In a preferred embodiment of the invention, the spacer comprises at least one portion of said spacer that prevents axial contraction of said spacer. Preferably, said at least one portion comprises a pair of tabs that abut when the spacer is axially contracted. Alternatively, said at least one portion comprises a strip that folds and forms a thickness between two opposing sides of said spacer, preventing the opposing sides from meeting.

In a preferred embodiment of the invention, the spacer comprises at least protrusion on at least on of said extensions, to prevent collapsing of said extension.

In a preferred embodiment of the invention, the spacer comprises at least protrusion on at least on of said extensions, to interlock said two extensions.

In a preferred embodiment of the invention, the spacer comprises at least one interconnecting element for interconnecting said extensions when the extensions are expanded.

Preferably, said interconnecting element comprises a flexible wire. Alternatively, said interconnecting element comprises a substantially rigid strut.

In a preferred embodiment of the invention, at least one of said extensions comprises only bending joints.

In a preferred embodiment of the invention, at least one of said extensions comprises at least one twisting joint.

In a preferred embodiment of the invention, at least one of said extensions comprises a lift-up-extension in which a significant axial section of the tube is lifted away from said tube to form said expanded geometry.

In a preferred embodiment of the invention, at least one of said extensions comprises at least two legs that are coupled by a extension top.

In a preferred embodiment of the invention, at least one of said extensions comprises at least three legs that are coupled by a extension top.

In a preferred embodiment of the invention, at least one of said extensions comprises at least four legs that are coupled by a extension top. Alternatively or additionally, at least one of said extensions comprises at least two legs, which legs are aligned with the tube axis. Alternatively or additionally, a plurality of annealed locations are provided on said spacer to assist in expansion of said spacer. Alternatively or additionally, a plurality of etched locations are provided on said spacer to assist in expansion of said spacer. Alternatively or additionally, a plurality of holes are provided on said spacer to assist in expansion of said spacer. Preferably, said holes distribute stress in said spacer.

In a preferred embodiment of the invention, said spacer is annealed as a unit.

In a preferred embodiment of the invention, said spacer comprises means for changing the axial length of the spacer over time, after the spacer is implanted. Alternatively or additionally, said spacer is formed of metal. Alternatively, said spacer is formed of plastic.

In an alternative preferred embodiment of the invention, said spacer is formed of a combination of distinct zones of different materials.

In a preferred embodiment of the invention, said spacer comprises an elastic material, which is elastically deformed by the extension deformation. Alternatively or additionally, said spacer comprises a plastic material, which is plastically deformed by the extension deformation. Alternatively or additionally, said spacer comprises a super-elastic material, which is super-elastically deformed by the extension deformation. Alternatively or additionally, said spacer comprises a shape-memory material.

In a preferred embodiment of the invention, said spacer is adapted to be axially deformed under axial pressures of over 20 Kg. Alternatively or additionally, said spacer is adapted to be axially deformed under axial pressures of over 30 Kg. Alternatively or additionally, said spacer is adapted to be axially deformed under axial pressures of over 50 Kg. Alternatively or additionally, said spacer is adapted to be axially deformed under axial pressures of over 70 Kg. Alternatively or additionally, said spacer is adapted to be axially deformed under axial pressures of over 90 Kg.

In a preferred embodiment of the invention, said spacer is adapted to remain expanded in a vertebra of an active human, when placed with the tube axis perpendicular to a spine of said human. Alternatively or additionally, said tube has a cross-sectional diameter smaller than 2 times the maximal cross-sectional diameter of said expanded geometry.

In a preferred embodiment of the invention, said tube has a cross-sectional diameter smaller than 4 times the maximal cross-sectional diameter of said expanded geometry.

In a preferred embodiment of the invention, said expanded geometry is sized to fit between two human vertebrae.

In a preferred embodiment of the invention, said extensions have tips and wherein said tips has a surface fill factor of at least 20% relative to the contact surface of a target vertebra with the spacer geometry.

In a preferred embodiment of the invention, said extensions have tips and wherein said tips has a surface fill factor of at least 40% relative to the contact surface of a target vertebra with the spacer geometry.

In a preferred embodiment of the invention, said extensions have tips that contact a surface of target vertebra and wherein said tips has a surface fill factor of at least 60% relative to the contact surface of the target vertebra with the spacer geometry.

In a preferred embodiment of the invention, said expanded geometry covers at least 40% of the surface of a target vertebra, previously contacting a disc.

In a preferred embodiment of the invention, said expanded geometry covers at least 60% of the surface of a target vertebra, previously contacting a disc.

In a preferred embodiment of the invention, said expanded geometry covers at least 80% of the surface of a target vertebra, previously contacting a disc.

There is also provided in accordance with a preferred embodiment of the invention, a spacer, comprising:

an elongate body having a surface and having a maximum cross-section at a portion thereof; and a plurality of extensions radially extending from said body, wherein, said extensions are dense on at least 40% of said body, including said portion, such that at least 50% of a surface area of said body is covered by extensions, wherein said dense extensions define a cross-section having a diameter at least three times a diameter of said body cross-section and wherein said extensions are formed of said surface. Preferably, said extensions are dense on at least 50% of said body. Alternatively or additionally, said extensions are dense on at least 70% of said body.

In a preferred embodiment of the invention, a spacer is coated with a bio-active coating. Preferably, said bio-active coating retards bone ingrowth. Alternatively or additionally, said bio-active coating promotes bone ingrowth.

In a preferred embodiment of the invention, said extensions comprises spikes.

BRIEF DESCRIPTION OF THE DRAWINGS

The present invention will be more clearly understood from the following detailed description of the preferred embodiments of the invention and from the attached drawings, in which:

FIG. 1A shows a flat projection of an expandable spacer, in an un-expanded configuration thereof, in accordance with a preferred embodiment of the invention;

FIG. 1B shows a perspective view of the spacer of FIG. 1A;

FIGS. 1CA and 1CB shows an axial flat projection and a front flat projection of the spacer of FIG. 1A, respectively, in an expanded configuration thereof;

FIG. 2OA-FIG. 2OC illustrates a spacer having an internal end-cap, in accordance with a preferred embodiment of the invention;

FIGS. 3A-3E are axial views of spacers with struts in accordance with preferred embodiments of the invention;

FIGS. 6XA-6XC illustrate a flat-top spike in accordance with a preferred embodiment of the invention;

FIGS. 6XD-6XH illustrate a flat-top spike in accordance with another preferred embodiment of the invention;

FIGS. 6XIA-6XLB illustrate a method of removing portions of a spacer, to achieve a desired spike shape;

FIGS. 16A-16F illustrate a locking mechanism utilizing an expanding flange, in accordance with a preferred embodiment of the invention;

FIGS. 19A-19C illustrate a ring-based locking mechanism, in accordance with a preferred embodiment of the invention;

DETAILED DESCRIPTION OF THE PREFERRED EMBODIMENTS

Basic Spacer (Cage) Description

Figure 1D:
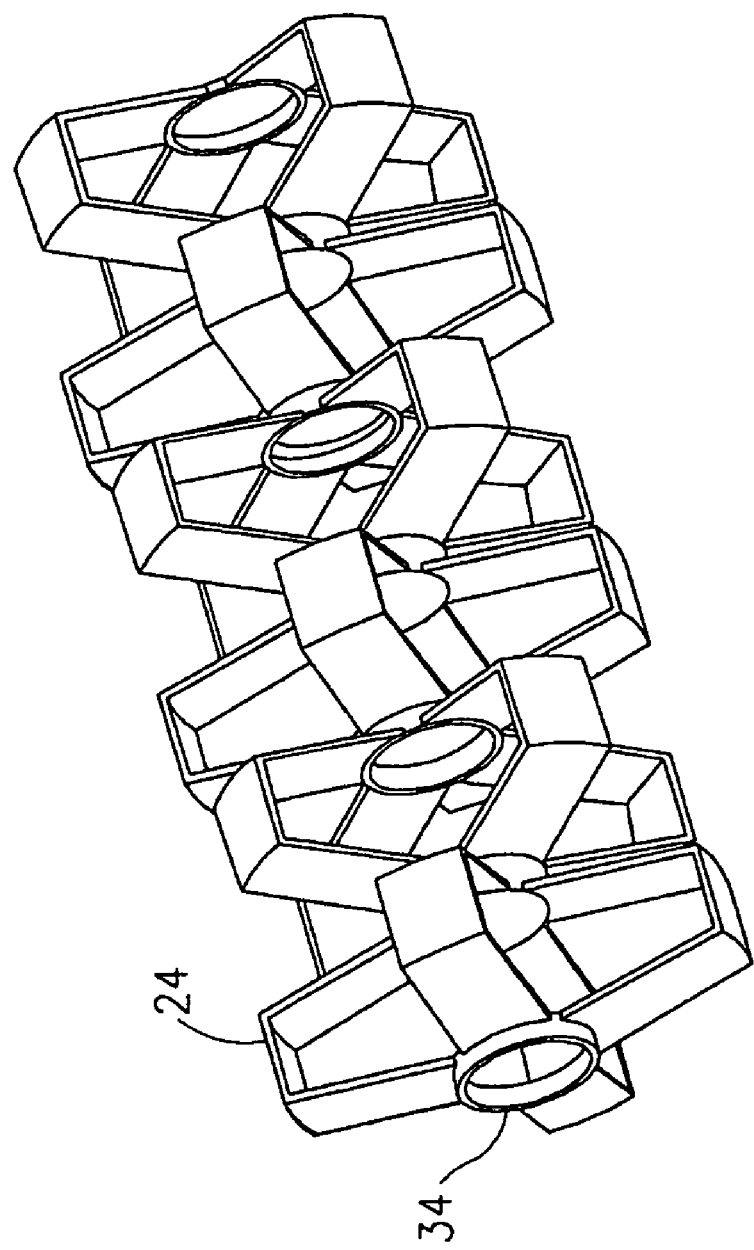
FIG. 1D shows a perspective view of the spacer of FIG. 1A, in an expanded configuration thereof.

FIG. 1A shows a flat projection of an expandable spacer 20, in an un-expanded configuration thereof, in accordance with a preferred embodiment of the invention. FIG. 1B is a perspective view of spacer 20. Spacer 20 comprises an elongate hollow object 22, such as a tube, having a plurality of spikes 24 defined thereon (in a flattened form), each spike being defined by a pair of slots 26. In a preferred embodiment of the invention, the cross-section of tube 22 is a circle, as shown in an axial projection 36 of the spacer. In the embodiment shown in FIG. 1A, tube 22 includes alternating spike segments 28 and non-spike segments 30. At one end of the tube, an end-cap 34 is preferably defined. In a preferred embodiment of the invention, end-cap 34 is hollow. Alternatively, end-cap 34 is solid, but preferably comprising a porous material or including holes, to enhance bone ingrowth. Alternatively or additionally to end-cap 34, spacer 20 is attached to the end of a tube, such that only a portion of the tube, preferably an end portion, has slits defined therein.

FIGS. 1CA-1D show spacer 20 in an expanded configuration, FIGS. 1CA and 1CB using a flat projection (side and axial) and FIG. 1D using a perspective view. When expanded, spikes 28 extend outwards and tube 22 is axially compressed. Non-spike segments 30 and end-cap(s) 34 preferably do not distort. As can be seen in the figures, a considerable expansion in diameter is achieved, for example a five fold expansion. In addition, a considerable axial contraction is achieved, as evidenced by comparing the thickness of a spike 24 in FIG. 1CB (38) with FIG. 1A (28).

Although spacer 20 has been described as including non-spike portions, it should be appreciated that in some preferred embodiments of the invention no such non-spike portions are defined, for example, if the slits are interleaved, as shown by the example of a dotted line 35 in FIG. 1A.

In a preferred embodiment of the invention, tube slits 26 include round holes, for example holes 32, at their ends. Preferably, these holes are defined to reduce the propagation of stress and/or mechanical failure in tube 22. Alternatively or additionally, these holes are defined to weaken the end of the slit so that when spacer 20 is axially collapsed, spikes 28 will preferentially fold out at the ends of the slits. Alternatively or additionally, slits 26 may include holes 33 at their center (the apex of spikes 28), to encourage folding of the spike at the location of the hole.

The above is a description of a limited subset of spacers, further variations are defined below.

Basic Delivery Method

Figure 2A:
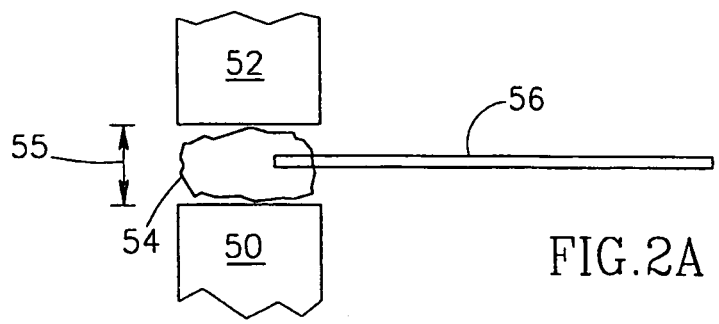
FIGS. 2A-2D illustrate a process of inserting and expanding a spacer, in accordance with a preferred embodiment of the invention.

FIGS. 2A-D illustrate a process of inserting and expanding spacer 20. In FIG. 2A, a damaged disc 54 is located in an inter-vertebral space 55, between a vertebra 50 and a vertebra 52. Typically, before inserting a spacer between the two vertebra, disc 54 is partially or completely removed. Preferably, disc 54 is removed using a minimally invasive technique, preferably using only a thin needle 56, for example as described below with reference to FIGS. 9A and 9B. Alternatively, a laproscopic approach is used, for example as described in WO 98/38918, preferably taking care to minimize trauma to the patient.

In a preferred embodiment of the invention, all the cartilaginous end plate is removed, as known in the art, however, this is not required. Alternatively or additionally, a plurality of holes are formed in the endplate and/or the vertebra itself, to promote bone growth.

Figure 2B:
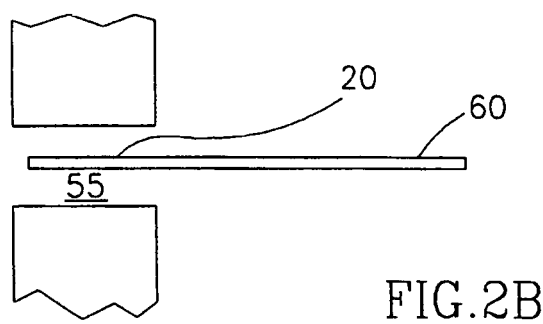

In FIG. 2B, the disc has been removed and a spacer 20 is inserted into inter-vertebral space 55, in an un-expanded configuration. In a preferred embodiment of the invention, spacer 20 is mounted on—or formed at—the end of an elongate member 60. Preferably, spacer 20 is inserted using a syringe or in an "over-tube" which may be retrieved, once the spacer is inserted. Alternatively or additionally, spacer 20 is inserted using X-Ray guidance, to avoid damaging the spinal cord.

Figure 2C:
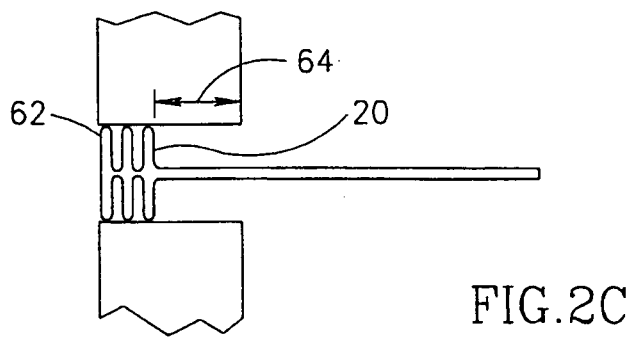

In FIG. 2C, spacer 20 is in the process of being radially expanded (and axially shortened). A portion 62 of spacer 20 is expanded, while a length 64 of spacer 62 is not yet expanded.

Figure 2D:
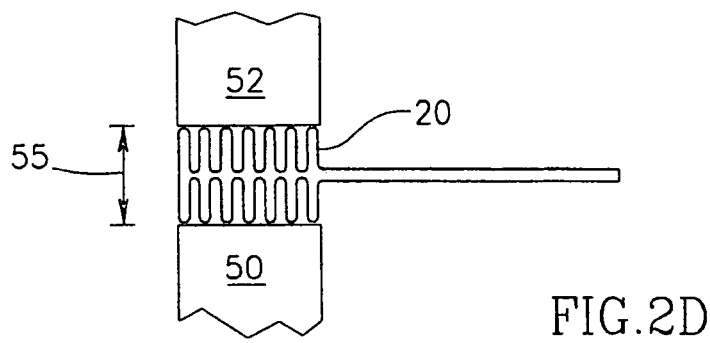

In FIG. 2D, spacer 20 is radially expanded over its entire expansion length and it fills inter-vertebral space 55. In a preferred embodiment of the invention, a fixing material, such as a bone slurry or a setting fixing compound is provided into inter-vertebral space 55, in order to encourage fusion between vertebra 50 and vertebra 52. In the case of a bone slurry, bone chips or bone powder, such setting may require a week or so of bed rest. Preferably, spacer 20 is stiff enough to maintain its shape until the bone sets, so that little or no bed rest is required. Alternatively or additionally, at least some of the required stiffness is provided by the fixing material. Alternatively or additionally, the fixing material serves as a space filler and/or to provide compressive strength. Alternatively or additionally, to injecting a fixing material or as part of the fixing material, growth hormones, enzymes, anti-bacterial pharmaceuticals, anti-inflammatory compounds and/or other bio-active materials may be injected into space 55, to encourage fusion and/or another desired effect. Preferably, the filler material fills the entire space 55 and is contiguous.

OrthoLogic Inc., of Tempe, produces a device named "SpinaLogic", that appears to promote healing by magnetic field generation. In some embodiments of the invention, the spacer comprises or includes magnetic materials, such as ferrite (preferably encapsulated or coated) for controlling the field lines of the magnetic fields. Alternatively or additionally, the SpinaLogic device may be used to promote healing in a standard fashion.

One of the PCT applications mentioned above as being filed on even date, describes an exemplary disc access and spacer delivery system.

Ingrowth Control

In a preferred embodiment of the invention, the bone slurry comprises bone chips, for example spherical or cubic or flat rectangular shaped chips. Such chips may be generated for example using a small oscillating saw and/or osteotome. A pituitary forceps or bone impactor-holder may be used to push the bone chips through a delivery tube, typically but not necessarily a same tube through which the spacer is advanced. In an exemplary application the tube has an inner diameter of 6 mm, so the bone chips should have a largest extent of 5.9 mm.

Exemplary bone sources can be a tricortical autologous crest bone graft, a fibular bone bank graft or a cadaver bone. Alternatively or additionally, the bone slurry can include a mesh, hydroxylapatite and/or ossification accelerating material, such as known in the art. The bone chips may be selected to fit between spikes and through spike sides of a particular spacer used.

In an alternative preferred embodiment of the invention, the fixing material is provided through member 60, rather than through an enclosing tube, as in some embodiments, no such outer tube is provided and member 60 serves as such an outer tube instead, for at least some of the activities in the spine. Alternatively, it is provided using a syringe. It will be appreciated from viewing FIG. 1D that in the expanded configuration, spacer 20 can include ample holes for a bone slurry (and/or new bone growth) to flow between inter-vertebral space 55 and the inside of spacer 20. In a preferred embodiment of the invention, spacer 20 is coated with a bone-growth enhancing material, such as a hormone. Alternatively or additionally, spacer 20 is coated with a material to which new bone growth adheres. Alternatively or additionally, spacer 20 has a rough finish, at least on portions thereof, to encourage bone adhesion thereto. In one example, the finish is created by sandblasting at least portions of the spacer. Alternatively or additionally, the spacer may have holes and/or small protrusions formed thereon, to encourage bone ingrowth. Such holes may be formed on the tube portion and/or on the spikes. Preferably, areas surrounding such holes are treated to be stronger, so that the existence of the holes does not adversely affect the expansion geometry of the spacer.

Alternatively, at least some parts of spacer 20 may be treated to retard bone growth, for example by making them radioactive or by coating them with bone-growth retarding material. Such retardation may be useful in order to allow removal of the spacer (described below). Preferably such retardation is short-term, and the effect fades after a time, so that if the spacer is not removed, bone growth will surround it. Alternatively or additionally, at least a part of the spacer has a finish and or a geometry (e.g., no holes) which discourages bone ingrowth. Additionally or alternatively, the spacer may enclose or be enclosed in an impenetrable material, for example a balloon, which is inflated by the spacer being expanded. Possibly, the balloon surface is conducive to tissue attachment and/or degrades after a time. Alternatively, the balloon is attached to the spacer along its length and the spacer is expanded by inflating the balloon.

Alternatively, such an outer mesh, fabric or balloon may be used to enhance the contact between the spacer and the bone, for example to increase the contact area and/or to prevent high pressure contact points between the spacer and the surrounding bone, except possibly at some desired locations. The mesh and/or balloon are preferably inserted prior to the spacer and the spacer is expanded inside the mesh or balloon. Alternatively, the mesh or balloon is mounted on the spacer prior to the spacer being inserted into the body. Possibly, the mesh is bioabsorbable, so that after the bone grows in the mesh disappears. Alternatively to a mesh, a more tightly woven fabric or a felt may be used. It is noted that many temporary bone ingrowth structures, are known in the art and may be provided between (and/or inside) the spacer and the bone.

Capping the Spacer

The next step in the implantation method is preferably to close up the incision used to provide spacer 20, or, more typically, in a minimally-invasive procedure, to retract member 60 (FIG. 2B). In some preferred embodiments of the invention, the bone slurry may be injected with a needle after member 60 is removed, rather than while member 60 is still inserted.

In a preferred embodiment of the invention, spacer 20 is attached to member 60, for example by a threaded coupler, so at the end of the procedure member 20 is disengaged from spacer 60.

Alternatively, spacer 20 forms an extension of member 60. In a preferred embodiment of the invention, spacer 20 is cut off at or near the point where it enters inter-vertebral space 55, for example using a cutting tool which is inserted inside or over member 60. Alternatively, member 60 is twisted off spacer 20. Preferably, a member 60 is weakened at its connection with spacer 20. It is noted that the un-expanded spacer portions are relatively weak compared to the expanded portions (which may be firmly engaged by bone). Thus, an un-expanded portion of spacer 20 may serve as the weakened connection point. Possibly, member 60 is twisted off spacer 20 (and then any resulting sharp edges may be smoothed off, possibly using a tool inserted through or over member 60). Alternatively or additionally, spacer 20 includes a sleeve which overlaps the weakened connection point. Thus, when member 60 is twisted off, any jagged edges remain covered by the sleeve and do not come into contact with the tissue surrounding the spacer. Alternatively or additionally, after the expansion of the spacer is completed, the jagged end is capped. The cap may be threaded on the end of the spacer. Alternatively or additionally, the cap has the form of a bolt having an end-cap attached to an elongate threaded portion. The elongated threaded portion engages the spacer, possibly at its far end and the end-cap pushes against or engages (possibly using a thread) the near end of the spacer. Other capping mechanism are described below.

Alternatively or additionally, once the spacer is expanded as shown in FIG. 2D, any extraneous spacer portion (i.e., protruding out of inter-vertebral space 55) is cut off. The removed spacer portion may be expanded, partially expanded or non-expanded. In a preferred embodiment of the invention, the cut is made from inside member 20, for example using a rotating cutting edge which is mounted on a narrow elongate member which is inserted inside member 60.

Spacer Size Matching

One consideration in spacer implantation is ensuring spacer 20 fits inter-vertebral space 55. In a preferred embodiment of the invention, a plurality of spacers are available for implantation (for example in a kit), each with a different (compressed) axial length and/or different radial diameter. The require spacer size may be determined from measurements on a CT image or an x-ray image of inter-vertebral space 55. Alternatively, an expandable element may be inserted into the inter-vertebral space and, by the degree of expansion of the element, the size of the space to be filled, and the required spacer geometry, estimated.

Spacer Delivery Direction

In a preferred embodiment of the invention, the surgical approach is from the back of the patient. Alternatively, a lateral or a posto-lateral approach may be used. It is noted that the implanted spacer may be very narrow during implantation, so it is easier to plan an approach and/or use an approach direction that cannot be provided using other fusion devices. Alternatively or additionally, it is noted that the spacer, in some preferred embodiments of the invention, may be made flexible along its main axis, at least in its un-expanded configuration and especially as a result of the slits formed therein. Thus, the spacer can be provided at inter-vertebral space 55 using a curved guide, possibly a bendable guide, such as an endoscope or a catheter. Alternatively, if the spacer is formed of a shape-memory material, the spacer may be cooled below the temperature at which it turns ductile, so that it can be easily bent. Alternatively or additionally, and especially if the spacer is elastic or super-elastic, the spacer is maintained in a curved configuration during insertion using a curved stylet inserted through the spacer, alternatively or additionally to using a curved outer tube. FIG. 2P, below, describes an alternative method of insertion, which utilizes the small-cross-section of the spacer and the flexibility inherent in some expandable constructions, to allow an approach to the vertebrate for a convenient direction.

In a preferred embodiment of the invention, the patient's body is less traumatized, as the spacer is narrow. Alternatively or additionally, the trauma of a prior art anterior is avoided by the use of a narrow spacer or by using a different surgical approach. It should be noted, that there is a wide range of approaches that can be used and even an open surgical incision may be used, still reaping the benefits of not being required (or a lesser requirement) to sacrifice facet joints, muscles, ligament, blood vessels, spinal processes and/or other body structures.

Controlling Spacer Expansion

Figure 2E:
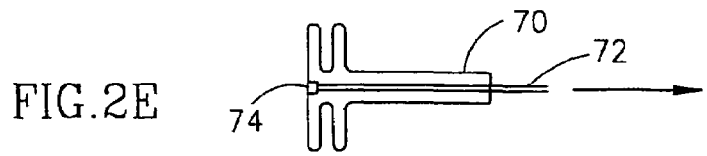
FIGS. 2E-2G illustrate methods of controlling an expansion of a spacer, in accordance with preferred embodiments of the invention.
Figure 2F:
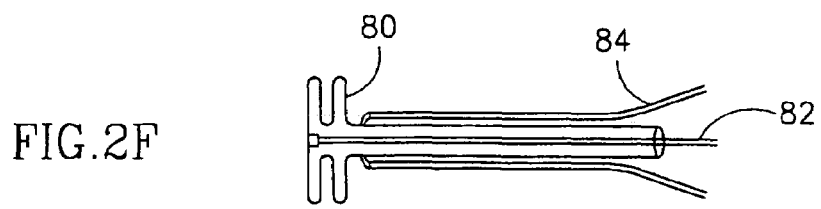
Figure 2G:
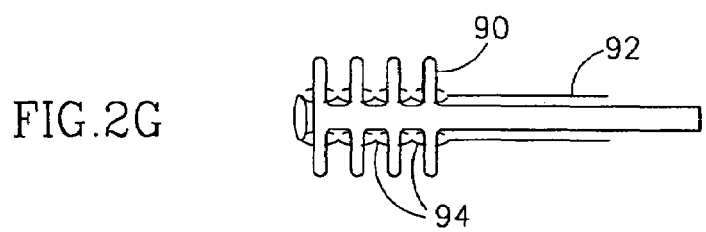
Figure 2H:
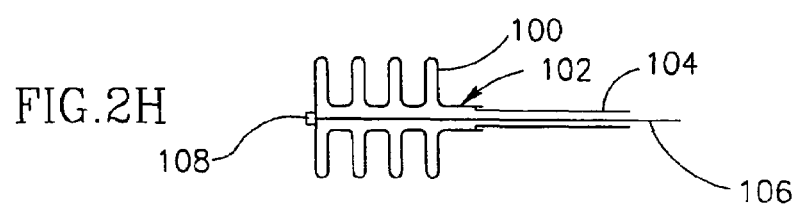
FIGS. 2H-2J illustrate removable and/or adjustable spacers, in accordance with preferred embodiments of the invention.
Figure 2I:
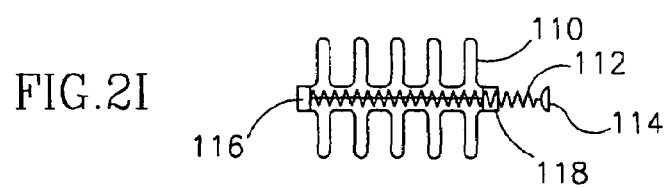
Figure 2J:
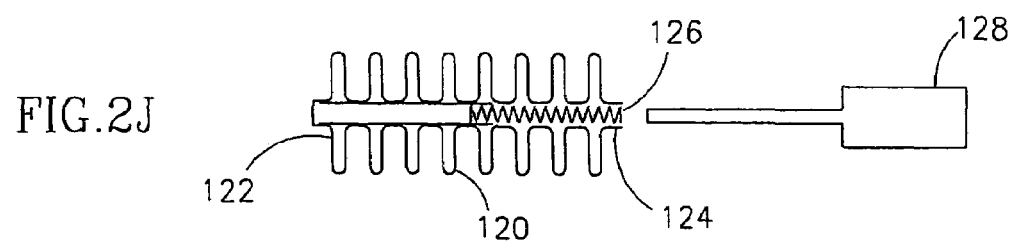

FIGS. 2E-2G illustrate various methods of effecting and/or controlling the expansion of a spacer, in accordance with preferred embodiments of the invention. In FIG. 2E, as shown the expansion is essentially uncontrolled. A spacer 70 is expanded using an expansion member 72 attached to its end-cap 74. When member 72 is moved in the direction of the arrow relative to spacer 70, the resulting stress axially collapses spacer 70, causing the spikes to expand out. The order of expansion of the spikes is dependent, inter alia, on the relative stiffness of the spikes. Usually all the spikes will be about the same stiffness, so the expansion may be gradual over the whole spacer or sudden at points which buckle first. Alternatively, the spacer may be constructed so that some spikes are weaker, by design, than other spikes, so that a certain order of spike extension can be defined.

In a preferred embodiment of the invention, the relative movement of member 72 comprises maintaining member 72 in location relative to the vertebras and pushing spacer 70 towards the end of member 72. Preferably, the relative motion is achieved by direct application of force. Alternative, the relative motion is achieved using a screw action, which can be more gradual and controllable. Threading of the spacer may be anywhere along member 60. However, in some preferred embodiments of the invention, spacer 70 is provided with an inner thread at the end of the spacer opposite from end-cap 74.

In a preferred embodiment of the invention, member 72 is removed from spacer 70 at the end of the expansion process by applying a sudden impulse force to break the connection between the member and end-cap 74. Alternatively, member 72 is twisted off end-cap 74. Alternatively, especially if the relative motion is achieved using a threading of spacer 20, member 72 is coupled to end-cap 74 using a thread which is preferably counter to the threading of the spacer. Thus, member 72 can be screwed off. In some embodiments the end-cap threading is in the same direction as the threading of the spacer.

FIG. 2F illustrates a spacer 80 which is expanded using an internal spacing member 82. However, unlike the example of FIG. 2E, the expansion is controlled, using a collar 84 which does not allow spikes to extend from spacer 80, except at designated areas. Preferably, the designated areas are at the end of collar 84. Alternatively, especially as shown with reference to FIG. 2G, the designated areas may be distanced from the end of the collar. Alternatively or additionally to an external collar 84, spacer 80 may also utilize an internal collar. Preferably, the internal collar engages spacer 80 using an external thread on the collar and/or an internal threading on spacer 80. Alternatively or additionally, no threading is used. possibly, the spacer is expanded by direct pulling and not by a screw-action.

In a preferred embodiment of the invention, movements of an internal collar and an external collar are synchronized to a control the expansion of the spacer. In one example, the spacer is advanced out of the external collar by rotating the external collar relative to the spacer (there is preferably a threaded coupling between them). Thus, the newly "extruded" portion of the spacer is unexpanded and unconstrained. Thereafter or possibly synchronously therewith, the internal collar or a member 72 is retracted, again possibly by rotating it relative to the spacer (preferably utilizing a threaded coupling therebetween), causing axial strain on the spacer, which expands the newly extruded portion. In some embodiments, the internal and external collars may be rotated simultaneously, but each of the collars has a different thread angle relative to the spacer, so each translates a same rotational movement into different axial movements.

In some embodiments, member 72 and/or an internal collar are maintained at a desired angle relative to the spacer using a groove in the member which matches one or more rails and/or a series of protrusions on the inside of the spacer. In some embodiments, the rail, groove and/or protrusions are not arranged in a straight line.

Figure 2K:
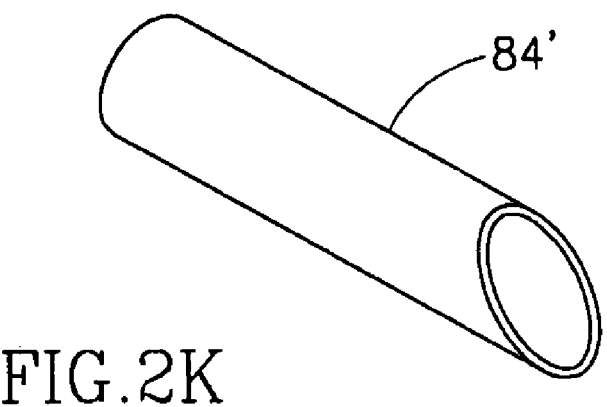
FIGS. 2K-2L illustrate shaped tips for controlling the expansion of a spacer, in accordance with a preferred embodiment of the invention.
Figure 2L:
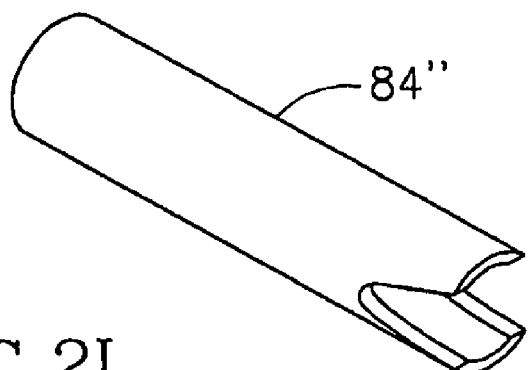
Figure 2N:
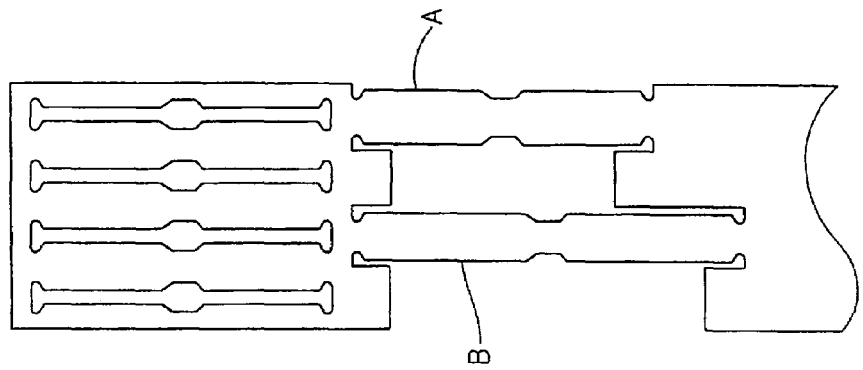
FIG. 2N is a spread layout of a self-bending spacer, in accordance with a preferred embodiment of the invention.

Skipping ahead, FIGS. 2K and 2L illustrate shaped tips for a collar 84, in accordance with a preferred embodiment of the invention. One effect of the shaping is a preferential expansion of one or more spikes (which are unconstrained by the collar) relative to other spikes which are constrained, thereby allowing control of the expansion of the spacer and/or extension of the spikes.

Returning back, FIG. 2G illustrates a spacer 90 whose expansion is controlled using an external framework 92. In a preferred embodiment of the invention, framework 92 includes a plurality of holes 94. When spacer 90 is moved relative to framework 92, spikes can only extend through pre-designated holes 94. The relative motion of the spacer may be achieved using any of the techniques described above. It is noted however that since spacer 90 is pushed against framework 92, there is no requirement for an internal member, in some preferred embodiments of the invention. In some preferred embodiments of the invention framework 92 is left in the body. In a preferred embodiment of the invention, at least some of holes 94, have the form of axial or transverse slots, through which spikes may extend. Thus, in some embodiments, framework 92 comprises tines connected to a collar, the tines defining the above slots, which are open in the direction of the spacer. Such a framework may be retracted after the spacer is expanded.

In a preferred embodiment of the invention, such a framework may be used to control the distortion of a solid member, for example a wire, in which the "expansion" is achieved by a straight element folding into a wavy ribbon shaped element (each spike being a bend in the ribbon). Preferably, a plurality of weakened points, strengthened points and/or areas of increased cross-section are formed along the wire, to limit and/or otherwise control the extent of the wire which is pushed out through holes in framework 92. Thus, the expansion of the spacer, at least for a ribbon-type spacer, can be made independent of the axial length of the spacer.

Alternatively or additionally, the expansion of the spacer may utilize a balloon (not shown) which is inserted in the lumen of the spacer and, when expanded, radially extends the spikes. Generally, the "ring" segments of the spacer are not affected by the balloon. Possibly, the balloon includes a plurality of fingers, that push out the spikes, but do not affect the "rings". Alternatively or additionally, the ring segments may also be deformed by the balloon. In one example, the ring segments comprises a mesh material, which can expand, but not as much as the spikes. In a preferred embodiment of the invention, the ring segments plastically deform at a greater applied force level than the spikes, so that the spikes extend out before the rings are deformed.

Exemplary Spacer Expansion

Figure 13A:
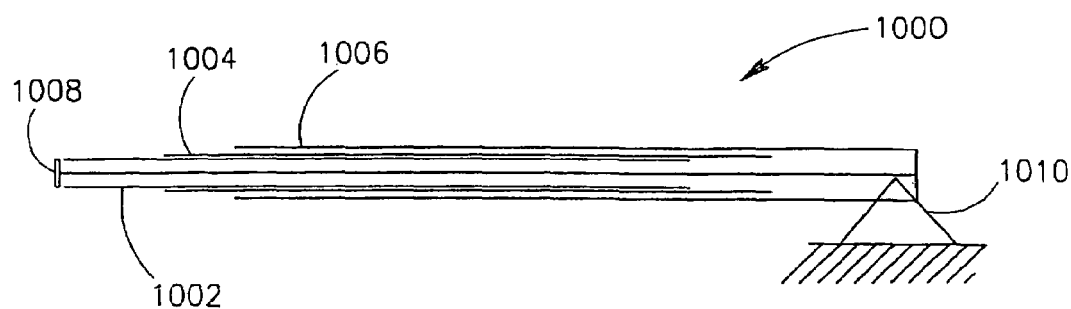
FIGS. 13A-13C illustrate a method of controlling the expansion of a spacer, in accordance with a preferred embodiment of the invention.
Figure 13B:
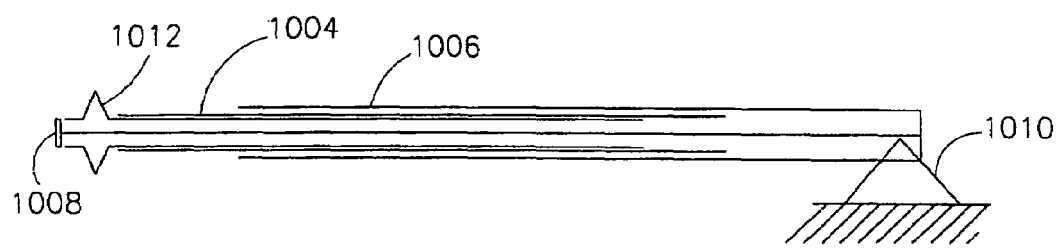
Figure 13C:
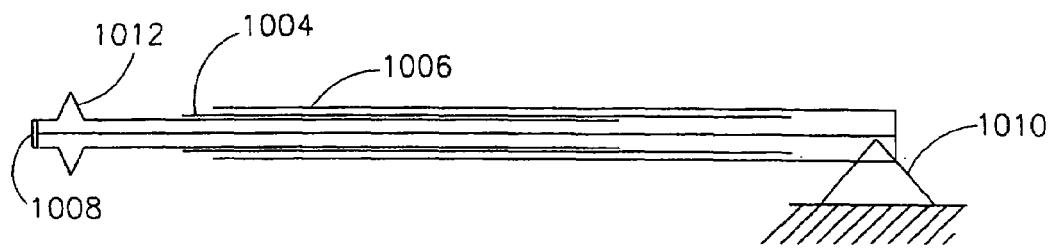

FIGS. 13A-13C illustrate an exemplary method of spacer expansion, in accordance with a preferred embodiment of the invention. A spacer 1002 is provided as a tube having an inner bolt 1008, which bolt preferably prevents the advance of the end of spacer 1002, past the bolt. An outer collar 1004 is provided for shaping the expansion of the spacer. A laproscopy tube 1006 is also shown. In this embodiment, both bolt 1008 and tube 1006 are fixed to a base 1010 outside the body. This base may be, for example, fixed to the patient and/or his bed or it may be prevented from advancing towards the body.

FIG. 13A shows a starting position, with bolt 1008 and spacer 1002 (in its unexpanded state) extending between two vertebrae (not shown).

Both spacer 1002 and collar 1004 are advanced. However, as the spacer is prevented from advancing by bolt 1008, it expands, at the areas where expansion is not prevented by collar 1004, forming one or more spikes 1012. This result is shown in FIG. 13B.

Collar 1004 is then retracted (FIG. 13C), so that both the collar and the spacer can be advanced again.

Spacer Removal

In some cases, it may be necessary to adjust the length of the spikes after the spacer is inserted, possibly even a few days after the spacer insertion procedure is completed. Also, if the spacer is incorrectly implanted, for example, as evidenced by x-ray images, it may be necessary to remove the spacer. In accordance with preferred embodiments of the invention, the spacer can be adjusted and/or removed.

In a preferred embodiment of the invention, removing the spacer comprises un-expanding the spacer so that it has a narrow diameter and then removing the spacer. Typically, the process of un-expanding the spacer extends the axial length of the spacer, so that some of the spacer may be "self-removing". Preferably, an end of the spacer is restricted in motion, so that it does not move, while moving another end away from the restricted end. Alternatively or additionally, the another end of the (axially extending) spacer is guided so that it does not impact on sensitive tissues.

The tension of a spacer may be varied by increasing (or decreasing) the spike length, thereby pressing with a greater (or lesser) force against surrounding bone tissue. Alternatively, the tension may be increased by adding resilient material into the spacer or the inter-vertebral space, preferably using a needle. In one example, shown with reference to FIG. 4E, a second spacer (142) is inserted into a first spacer (144). Decreasing the spike length may increase the length of the spacer by an unacceptable amount. Preferably, the extra length of the spacer is cut off and removed from the body.

Control of Spacer Characteristics

In a preferred embodiment of the invention, one or more of the following three characteristics of the spacer should be independently controllable: spacer axial length, spike length and spike tension. In some embodiments, these characteristics are controlled by selecting, for insertion, a particular spacer from a set of available spacers. In other embodiments, a spacer may be adapted to have the desired characteristics, for example, length can be controlled by not expanding the entire spacer, and cutting off the un-expanded portion. Additionally, in some embodiments of the invention, it is desirable to modify the characteristics of a spacer after it is inserted. Thus, allowing a spacer to be maintained at—or modified to—an optimal operating configuration while inside the body.

In some cases, what is desired is a modification of the spacer length, with any associated change in tension or spike length being undesirable or ignored. As described above, the tension in a spacer may be increased by inserting a second spacer.

FIGS. 2H-2J illustrate various methods of modifying geometrical and/or tensile characteristics of a spacer, after it is expanded. A trivial type of modification is removing the spacer and optionally inserting a new spacer or the same spacer after it is modified. In a preferred embodiment of the invention, removing a spacer includes collapsing the spacer and then removing the resulting narrow-diameter tube.

FIG. 2H illustrates a spacer 100, which is further expanded or collapsed using a maintaining member 106 and a grasping member 104. In essence, member 104 engages one end of spacer 100 and member 106 engages a second end of spacer 100. When the two members are moved relative to each other, the spacer is expanded or un-expanded. In a preferred embodiment of the invention, maintaining member 106 engages an end-cap 108. The engagement may be simple contact, fitting member 106 into a depression in end-cap 108 or a threaded connection. Grasping member 104 preferably grasps spacer 100 at its near end 102, preferably using an internal threaded connection on end 102. Alternatively, an external connection to end 102, possibly a threaded connection may be used. In a preferred embodiment of the invention, when modifying spacer 100, member 106 is maintained in place, so that end-cap 108 does not advance into the body.

FIG. 2I illustrates a spacer 110 which is un-expanded (or completely collapsed) by the insertion of a screw or a bushing 112 into the spacer. Alternatively, the screw remains in the spacer when the spacer is inserted. Screw 112 engages a threaded end 118 and an end-cap 116. When the screw is turned, the spacer is un-expanded. In a preferred embodiment of the invention, the screw is inserted using a syringe, possibly forming a needle of the syringe. Alternatively, the screw is engaged at a head 114, using an inserted screw-driver.

In a preferred embodiment of the invention, screw 112 is inserted into the spacer using a needle. In a preferred embodiment of the invention, the screw is screwed into the spacer. Alternatively, the near spacer end-cap has the form of a keyhole with a larger diameter portion through which the screw can be inserted and a smaller diameter portion which the screw can engage. Optionally, instead of the far end-cap engaging the screw, it only acts as a stop against which the screw can push.

In a preferred embodiment of the invention, the inner lumen of the spacer includes a threading and/or protrusions which the screw can engage. Optionally, the protrusions are created by the expansion of the spacer. Additionally or alternatively, the protrusions form a guide which guide an inserted needle of screw through the spacer to its far end-cap, resisting deviations which would make the needle/screw exit the side of the spacer. Preferably, this type of guidance is provided when the spacer has a bent configuration inside the body.

In a preferred embodiment of the invention, the near end-cap of the spacer includes a flared opening to ease the insertion of a screw, needle or screw driver head into the spacer and/or to engage the end cap. Additionally or alternatively, a guiding mechanism may be provided, for example, a magnetization of the end cap and a corresponding magnetic sensor on the inserted object or an ultrasonic transducer. Additionally or alternatively, a wire guide remains attached to the spacer after it is inserted and an endoscope or other inserted object may be guided to the spacer by following the wire. Optionally, the one end of the wire exits the body. Additionally or alternatively, the wire's end is easily identifiable, for example, by having a large radius ball attached thereto.

FIG. 2J illustrates a spacer 120 having an integral expansion control mechanism. An internally threaded tube 122 is provided in conjunction with an externally threaded screw 124. When an end-cap 126 of the screw is rotated, the screw moves relative to the tube and the spacer expands or un-expands. Alternatively, the tube may be rotated and the screw is fixed (i.e., the tube is rotatable relative to the spacer and the screw is fixed to the spacer, at least with respect to its rotation). A screwdriver 128, or at least its tip is preferably inserted until the screw. Alternatively, spacer 120 may include a ratchet mechanism, whereby a member 124 may be pushed into a holder 122, but it cannot move back out (or vice-versa). In this case, a grasper, such as grasping member 104 (FIG. 2H) is preferably provided so that motion of spacer 120 can be controlled.

In one preferred embodiment of the invention, the interior of spacer 120 provides the function of tube 122 (or of a holder 122), preferably being pre-threaded. In some embodiments, tube 122 is open at both ends or has holes defined therein, to aid in expelling any material which may have accumulated in its lumen. Alternatively or additionally, the diameter of screw 122 is small enough so that it does not fill the entire inner cross-section of tube 122.

In a preferred embodiment of the invention, screw 124 is inserted after the expansion of spacer 120 is completed, preferably as part of the insertion procedure. Alternatively, screw 126 may be inserted after the fact, for example when it is decided that adjustment may be desirable. Alternatively, screw 124 may inserted to complete the expansion of spacer 120, during its original expansion.

In a preferred embodiment of the invention, the modification of the expansion of spacer 120 may be controlled by inserting an internal or external collar or a framework, as shown in FIGS. 2F-2G. Thus, it is possibly to modify the spike length for only part of the spacer (for example the middle or the ends) and/or to compensate for increased axial length of one part of the spacer by extension of spikes at another part of the spacer. Alternatively or additionally, the threads and/or "end-caps" described with reference to FIGS. 2E-2J may be located in other parts of the spacer than its ends.

In a preferred embodiment of the invention, the "minimum diameter" lumen of the spacer does not change when the spacer is expanded or collapsed. Alternatively, the lumen may decrease, for example, if portions of the tubes fold into the lumen rather than outside like spikes.

Spacer Deformation Process

In a preferred embodiment of the invention, the spacer is expanded and collapsed using plastic deformation of the spacer material, whereby the tube is plastically deformed to form the expanded spacer. Alternatively, at least one of the expansion or collapsing uses elastic, super elastic or shape-memory properties of the material. In one example, the spacer is formed so that it is partially expanded and then elastically deformed to be completely collapsed prior to insertion. Thus, when the expansion starts, some or all of the spikes protrude from the spacer and increased axial force on the spacer will only urge the spikes further out and not in. It is noted that some parts of the spacer may be designed to fold in, these parts may be elastically deformed away from their "interior position", prior to inserting the spacer. FIG. 6XIA-6XLB, described below, illustrate weakening portions of the spacer to control the shape of the extended spike.

Alternatively or additionally, the spacer utilizes super-elastic properties of the material it is composed of. In one example, the spacer expands by itself to the expanded configuration, what is required is to limit that expansion until such expansion is desired. Such limitation may be achieved by maintaining an axial length of the spacer or by providing an external restraining tube which maintains the spacer in a collapsed configuration. Alternatively, the axial length may be maintained using an internal screw which engages the spacer over substantially its entire length. In one embodiment, as the spacer is advanced out of the restraining tube (or the screw), the unrestrained portion of the spacer expands and/or engages the surrounding bone tissue.

In another example, the spacer collapses by itself to the collapsed configuration, unless otherwise restrained, for example by a screw as described above and with reference to FIGS. 2I and 2J. Additionally or alternatively, the spacer is maintained in shape using an interlock mechanism, preferably a ratchet-type mechanism. For example, in the embodiment of FIGS. 8Ai and 8Aii (described below) two tabs may butt or overlap. If one tab includes a protrusion and the other tab includes a recess, when the tabs overlap, the protrusion engages the recess and a ratchet mechanism is formed. Additionally or alternatively, a dedicated ratchet mechanism may be formed by a barbed elongated internal member of the spacer which is connected at one end to the spacer and which engages a different part of the spacer using the barbed other end.

Alternatively or additionally, the expansion and/or collapsing may be partly super-elastic and partly plastic or elastic.

In a preferred embodiment of the invention, the super-elasticity is achieved by constructing the spacer of a shape-memory material, such as NiTi. Preferably, the material's state transition temperature is set to be about 30° C., so that the spacer does not naturally pass through a transition after it is already implanted.

In some preferred embodiments of the invention, the spacer is collapsed by cooling it. In one embodiment, the spacer is formed of a shape-memory material which is cooled to make it pliable and then the spacer is collapsed as described above.

In another embodiment, the spacer is formed of a super-elastic portion and a shape memory portion, with the (stronger) shape memory portion maintaining it in an expanded configuration and a super elastic portion applying forces to return to a collapsed configuration. Possibly, two types of shape memory material are provided, each with a different transition temperature. In a preferred embodiment of the invention, when the spacer is cooled, the shape-memory portion applies a weaker force and the spacer collapses. Possibly, only a ratchet mechanism portion is formed of a shape memory material and a super elastic material, with the rest of the device being formed of a super-elastic material.

In a preferred embodiment of the invention, the entire spacer comprises a single type of material—plastically deformed, elastically deformed, super elastic or shape memory. Alternatively, the spacer comprises multiple layers of material, each with different properties. Alternatively or additionally, different parts of the spacer may have different mechanical properties and/or be formed of different materials. In one example, the ring segments are plastic and the spikes are elastic. In another example, different spikes may have different elasticity properties. In another example, one side of the spacer may have one property and another side of the spacer may have a different property.

Spacer End Cap

In some preferred embodiments of the invention, the end-cap protrudes from the spacer after it is expanded (as does end cap 108 in FIG. 2H). In some cases, the end cap may include a spike to engage bone tissue. Alternatively, the end cap may be formed to be within a plane defined by the end-most spikes. In one example, this is achieved by pre-folding the end-cap into the spacer. Alternatively, the end-cap may be folded into the spacer as part of the expansion process, for example (with reference to FIG. 2E), inverting end-cap 74 by pulling on member 72. Alternatively, the end-cap may be manufactured to elastically fold into the spacer. Alternatively, the deformation of the end spikes may fold the end-cap into the spacer. Additionally or alternatively, the end-cap may be retracted after the expansion of the spacer by pulling of a screw which engages the end-cap. Skipping ahead, FIGS. 2OA-2OC illustrates a spacer in which the end-cap is formed to be inside the spacer, so that the expanding spikes reach all the way to the end of the spacer.

End-Cap Locking

Referring to FIG. 2I, in some embodiments, bolt 112 is not threaded onto spacer 110, however, once the spacer expansion is completed, the bolt is preferably locked to spacer 110, for example at its end cap 118, not necessarily using threading.

Although FIG. 13A shows that spacer 1002 and bolt 1008 extend all the way from inside the body to an external base 1010, In a preferred embodiment of the invention, the bolt and the spacer are considerably shorter. Instead, spacer 1002 is advanced using a pusher and bolt 1008 is restrained from advancing using a pole element.

Many mechanisms may be used for locking the spacer and its bolt. In a preferred embodiment of the invention, however, the locking mechanism includes one or more of the following features:

(a) retracting a spacer holding mechanism causes a locking of the spacer;

(b) advancing a spacer holding mechanism, especially by threading, causes a locking of the spacer;

(c) the mechanism is primed for locking only when the spacer expansion is complete; and/or (d) the locking mechanism is plastic (i.e., by deformation) or elastic (i.e., a restraint is released that allows the mechanism to lock).

Although the following locking mechanisms are shown as being independent, in some embodiments, features from one locking mechanism may be combined with features from another locking mechanism, for example, the mechanism may combine fins on a spacer and fins on a bolt in a same spacer device.

Locking Fins Embodiment

Figure 14A:
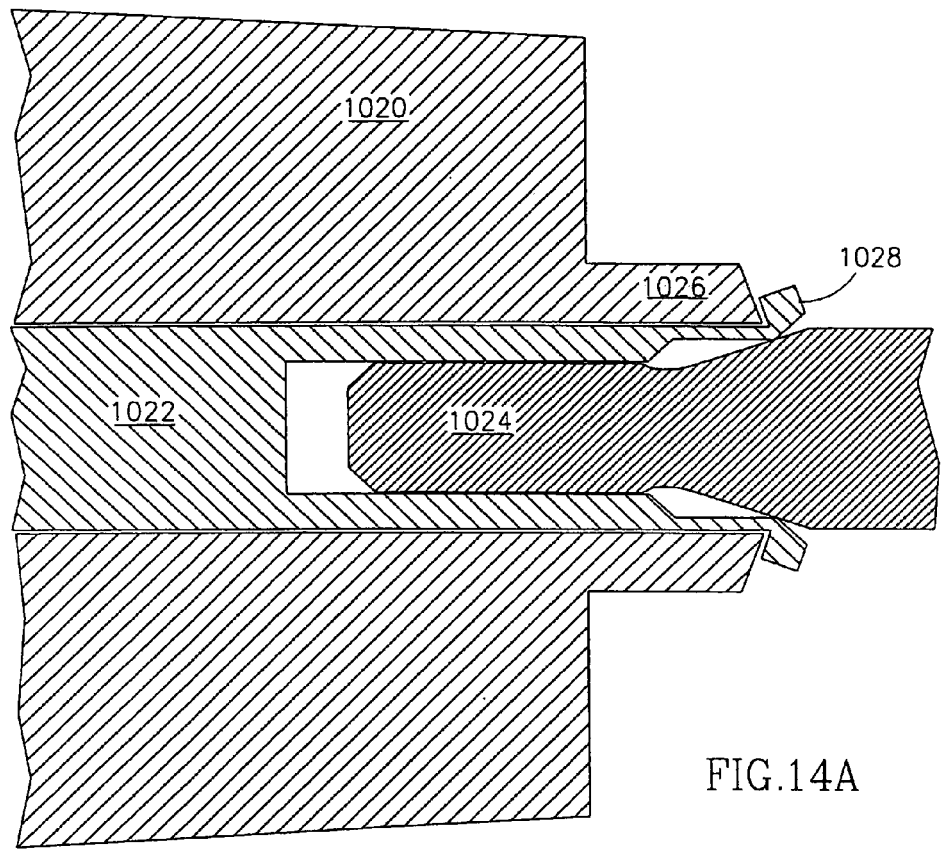
FIGS. 14A and 14B illustrate a fin based locking mechanism in which one or more locking fins spring out from a bolt to engage a spacer, in accordance with a preferred embodiment of the invention.
Figure 14B:
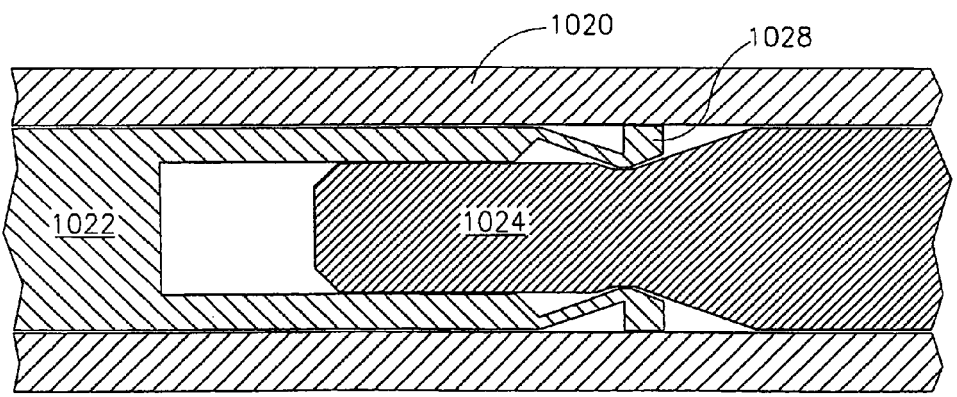

FIGS. 14A and 14B illustrate a fin based locking mechanism in which one or more locking fins spring out from the bolt to engage the spacer, thereby preventing it from collapsing. In other embodiments, for example as shown below, the bolts are plastically deformed and/or at least some of them may be provided from the spacer, to engage the bolt.

FIG. 14A illustrates an expanded spacer 1020, schematically shown, and having an inner bolt 1022.

A plurality of fins 1028 are shown extending from bolt 1022 and engaging an end-cap 1026 of spacer 1020. In this embodiment, end-cap 1026 has inclined edges, for better engagement by fins 1028. Fins 1028 are preferably extended using a plastic, super-elastic or shape-memory extension mechanism, however, other mechanisms may be used instead. A pole element 1024 is shown retracting from bolt 1022.

FIG. 14B shows spacer 1020 in an unexpanded state, in which fins 1028 are restrained from expanding by spacer 1020 and also prevent pole 1024 from retracting from bolt 1022, by engaging pole 1024 in depressions formed therein.

Referring back to FIG. 14A, pole element 1024 may be advanced to ensure the complete extension of fins 1028 against end-cap 1026. It is noted that the fins can so extend only if the spacer is sufficiently axially contracted, since otherwise it is within the cage. Furthermore, once the fins extend, pole element 1024 can be removed.

In some preferred embodiments of the invention, spacer 1020 is removed using a device that radially compresses the fins, so that the bolt is unlocked from the spacer, thereby allowing it to collapse.

In this and other embodiments, fins 1028 are preferably proximal from the spacer portions where the spikes expand, to prevent the fins from being engaged by the spikes. Alternatively or additionally, the fins may be wider than the spikes. Alternatively or additionally, the fins may be located at an angular offset from the spikes, so they do not engage them. Alternatively, the fins may be extended to engage the spacer at positions other than its end, for example, by providing an end-cap having a plurality of axially spaced fin-engaging locations along it or by allowing the fins to engage an inner thread of the spacer or the spikes (from inside the spacer).

Plastically Distorted Fins Embodiment

Figure 15A:
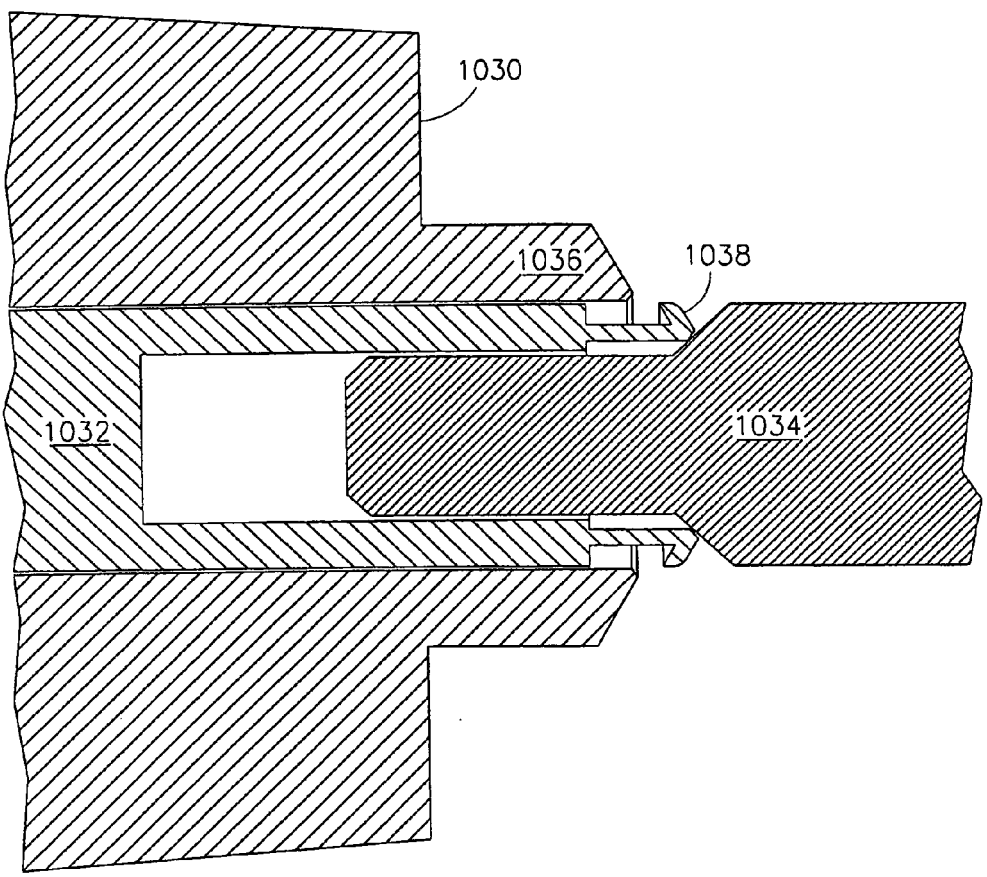
FIGS. 15A and 15B illustrate a locking mechanism similar to that of FIGS. 14A-14B, utilizing plastic deformation, in accordance with a preferred embodiment of the invention.
Figure 15B:
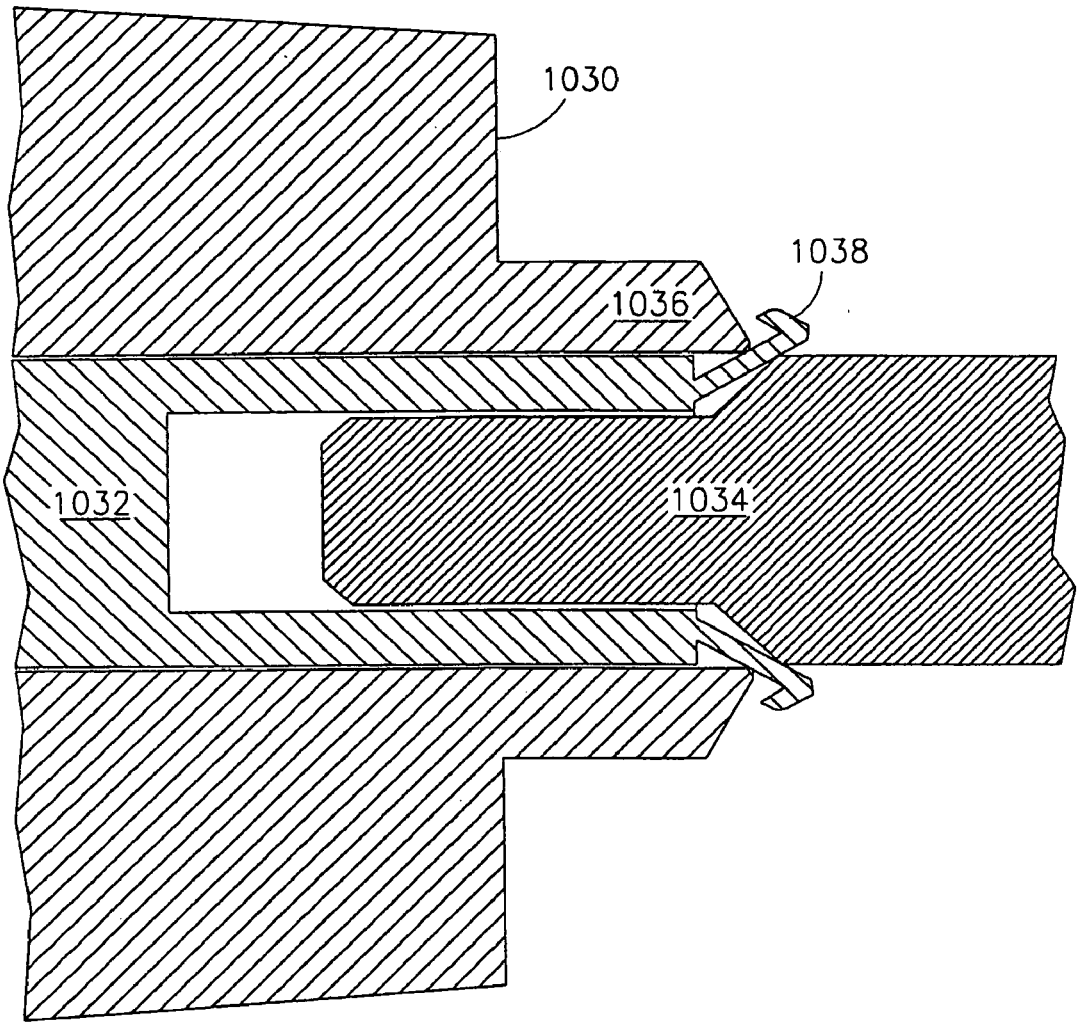

FIGS. 15A and 15B illustrate a locking mechanism similar to that of FIGS. 14A-14B, except that it utilizes plastic deformation. A plurality of fins 1038 are extended from a bolt 1032 to lock against an end-cap 1036 by advancing a pole element 1034 towards bolt 1032, thereby plastically deforming the fins to engage the end-cap. Preferably, pole element 1034 is threaded to match a threading in bolt 1032 and pole element 1034 is advanced by rotation. The pole may be retracted by unscrewing it. Alternatively, the threading may be extend along only a portion of the circumference so that when a half turn is completed, pole element 1034 is released from the threading.

Distorting Ring Embodiment

FIGS. 16A-16F illustrate a locking mechanism utilizing an expanding flange, in accordance with a preferred embodiment of the invention.

Figure 16A:
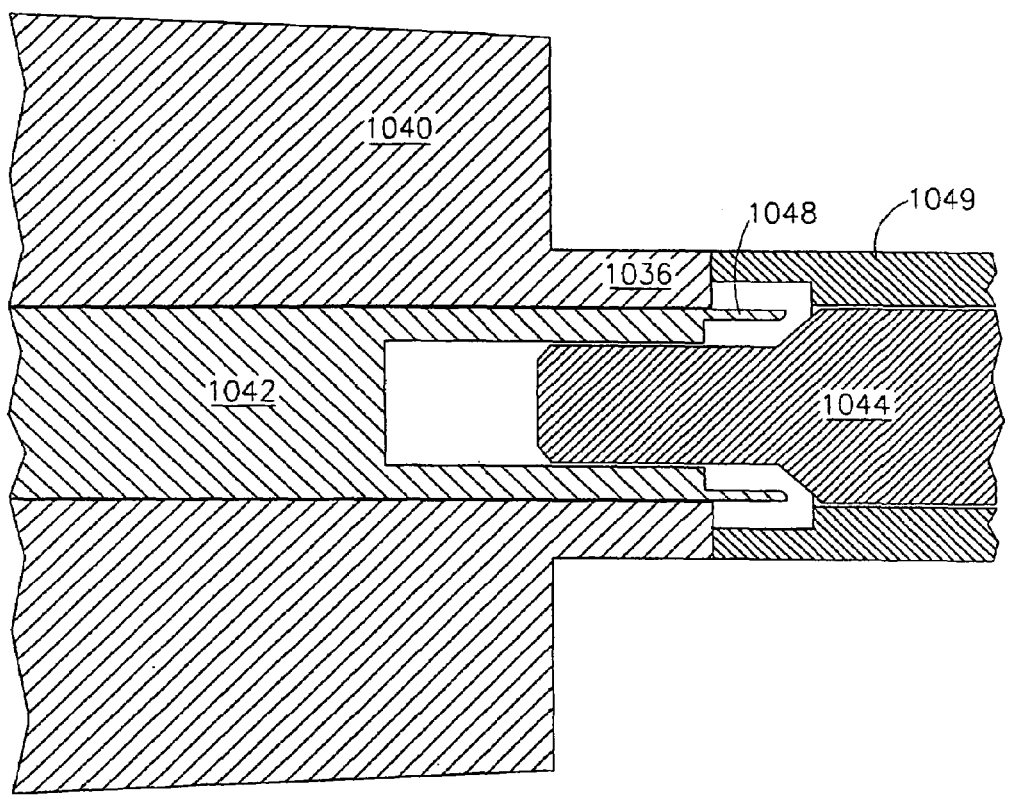

FIG. 16A shows a spacer 1040, prior to it being locked to a bolt 1042, by a flange 1048 of the bolt. A pole element 1044 preferably engages bolt 1042, for example by being threaded thereto.

Figure 16B:
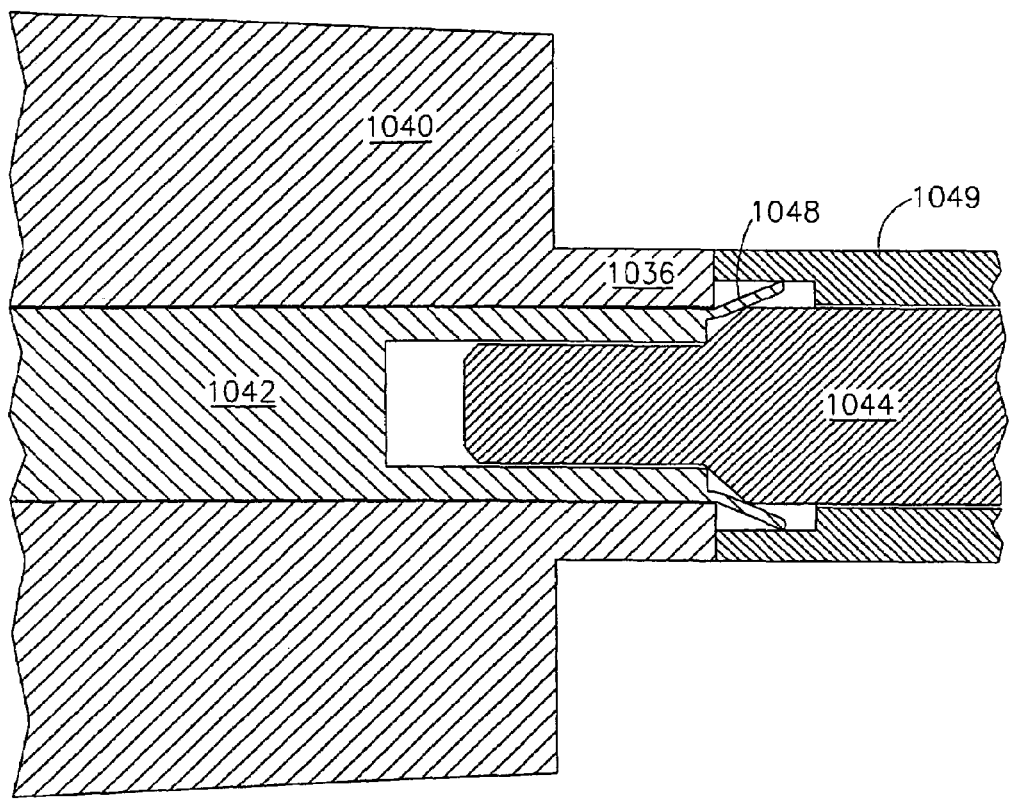

In FIG. 16B, pole 1044 is advanced relative to bolt 1042, thereby expanding flange 1048 so that it is wider than an aperture defined by an end-cap 1036, so the spacer cannot retract from the bolt.

FIG. 16C is a blow-up view of a pushing tube 1049, showing a projection 1047 formed at the end of the tube, for engaging a matching notch in spacer 1040. The matching projection and notch allow maintaining and controlling the angular orientation of spacer 1040, inside the body, using pushing tube 1049.

FIG. 16D is a diagram showing details of the construction of pole element 1044.

Figure 16E:
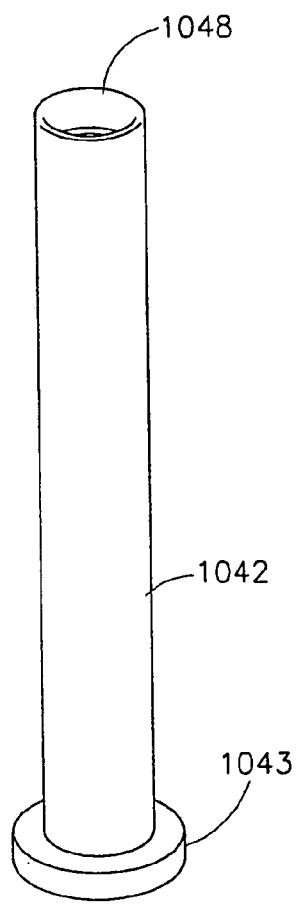

FIG. 16E is a perspective view of bolt 1042, showing a wide base 1043, which prevents the advance of spacer 1040 past the bolt, when the spacer is advanced as shown in FIGS. 13A-13C.

Figure 16F:
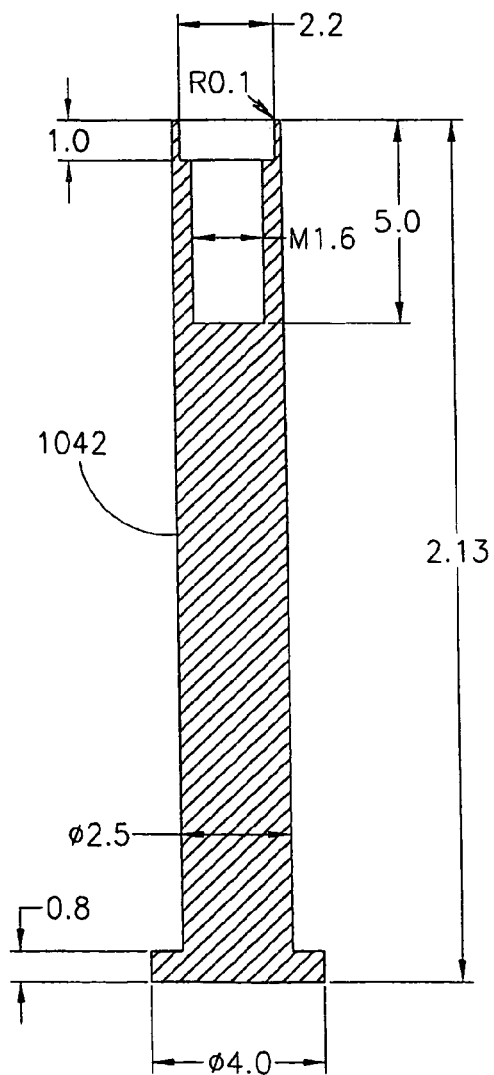

FIG. 16F is a diagram showing details of the construction of bolt 1042.

Fins on Spacer Embodiment

Figure 17A:
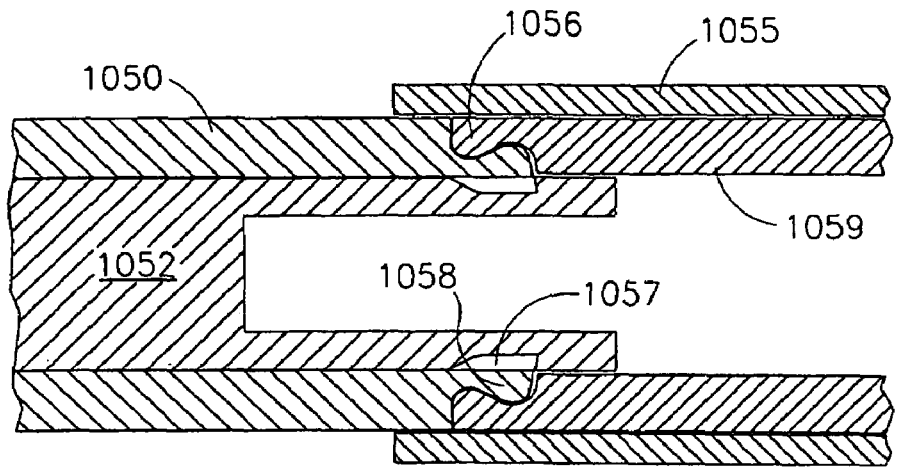
FIGS. 17A-17C illustrate an alternative locking mechanism in which fins on a spacer engage a bolt inside of the spacer, in accordance with a preferred embodiment of the invention.
Figure 17B:
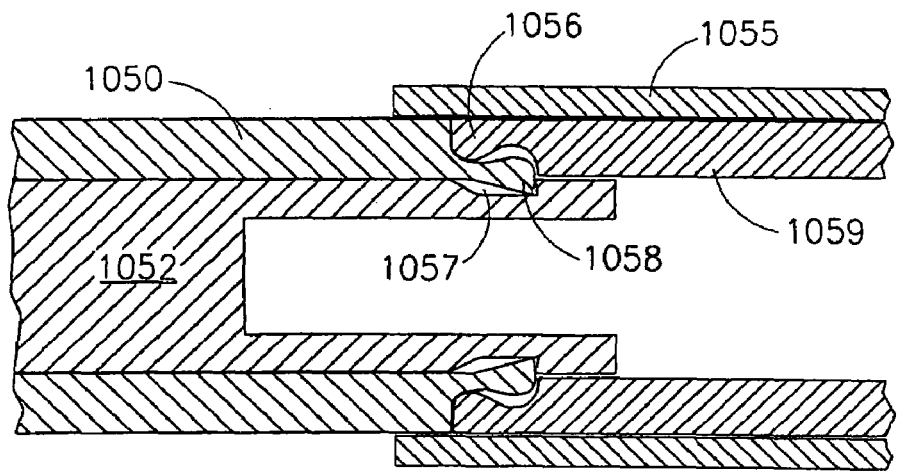
Figure 17C:
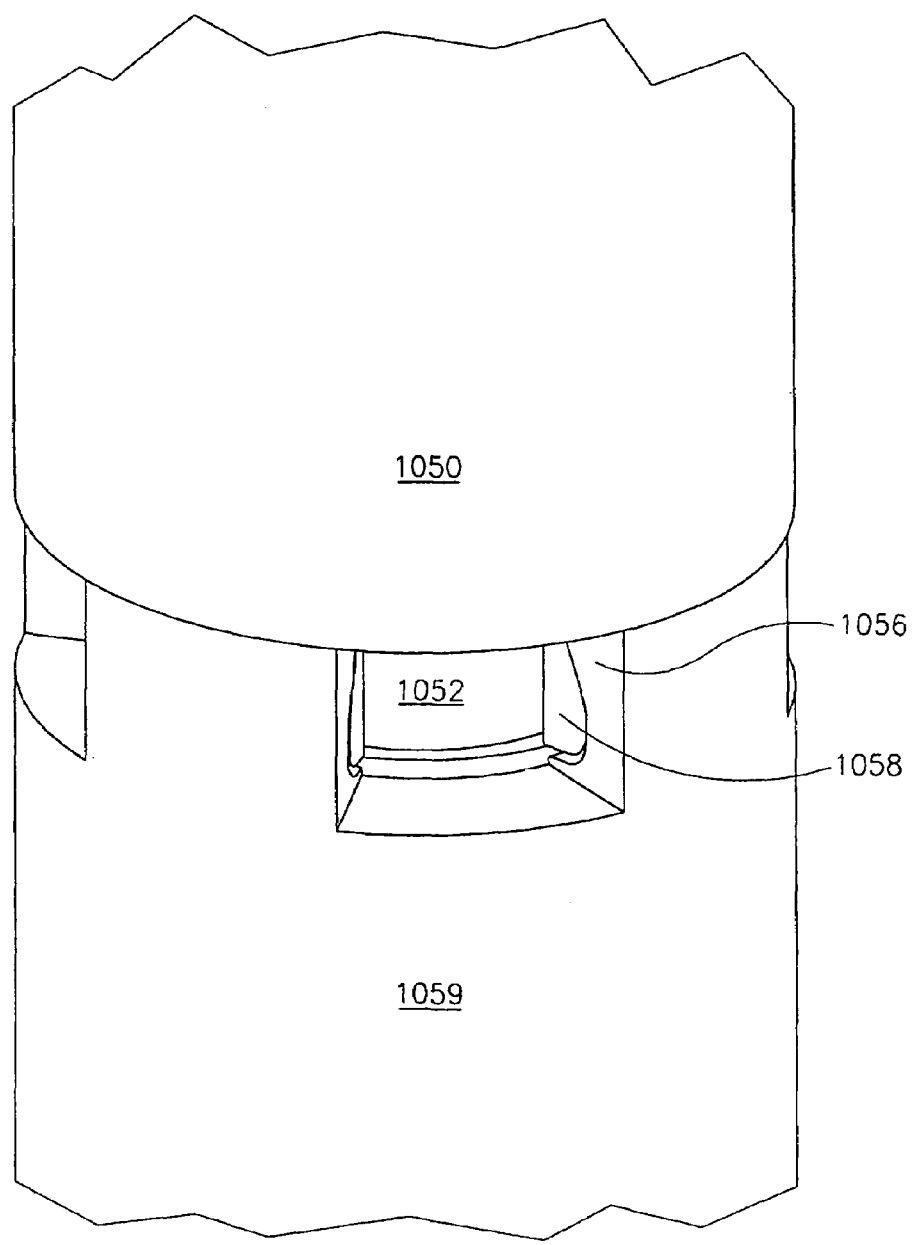

FIGS. 17A-17C illustrate an alternative locking mechanism in which fins on a spacer engage a bolt inside of the spacer. FIG. 17A shows the configuration prior to activation of the locking mechanism. A spacer 1050 has a plurality of fins 1058 formed at its end. A bolt 1052, inside the spacer, comprises one or more depressions 1057, which may be formed as a band around bolt 1052. A pushing tube 1059 includes inwardly protruding tips 1056, which engage fins 1058 when the fins are not in depressions 1057. Thus, pusher tube 1059 does not slip off spacer 1050.

When the spacer is contracted sufficiently, fins 1058 will match up to depressions 1057. By retracting pusher 1059, protrusions 1056 will urge fins 1058 into depression 1057, locking bolt 1052 against spacer 1050. Preferably, this motion of fins 1058 will also simultaneously free, pusher 1059 to be retracted, however, this is not essential. In a preferred embodiment of the invention, a sleeve 1055, possible the laproscopic tube 1006 is provided to insure that fins 1058 bend in, rather than protrusions 1056 bending out. Optionally, a plurality of axially spaced depressions 1057 is provided, to allow for various expansion geometries of spacer 1050, FIG. 17B shows the configuration after the activation of the locking mechanism.

FIG. 17C is a perspective view of the configuration of FIG. 17A, without the sleeve.

Pull-Out Locking Mechanism

FIGS. 18A-18D illustrate a locking mechanism in which fins on a bolt are extended when a pole element of the bolt is retracted, in accordance with a preferred embodiment of the invention.

Figure 18A:
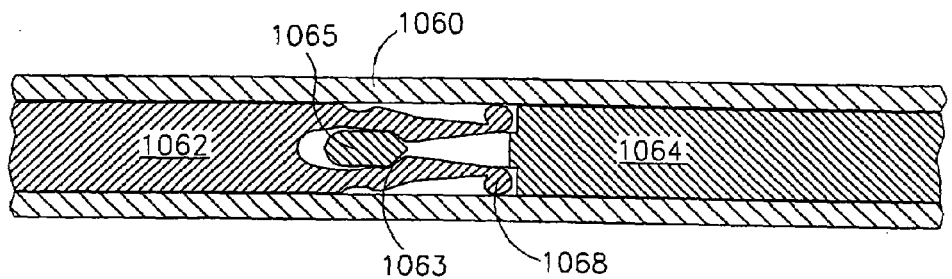
FIGS. 18A-18D illustrate a locking mechanism in which fins on a bolt are extended when a pole element of the bolt is retracted, in accordance with a preferred embodiment of the invention.

FIG. 18A shows a spacer 1060 in an unexpanded configuration. An extension 1065, of a pole element 1064, is held by a plurality of inwardly bent fins 1068 of a bolt 1062. Extension 1065 contacts and is axially constrained by a surface 1063 of the fins. Fins 168 are maintained in an inwards configuration by spacer 1060.

Figure 18B:
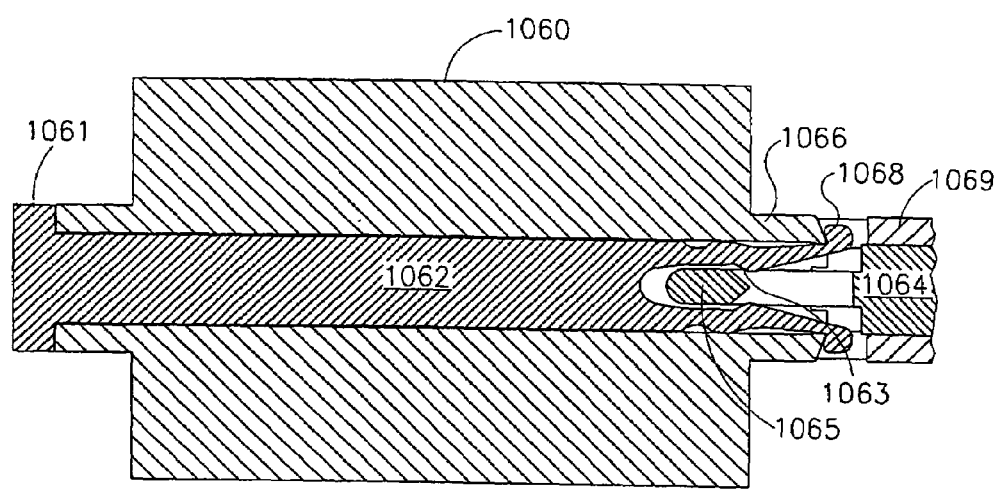

In FIG. 18B, the spacer is sufficiently axially contracted, that fins 1068 can extend over an end-cap 1066 of spacer 1060. This extension may be elastic, super-elastic or shape-memory based. Alternatively, when pole 1064 is retracted relative to a pusher 1069, extension 1065 is urged against surface 1063 of fins 1068, causing fins 1068 to extend out and engage end-cap 1066.

Alternatively to the fin design shown in which surface 1063 is far from the tip of the fins, surface 1063 may be closer to the tips of the fin, thus requiring less force to extend the fins, if the base of the fin (generally the part that bends) is not also advanced towards the tips of the fins. This may result in a longer extension 1065 than shown.

Figures 18C, 18D:
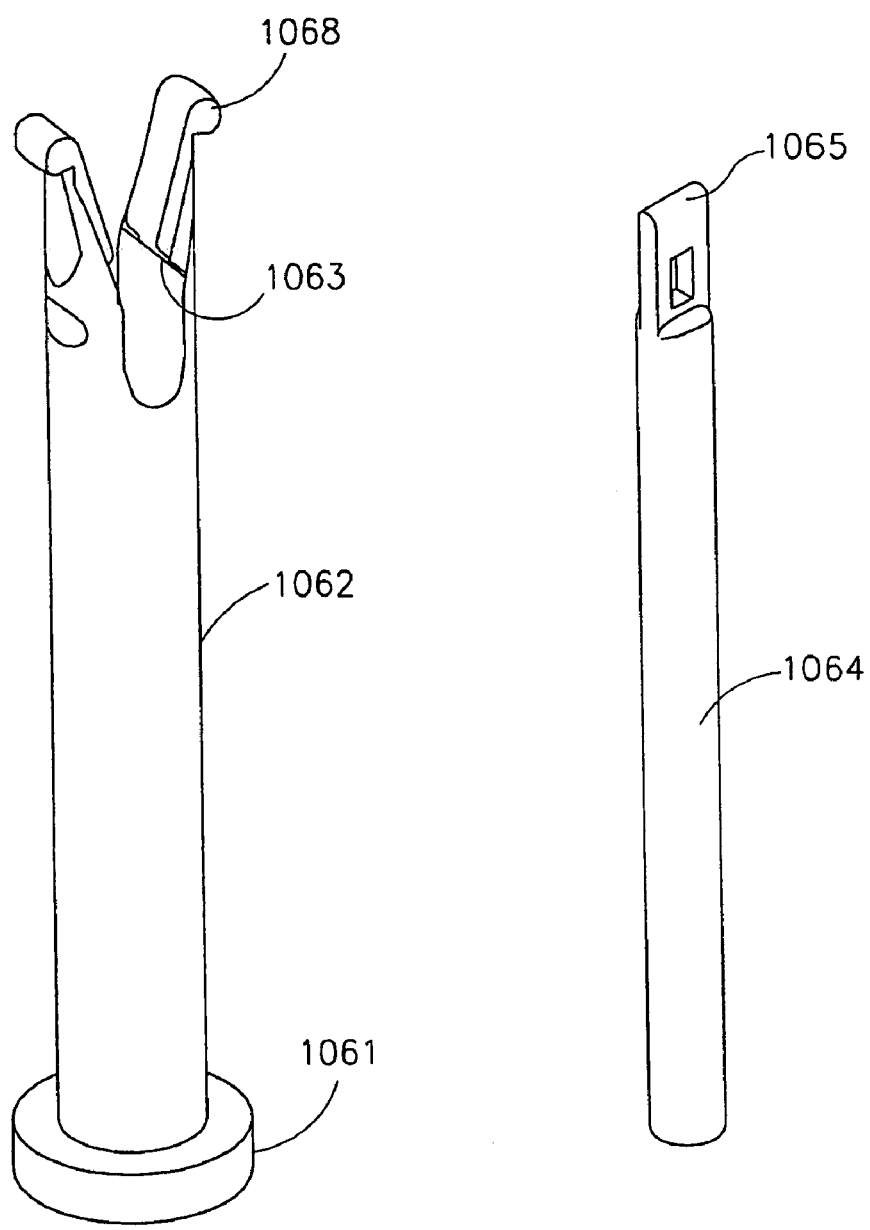

FIG. 18C is a perspective view of bolt 1-062, showing also its base 1061.

FIG. 18D is a perspective view of pole element 1064, showing a preferred attachment method between extension 1065 and the rest of pole 1064.

Ring Locking Embodiment

Figure 19C:
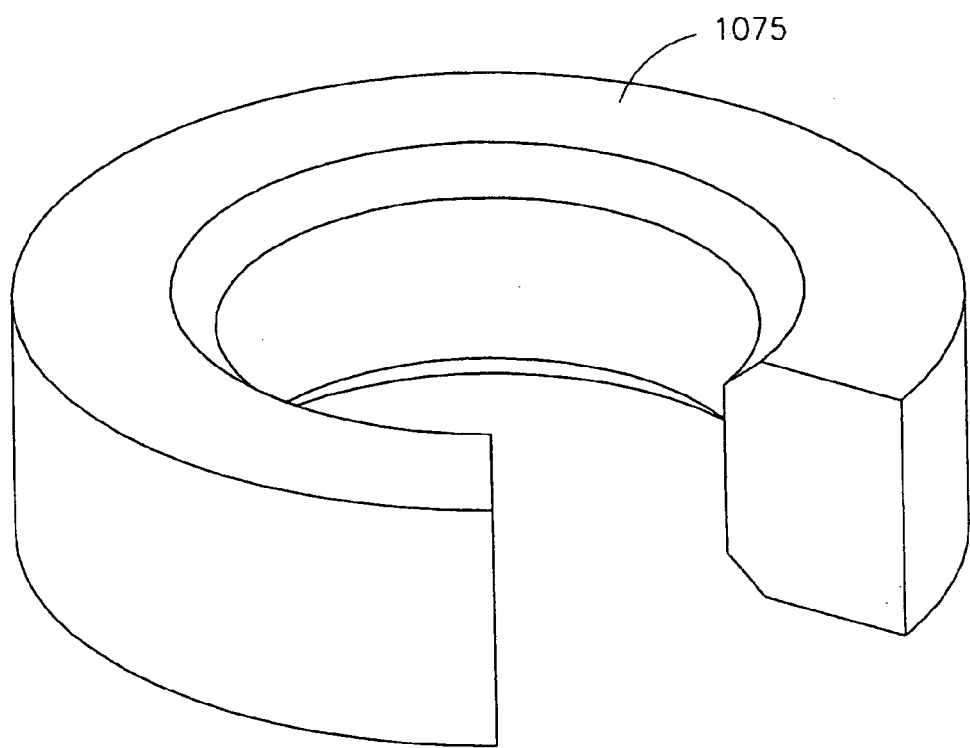

FIGS. 19A-19C illustrate a ring-based locking mechanism, in accordance with a preferred embodiment of the invention. A cage 1070 and a bolt 1072 are locked together using a ring 1075, that matches a groove 1077 formed in bolt 1072, thereby locking the bolt against an end-cap 1076 of spacer 1070.

In FIG. 19A, the spacer is unexpanded. As a pusher 1079 is advanced, spacer 1070 axially contracts and radially expands. Concurrently ring 1075 is advanced towards spacer 1070.

In FIG. 19B, ring 1075 contracts into groove 1077, thereby locking the spacer.

FIG. 19C illustrates an exemplary ring 1075, which is preferably formed of a super-elastic material, such as Nitinol, however, this is not required.

Tube Cross-Section

In a preferred embodiment of the invention, the cross-section of tube 22 (FIGS. 1A-1D) is circular. Alternatively, other cross-section are used, for example, polygon cross-sections, such as a triangle or a square. Preferably, the spikes are formed on sides of the polygon. Alternatively or additionally, they are formed at vertexes of the polygon. In a preferred embodiment of the invention, the inner cross-section of the tube and the outer-cross-section of the tube have the same geometry and/or are aligned. Alternatively, the tube 22 comprises a radially uneven thickness of material. In one example, the inner cross-section is triangular and the outer cross-section is a square or a circle. Alternatively or additionally, the cross-sections may be asymmetric relative to the main axis of tube 22. Alternatively or additionally, the cross-section geometry of the tube may change along the axial dimension of the spacer. In a preferred embodiment of the invention, variations in the cross-section and/or tube material thickness are related to the spike positions and/or desired function. In one example, the tube diameter increases at the end-caps.

Wires

Figure 2M:
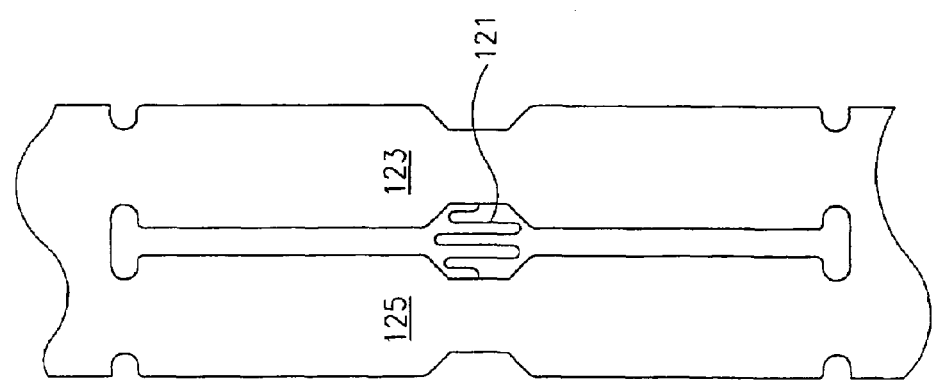
FIG. 2M is a spread layout of a spacer including an expansion limiting wire, in accordance with a preferred embodiment of the invention.
Figure 20A:
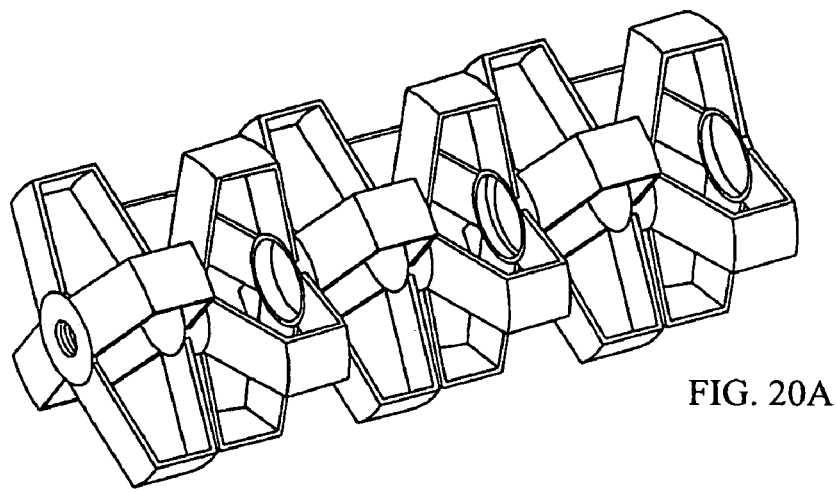
FIG. 20 illustrates a portion of a spacer, in which a plurality of banded areas indicate portions to be annealed, to assist in the expansion of the spacer, in accordance with a preferred embodiment of the invention.
Figure 20B:
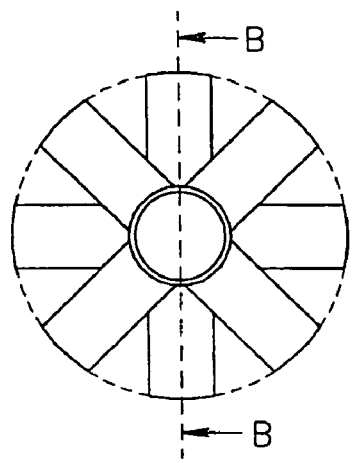
Figure 20C:
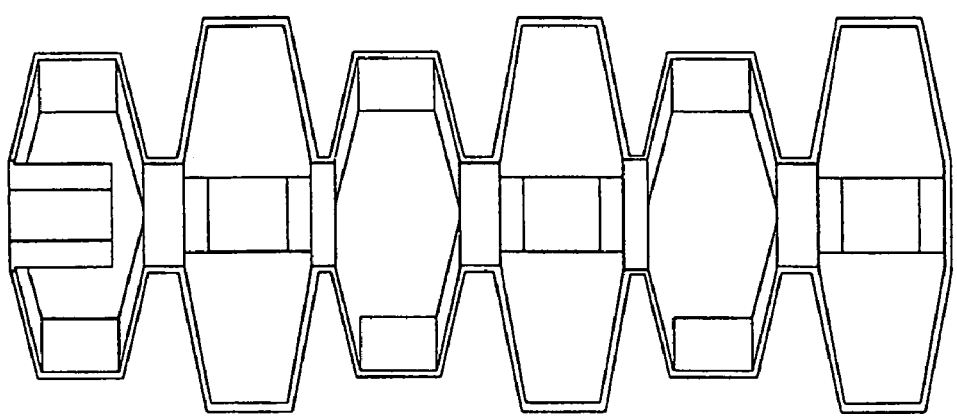
Figure 2P:
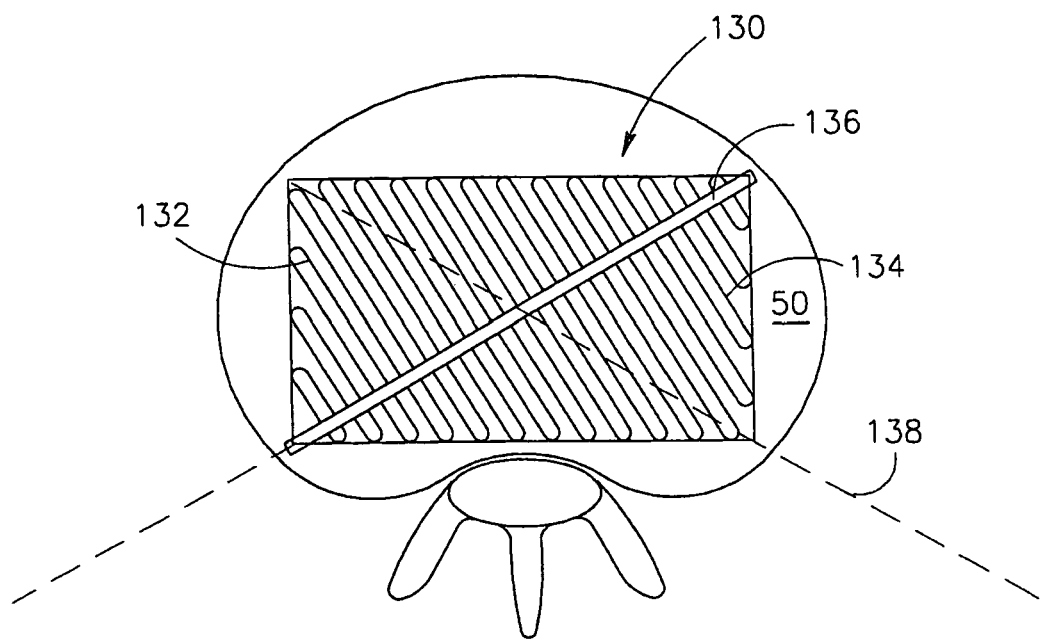
FIG. 2P illustrates a spacer having a collapsed axis which is not parallel to an expanded axis of the spacer, in accordance with a preferred embodiment of the invention.

FIG. 2M illustrates a wire 121, which can be used, for example, to restrict the expansion of the spacer. In the figure, wire 121 will restrict the allowed distance between the peaks of its adjacent spikes, spike 123 and spike 125. If such wires are formed between the peaks of all the spikes in the circumference of the spacer, the maximum extension of the spike swill be limited by the length of the wires. Alternatively or alternatively, the wire may only limit the angular distance between two spikes. Additionally or alternatively, such a wire may connect between a spike and a non-extending portion of the spacer. Additionally or alternatively, such a wire may be attached to a part of a spike other than its peak, for example to the middle of a spike's leg. As can be appreciated, in some preferred embodiments of the invention, the wires are not uniformly distributed over the spacer, for example being a function of axial position, radial position and/or spike geometry or distribution. Alternatively or additionally, some wires may be cut or removed by a physician prior to insertion of the spacer.

Spacer Cross-Section

Typically, the cross-section of an expanded spacer is preferably selected to match a desired usage. In the vertebra, a disc may be replaced with two parallel spacers, one on each side of the spine. In this configuration, the cross-section of the inter-vertebral spacer approximates a rectangular box, which is thicker in the middle than at its ends. In a preferred embodiment of the invention, the axial variation in cross-section may be provided by varying spike length or tube diameter, as described above. Alternatively or additionally, the cross-section shape of the spacer may be varied from being a circle, for example to be a rectangle or a square. It is also noted that a square spacer often moves around less than a circular spacer does.

In a preferred embodiment of the invention, the geometry of the cross-section may vary along the axis, for example the radius increasing or decreasing with axis or approximating an hour-glass shape or a cigar shape. Alternatively, the cross-sectional shape may vary, for example from being a circle at on end of the spacer to being a square at the other end of the spacer.

Spacer Axis Geometry

In a preferred embodiment of the invention, the axis of tube 22 in its collapsed and expanded configuration is substantially straight. Alternatively, the axis of the spacer may be curved or broken piece-wise while the spacer is inserted and/or after insertion is complete. Alternatively or additionally, the axis of the spacer may be curved or broken in the collapsed spacer.

In one example, the spacer is manufactured in a bent configuration to aid its insertion. During insertion the spacer is preferably straitened and/or otherwise adapted to the space into which it is inserted.

In another example, the spacer is inserted straight and then bent to adapt the spacer to the insertion space. In one example, a "C" shaped or horse-shoe shaped spacer replaces an entire disc with a single spacer.

The spacer may be preformed to be axially bent and then elastically or super-elastically maintained in a different configuration for insertion. Alternatively, the spacer is plastically deformed during the expansion, for example (with reference to FIG. 2E) if member 72 is a curved stylet or (with reference to FIG. 2F) using a curved collar. Alternatively, the spacer is bent after it is partially or completely expanded, for example by inserting a bendable stylet into the lumen of the spacer and then bending the stylet (from outside the body).

Alternatively or additionally, the spacer may be designed so that it bends when it is expanded. In one example, the spike slots are made uneven on opposing sides, so that the ring segments have a different axial dimension on opposite sides of the spacer. FIG. 2N is a layout of a spacer in which one spike "A" is shorter than a second spike "B" on the opposite side of the spacer. When the spacer is expanded, the uneven spike lengths will cause the spacer to bend.

Figure 5B:
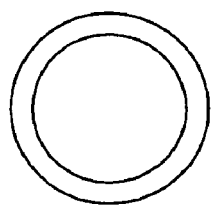
FIGS. 5A-5C illustrates a spacer in which slits are formed on the spacer in a spiral pattern.
Figure 5A:
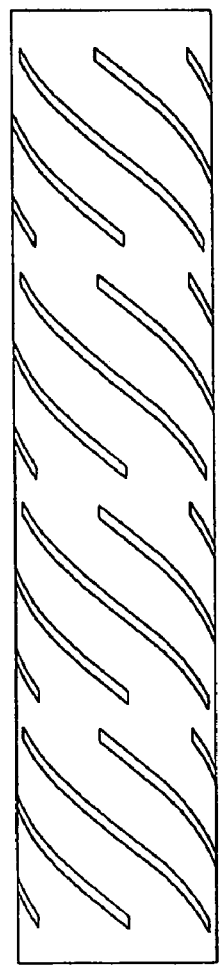
Figure 5C:
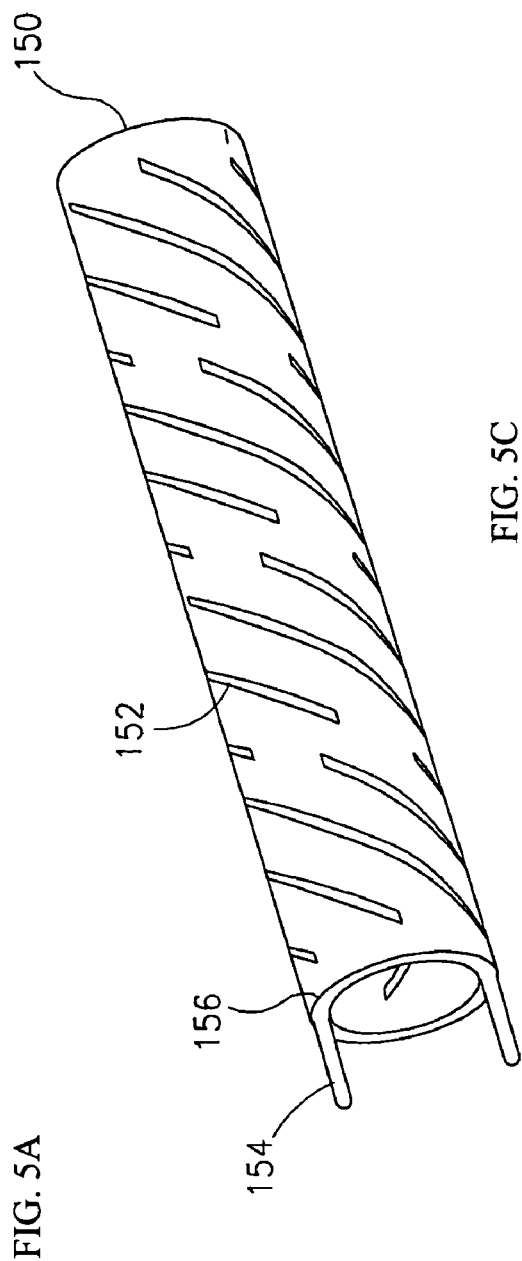

In another example, the spike lengths are unequal on the two sides of the spacer, so when they push against the surrounding bone, the inner lumen is bent. Alternatively, the bending configuration is selected to create a desired contact and/or contact pressure between the spikes and the surrounding bone. Additionally or alternatively, the spike lengths and/or the slots are designed so that the spacer twists around its axis as it is expanded, for example, as shown in FIGS. 5A-5C, where the spike slots are not parallel to the spacer axis.

Space Filling Spacer

In some embodiments, it is desirable that the spacer fill the intra-vertebral space as completely as possible. In particular, it is desirable to maximize the contact area between the spacer and the vertebrae. As a result, it is expected that the spacer will embed less into the vertebra. As described below, this result may be achieved by surrounding the spacer with a mesh, fabric or a balloon. Alternatively, spike shapes, such as described below with reference to FIGS. 6F and 6C also increase the contact area. In the example of FIG. 6F, a small extension of the spike is provided to enter into the vertebra, to prevent slippage of the spacer.

FIG. 2P illustrates a spacer 130 having an inner axis 136 which is not parallel to an axis of the expanded spacer. In a preferred embodiment of the invention, spacer 130 is inserted into an intra-vertebral space 55 at an angle which is oblique relative to the main axes of the space, minimizing, the danger of damage to important body structures. However, when the spacer is expanded, an asymmetrical arrangement of spike lengths causes the final profile of the expanded spacer to match intra-vertebral space 55. In the example of FIG. 2P, spikes 132 decrease in length along the spacer and corresponding spikes 134 on the opposite side of the spacer increase in length. Optionally, a second spacer may be inserted, from the other side of the intra-vertebral space, along a doted line 138, indicated in the figure. In the embodiment of FIG. 2P the lengths of the spikes which are perpendicular to the plane of the figure are preferably equal. However, in other embodiments these spikes may also exhibit uneven lengths. In a preferred embodiment of the invention, elongate member 60 (FIG. 2) has a marking or a groove thereon which indicates the correct orientation of the spacer.

Struts

In a preferred embodiment of the invention, when the spacer expands and spikes extends, additional structural elements, called herein "struts", extend between two (or more) spikes or between one (or more) spike and the tubular portion of the spacer. For clarity, various struts configurations (in expanded spacers) will be described and then mechanisms for generating such strut configurations will be described.

Figure 3A:
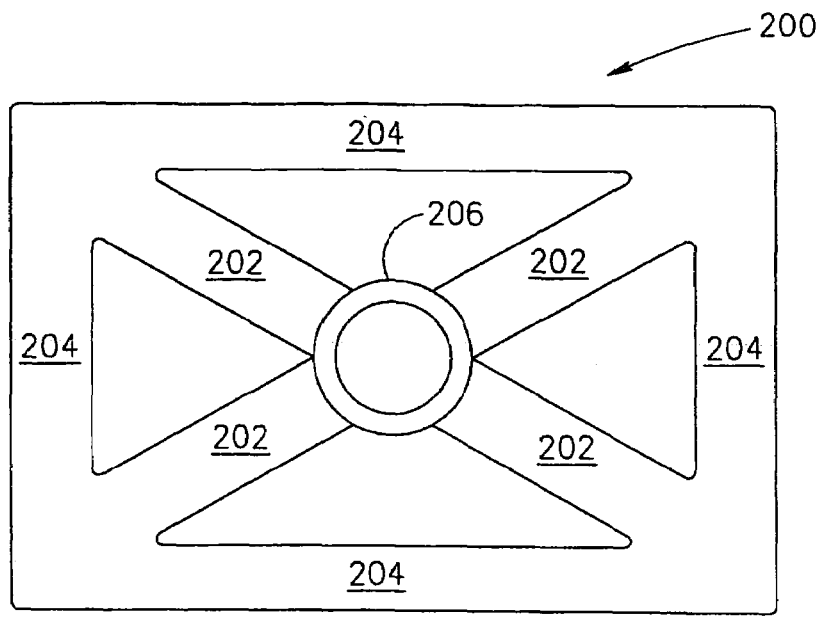

FIGS. 3A-3E are axial views of spacers with struts in accordance with preferred embodiments of the invention. Referring to FIG. 3A, a spacer 200 (when expanded) comprises a tubular portion 206 and a plurality of spikes 202 extending radially therefrom. A plurality of struts 204 connect peaks of spikes 202. In the example of FIG. 3A, the profile of the expanded spacer is rectangular, and four struts are provided, to form a rectangular profile which bounds the spikes.

Figure 3B:
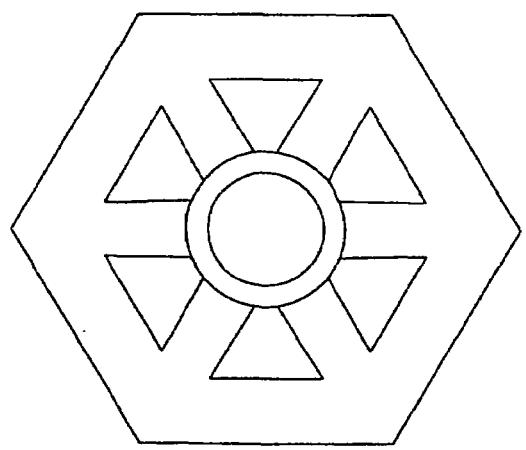

A larger or smaller number of spikes may be defined for the circumference, for example, as shown in FIG. 3B, six spikes and six struts are provided.

Not all the spikes need to be completely inter-connected by struts, for example as shown in FIG. 3C, a strut 204A connects a spike 202A and a spike 202B; a strut 204B connects a spike 202C and a spike 202D; while no strut connects spikes 202A and 202C or spikes 202B and 202D.

Additionally, the pattern of interconnection of struts need not be symmetric. For example as shown in FIG. 3D, spikes (and struts) extend only to one side of the spacer. Possibly, these and/or other various in the struts are a function of the axial and/or radial position along the spacer.

Additionally, some spikes may be connected to struts and some not connected to any struts at all. For example as shown in FIG. 3E, where two spikes 210 and 212 are connected by a strut 214, while two spikes 216 and 218 are not connected to any spikes.

In FIGS. 3A-3E, the struts are shown connected spikes which are at a same cross-section of the spacer. In some of the examples a complete ring (actually a polygon) is defined by the struts. Alternatively, the struts may connect spikes which are (also) axially displaced. Thus, possibly, a strut may be substantially parallel to the axis of the spacer. In an example of a strut interconnection pattern, the strut interconnection pattern may define a spiral around the spacer axis. These axial interconnections may be additional to or alternative to connection around the circumference of the spacer.

In the above Figs., struts were shown as connecting peaks of adjacent spikes. In a preferred embodiment of the invention, struts connect non-adjacent spikes. Alternatively or additionally, struts are connected, at least at one side thereof, to a non-peak portion of a spike, possibly even to a non-spike portion of the spacer, for example the tube, a wire or another strut.

In a preferred embodiment of the invention, struts are straight. Alternatively, at least one of the struts is bent. In one embodiment, the strut is pre-bent. In another, the strut is bent by the expansion process, for example by a wire or a second strut connected to the center of the strut. Preferably, weakened points are defined on the strut, to guide its bending.

FIGS. 3F-3M illustrate one mechanism of providing struts between spikes, in this example struts which ring the spacer at the spike peaks. In other embodiments of the invention. struts may be provided using additional or alternative different mechanisms, for example by forming the spacer from a layered material in which the struts are defined by a layer other than that which defines the spikes.

Spacer Joints

In this context it is useful to consider several types of joints and relative movements of joints movements:

(a) joints which experience only axial translation during the expansion process, for example base joints of a spike;

(b) joints which experience radial translation during the expansion process, for example peaks of spikes; and (c) joints which experience angular motion.

In addition, several types of relative motion may be experienced between pairs of joints, for example:

(a) no relative motion—two spike base joints at the same circumference of the spacer;

(b) axial translation—two base joints of the same spike;

(c) radial translation—a base joint and a peak joint of a spike;

(d) constant distance—a base joint and a peak joint of a spike;

(e) changing distance—two base joints of the same spike; and (f) angular translation—when the spacer twists while it expands.

In some cases, these various types of motion and relative motion may be combined in a single joint.

Strut Geometries

Figure 3F:
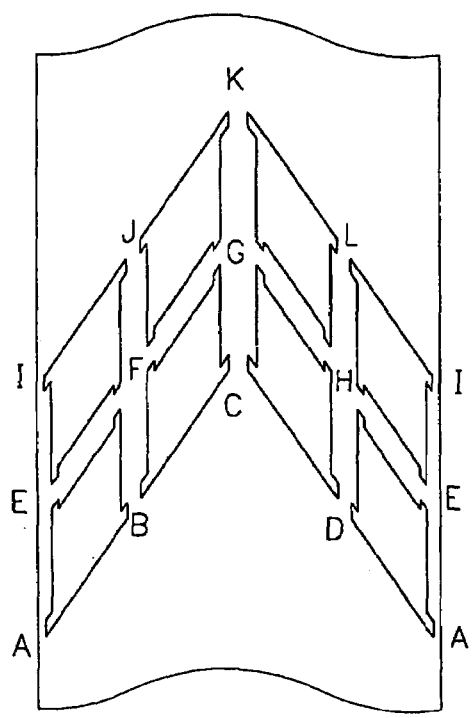
FIGS. 3F-3M illustrate one method of providing struts between spikes, in this example struts which ring the spacer at the spike peaks.
Figure 3G:
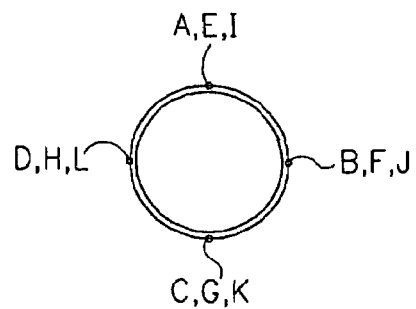

FIGS. 3F and 3G illustrate a spread view (3F) and an axial view (3G) of a spacer with struts in a collapsed condition. In a spread view, the spacer is axially split, spread open and viewed from above (somewhat like a cylindrical map projection).

Figure 3H:
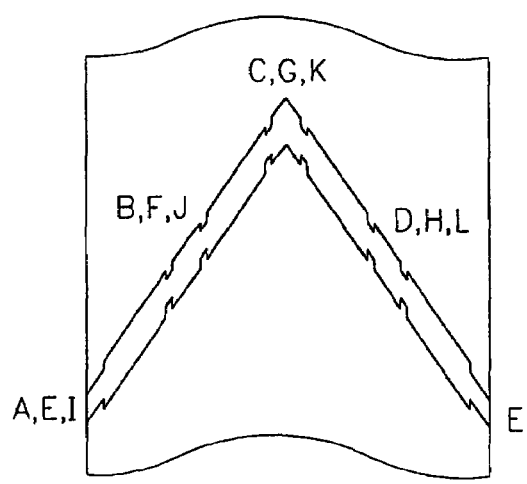
Figure 3I:
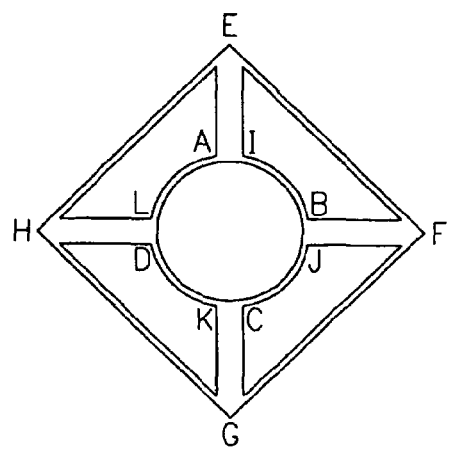
Figure 3J:
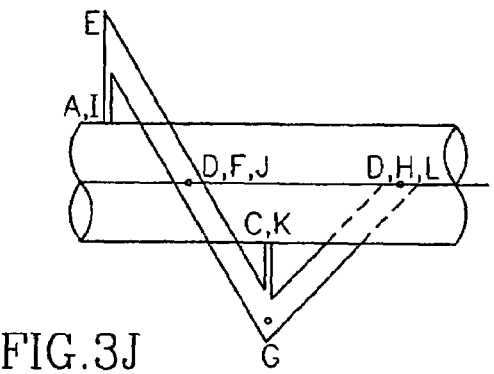

FIGS. 3H-3J illustrate the same spacer in a semi-expanded condition (spread, axial and side views), in which the spikes are extended but the struts are not in their final position.

Figure 3K:
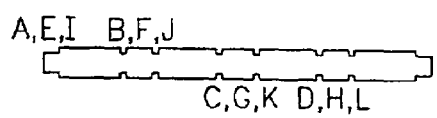
Figure 3L:
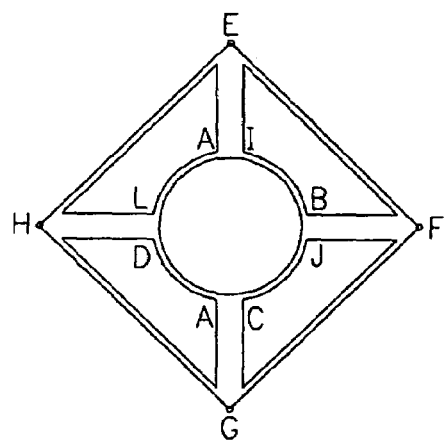
Figure 3M:
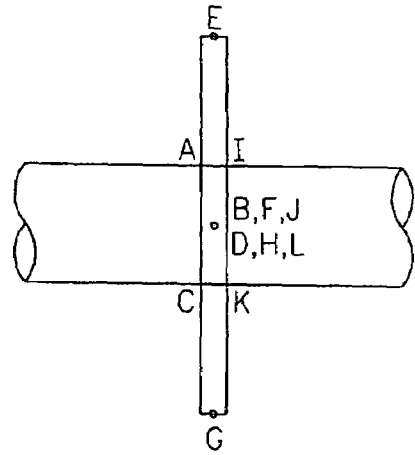

FIGS. 3K-3M illustrate the same spacer in a final expanded condition (spread, axial and side views).

This set of figures is somewhat schematic and, in some cases, the correct geometry is somewhat distorted or small features shown in one figure are not shown in another, corresponding figure.

In the following description, the motion of the spikes has been separated from the motion of the struts, to simplify the explanation. However, in some embodiments of the invention, what is described herein as separate steps is actually a single combined step in which spikes extend while the struts move to their final positions. In addition, for simplification, spikes are shown as having a zero width and a zero thickness, which is not the case in an actual embodiment.

FIG. 3F is a spread layout of an axial portion of a spacer showing four spikes: AEI, BFJ, CGK and DHL. "AEI" describes a spike in which the two base joints are "A" and "I" and the peak joint is "E". struts are defined between the peak joints as follows: EF, FG, GH and HE. Point "E" which appears in both sides of the figure. is the same point, duplicated by the layout view.

FIG. 3G is an axial view of the collapsed spacer, in which points A,E,I (and D,H,L, C,G,K, B,F,J) are shown as a single point.

FIG. 3H is a spread layout of the spacer after the spikes have been completely extended.

Each spike AEI, BFJ, CGK and DHL is shown substantially as a single point. It is noted that the spikes are still axially displaced.

FIG. 3I is an axial view of the spacer, in which the spikes are seen to be extend and the struts interconnect the peaks of the spikes.

FIG. 3J is a side view of the spacer, showing that the struts are in a non-fmat configuration. It is noted that the extension of the spikes causes the struts to be lifted from the surface of the spacer, so that they are spaced apart from the spacer. The spikes, however, are attached directly to the spacer, at least at one of their ends.

FIG. 3K is a spread layout of the spacer after the expansion (and axial contraction) is completed. The spikes are shown as all being at substantially a same axial position of the spacer.

FIG. 3L is an axial view of the spacer, showing the spikes and the struts being fully deployed.

FIG. 3M is a side view of the spacer showing that the spikes and the struts are at a same axial position.

Spacer Parameter Control

In the design of a spacer, the properties of the collapsed and/or expanded spacers may be modified by controlling various aspects of the spacer. In particular, one or more of the following aspects may be modified:

(a) length of collapsed spacer;
(b) geometry of collapsed spacer;
(c) length, width, number, density and/or geometry of spikes;
(d) relative positioning of spikes among themselves and/or the rest of the spacer;
(e) elasticity, stiffness, plasticity and other mechanical properties of the material(s) which compose the spacer and/or of the spikes and/or of non-expanding portions of the spacer (if any);
(f) metallurgic and other treatments of the spacer;
(g) thickness and variations in thickness of the spacer material; and
(h) coating.

In particular, especially as described herein, the above aspects may be different for different parts of the spacer and/or for different spikes. Alternatively or additionally, these aspects may vary temporally, for example, elasticity varying as a result of gradual "learning" of the spacer.

Spacer Manufacture

In a preferred embodiment of the invention, the spacer is manufactured by laser cutting or e-beam cutting a metal tube. The metal tube may be formed as a tube, for example by extrusion or it may be formed into a tube from a sheet, for example by welding. Preferably, such a weld line, which may not be straight, lies between spikes. Possibly, the sheet is first cut and/or otherwise at least partially shaped and then formed into a tube.

In some preferred embodiments of the invention, selected portions of the spacer are metallurgically treated. In one embodiment, a portion of the spacer is annealed by heating (not cutting) that portion, for example, with a laser, an e-beam or a plasma beam. Alternatively or additionally, the rest of the spacer is protected from the heating of the beam, for example using an external or internal heat dissipating mold or by using a mask, which block heat-causing beams. Possibly, the mold comprises a heat conducting material, such as copper or aluminum. Alternatively or additionally, the mold includes active cooling, for example water, oil or gas cooling or cooling by sublimation of the mold material.

In a preferred embodiment of the invention, the annealing is used to make points or areas that twist or bend more malleable, while maintaining non-distorting portions (such as spike legs and struts) more rigid.

Other possible types of local metallurgic treatments (possibly utilizing a mold) include, localized ablation (not cutting through), deposition of ions, local sintering, local welding, cladding, plating, drilling of small holes and/or attaching additional thickness of material. It should be noted that in some embodiments, even the entire spacer can be annealed, as the many parts of the spacer are cold-worked by the expansion process. Optionally, the expansion process takes care not to overly distort areas on the boundary between annealed and un-annealed portions, for example by providing a suitable mold for the expansion to occur against, for example the collars of FIG. 2.

In a preferred embodiment of the invention, the annealing processes utilize a sensor (contact or non-contact) to provide feedback on the local temperature achieved at the annealed location and/or locations not to be annealed. For example, the sensor may be used to prevent the metal from being melted by the annealing beam. The sensor can be used for real-time control of the beam intensity and dwell time. Alternatively or additionally, the sensor is used to determine if a certain location needs additional treatment to achieve annealing.

Figure 20:
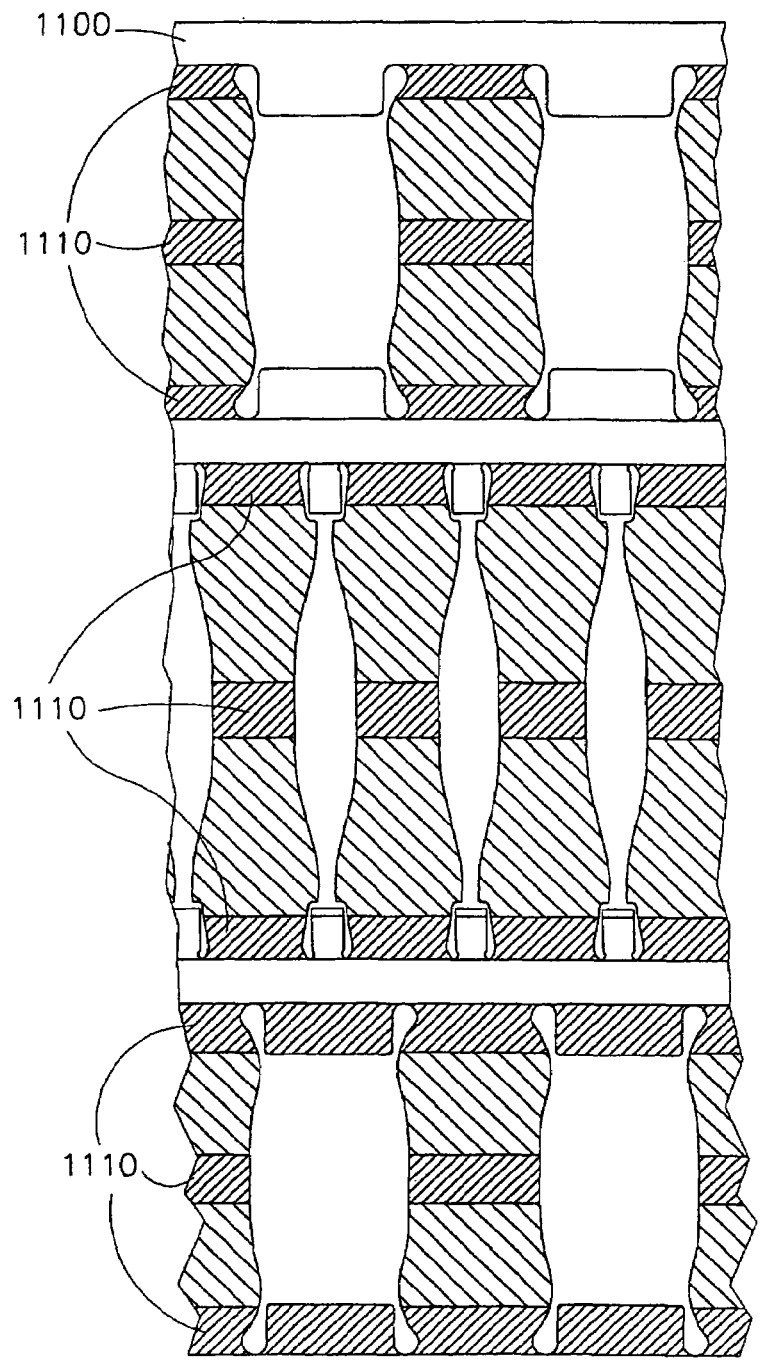

FIG. 20 illustrates a portion 1100 of a spacer, on which figure banded areas illustrate portions to be annealed, to assist in the expansion of the spacer, in accordance with a preferred embodiment of the invention.

As shown in FIG. 20, the slits that define the spikes do not have to be straight and can be curved, for example. As shown, the spike shape is that of an hour-glass. It is noted that by annealing the center of the spike, also inverse hourglass shapes can be provided.

Figure 21A:
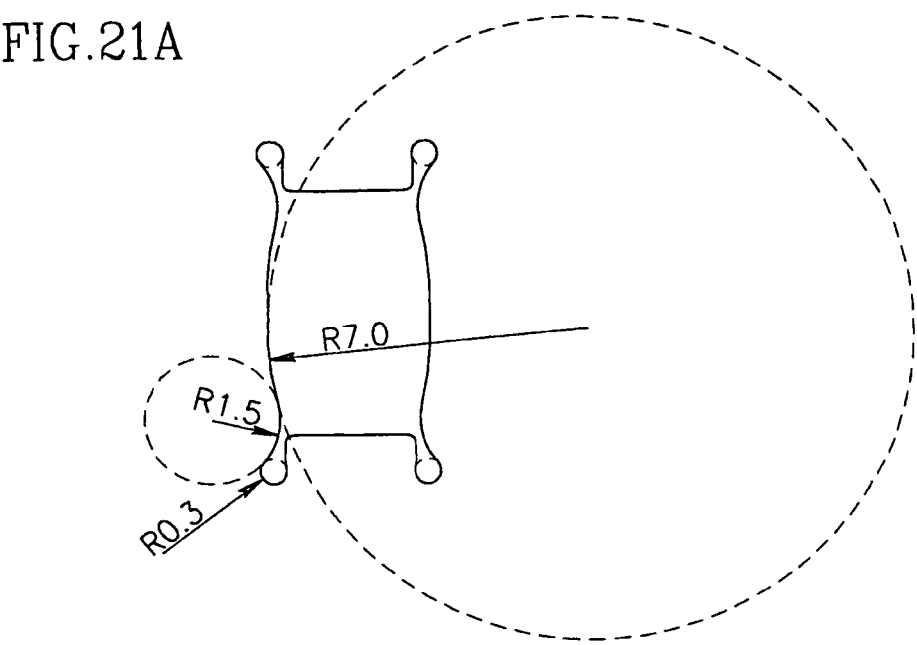
FIGS. 21A and 21B illustrate spike designs for stress-release, in accordance with a preferred embodiment of the invention.
Figure 21B:
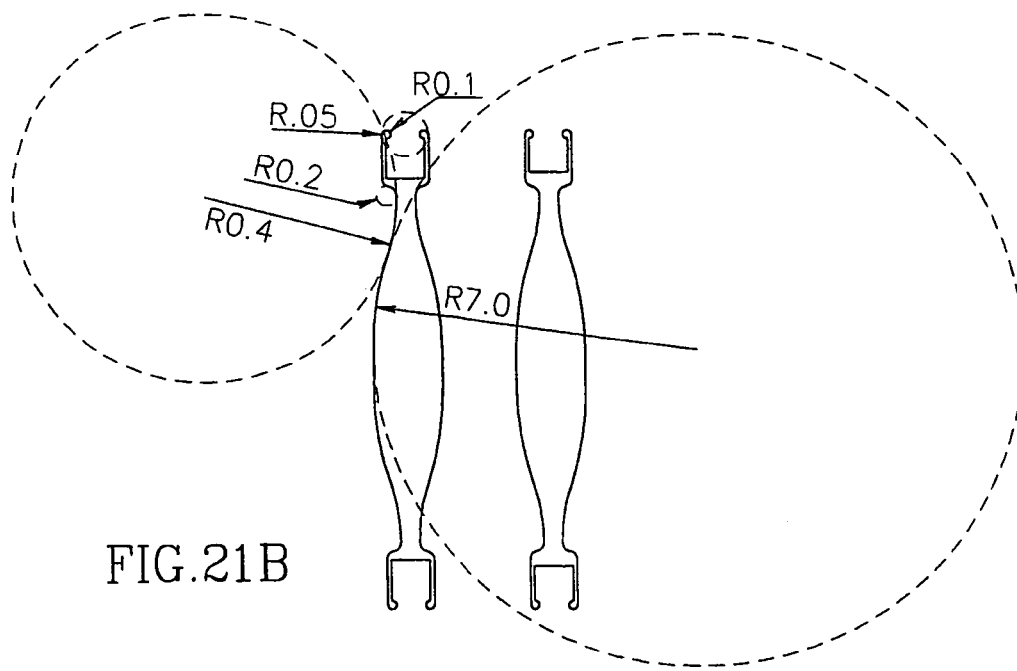

The hole sin the spacer, used to relive stress, need not be round, for example as shown in FIGS. 21A and 21B, the shape of the slits and the holes is that of a spline. Such a shape may be desirable as the spike extends out of the spacer plane, applied non-planar stress to the spacer. The measurements shown are for a lordotic spacer having a 11×11 mm cross-section and a 4 mm tube cross-section As described in a PCT application filed on even date in the Israel receiving office, such local annealing may also be applied to other implant types, such as dental implants or intramedullar nails and especially to portions of such medical orthopedic implants where significant elongation, such as 40% or more is required.

In preferred embodiments of the invention, the spacer is subjected to one or more of the above treatments and/or one or more of the above aspects and/or design properties of the spacer are modified, especially as described herein, in order to achieve one or more of the following desired spacer properties:

(a) resilience profile of the spacer, preferably as a function of direction of force application;

(b) collapse profile, i.e., how much radial force will cause the spacer to (typically undesirably) collapse and how much will it collapse;

(c) resistance to axial, rotational, radial, twisting and/or flexing motion, prior, during and/or post insertion;

(d) amount of conformance to body-structure geometry and ability to adapt, while being expanded and/or after being in place, possibly requiring variations in properties over the spacer;

(e) type and/or extent of contact with bone, especially with respect to digging into bone;

(f) surface area, especially with respect to adherence to new bone growth and/or danger of irritating the body;

(g) ease and/or method of insertion, expansion, bone anchoring, adjustment and/or retraction;

(h) size of playground, i.e., the allowed error in matching a particular spacer to a particular medical situation; and (i) support and/or enhancement of new bone growth.

Spacer Surface Treatment

In a preferred embodiment of the invention, the spacer is made of unalloyed Titanium grade 2, as per ASTM F67. An inner bolt is preferably made from Ti-6AL-4V, per ASTM 136.

In a preferred embodiment of the invention, the spacer is (optionally) thermally treated at between 650-800° C., preferably in a vacuum or a non-reacting atmosphere. Other temperature ranges and/or various annealing times may be used, for example above 400° C., above 700° C. or above 800° C. Preferably, but not necessarily, the temperature is lower than 1100° C., 1000° C. or 900° C. Exemplary annealing times are 1 millisecond, 1 second and 10 seconds. Typically, the annealing times and temperatures vary with the material type and/or previous processing of the material. In some cases, even surface melting is desirable.

The spacer is formed from a tube (by cutting) either before or after the thermal treatment. However, the spacer may also be formed from a sheet or using other methods.

Thereafter, several treatments may be applied to the spacer, for example one or more of the following, in order to remove contaminants, remove debris from the forming process, smooth sharp edges, deburr and/or reduce micro-fractures.

In a first treatment, the spacer is soaked in a reagent containing 5 ml of $HNO_3$, 2 ml of HF and completed to 100 ml using $H_2O$, for 100 seconds at 25° C. The spacer is then washed and rinsed off in an ultrasound agitated water bath at 60° C. the spacer is then air-dried.

In a second treatment, mechanical cleaning, the spacer is placed in a trumal, sprayed with glass (preferably using small crystals), sand-sprayed and/or polished with diamond paste (preferably with a small grain size).

Alternatively or additionally, an electropolish method is used, for example using a mixture of 660 ml methanol, 440 ml 2-butoxy-ethanol and 66 ml perchloric acid or a mixture of 70% $HNO_3$, 10% BF and 20% $H_2O$ (by volume). An exemplary current is about 100 $mA/mm^2$. An exemplary voltage is about 15V Alternatively or additionally, a surface treatment comprises:

(a) applying a light base after laser-cutting to remove fat and debris;

(b) water washing;

(c) pickling at room temperature for between 1 and 5 minutes;

(d) water washing;

(e) washing in 60° C. ultrasonically agitated water; and (f) air drying.

Exemplary acids for pickling are a mixture of $HNO_3$ 20-40 ml, HF 1-2 ml and completed to 100 ml using $H_2O$ or a mixture of $HNO_3$ 10 ml, HF 5 ml and Lactic acid 30 ml.

Another exemplary surface treatment is a salt bath:

(a) soaking for 5-10 minutes in a 20° C. salt bath.

(b) water wash;

(c) between 2-5 minutes soaking in a 10% by volume solution of $H_2SO_4$ (d) water wash; and (e) repeating the acid soak until a desired layer thickness is removed. By selectively coating the spacer with acid resistant material, selective etching can be achieved.

Square Spacer Embodiment

Figure 4A:
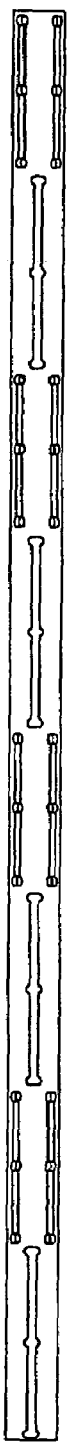
FIG. 4A shows a flat projection of a spacer having a square profile when expanded, in an un-expanded configuration, in accordance with a preferred embodiment of the invention.
Figure 4A:
Figure 4B:
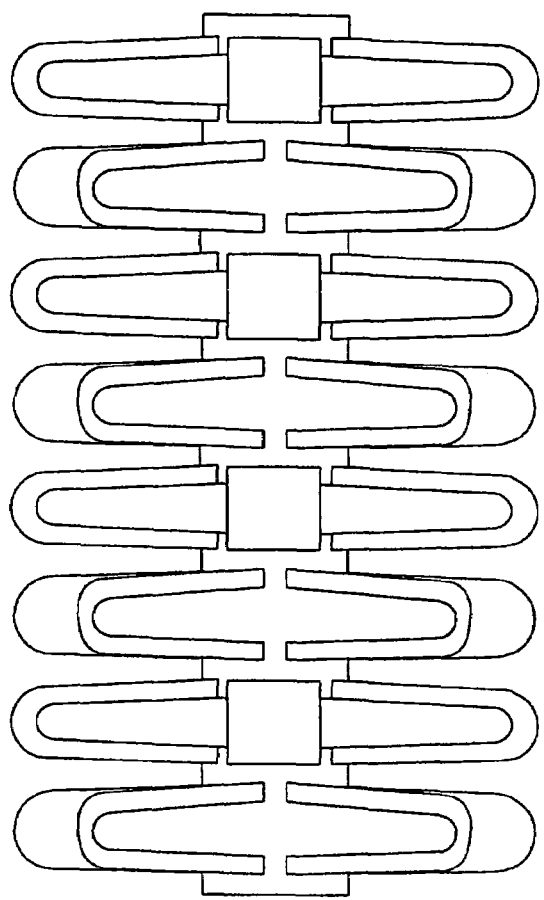
FIGS. 4BA and 4BB shows an axial flat projection and a front flat projection of the spacer of FIG. 4A, respectively, in an expanded configuration thereof.
Figure 4B:
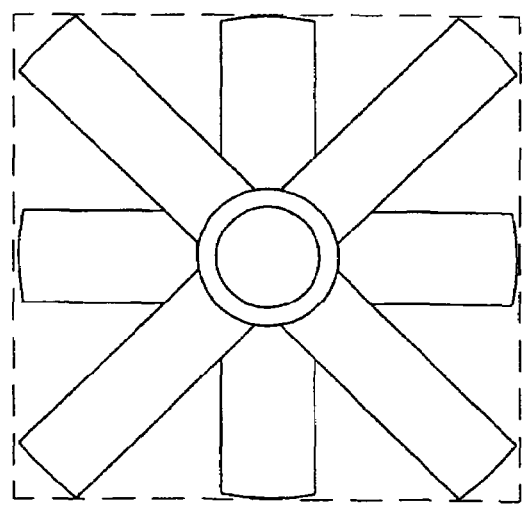
Figure 4C:
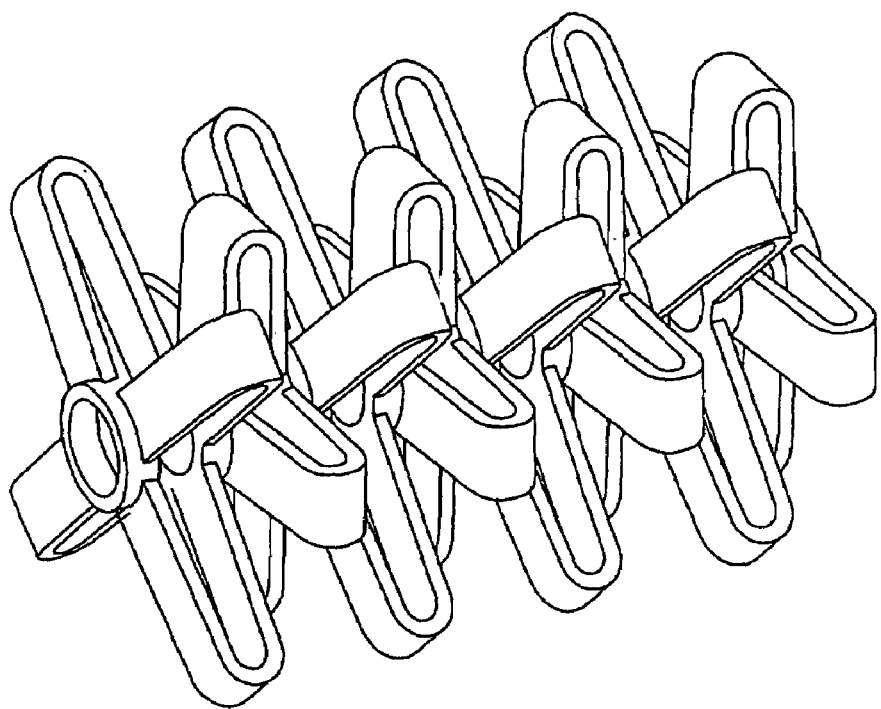
FIG. 4C is a perspective view of the spacer of FIG. 4A, in an expanded configuration.

FIG. 4A shows a flat projection of a spacer having a square cross-section when expanded, in an un-expanded configuration, in accordance with a preferred embodiment of the invention. FIGS. 4BA and 4BB shows a flat projection of the spacer of FIG. 4A, in an expanded configuration. FIG. 4C shows a perspective projection of the spacer of FIG. 4A, in an expanded configuration. The above figures also include measurements for a preferred embodiment of the invention. For example, a length of 114 mm (un-expanded) and 23.9 mm (expanded), a diameter of 4 mm (un-expanded) and 14 mm (expanded)—each side, the material may be titanium, with a thickness or 0.5 mm. Alternatively or additionally, the material may comprise Nitinol (NiTi), Titanium, Surgical Stainless Steel, plastic, composite and/or various alloys, such as bio-inert metal alloys.

In some embodiments of the invention, the spacer is made bio-absorbable, so that as bone ingrowth proceeds the spacer decomposes. Thus, the spacer is less likely to exert localized high pressure on the vertebra (which may cause remodeling). Possibly, only some of the spacer is absorbed, for example, sharp edges thereof.

Spacer Finish

In a preferred embodiment of the invention, the spacer as described herein or elsewhere in this application, has a smooth surface. Smooth surfaces are generally less prone to fracture and/or micro-fracture propagation. Alternatively or additionally, at least some of the spacer surface is rough, to encourage bone growth and/or adherence. Alternatively or additionally, at least some of the spacer surface includes small barbs, to engage the bone and or soft tissue. In some embodiments, only the tips of the spikes and/or areas near the tips have non-smooth surfaces. Such roughness and/or barbs may also be achieved by coating a smooth spacer.

Lordotic Spacer

Figure 4D:
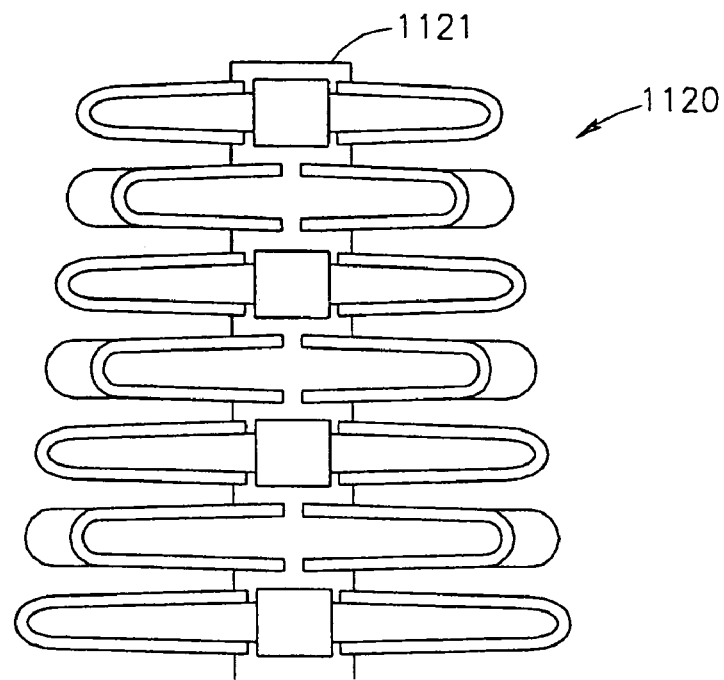
FIGS. 4DA and 4DB illustrates a variation of the spacer of FIGS. 4A-4C, in which spikes only extend in six transaxial directions and not eight, in accordance with a preferred embodiment of the invention.
Figure 4D:
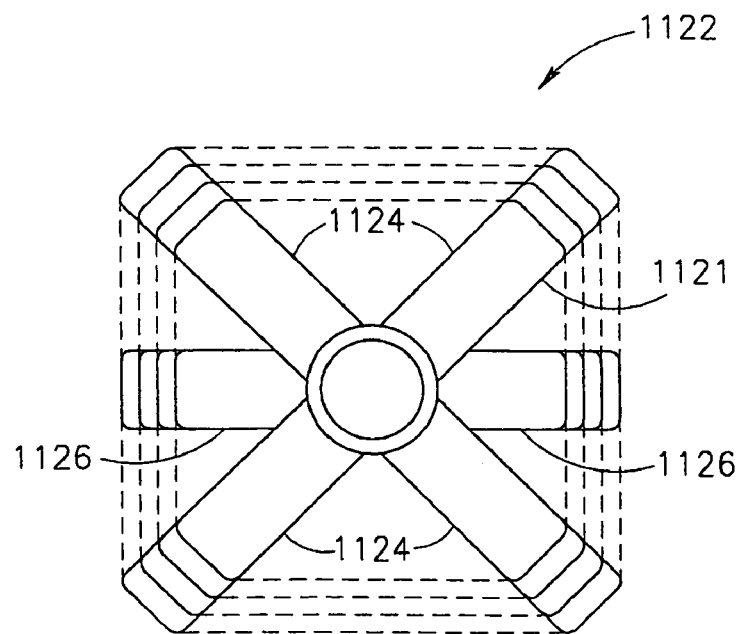

FIGS. 4DA and 4DB illustrates a variation of the spacer of FIGS. 4A-4C, in which spikes only extend in six transaxial directions and not eight, in accordance with a preferred embodiment of the invention.

A spacer 1121 is shown in a side view 1120. Optionally, and as shown, the cross-section diameter increases with the axis, with a greater diameter preferably provided for the side near the stomach of the patient.

A front view 1122 illustrates that only six spike directions re utilized. Spikes 1126 server to separate the two vertebras and spikes 1124 serve to stabilize spacer 1121. No Horizontal stress exists in the back, so horizontal pointing spikes are not provided in this embodiment.

Double Spacer

Figure 4E:
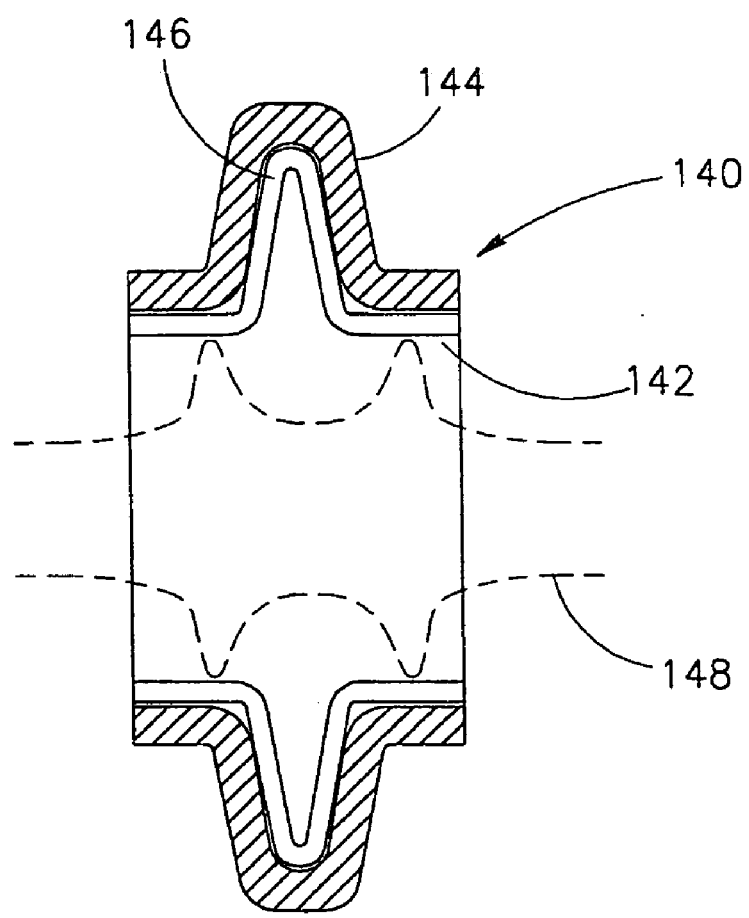
FIG. 4E illustrates a spacer configuration in which one spacer is expanded within another spacer.

FIG. 4E illustrates a spacer configuration in which one spacer 142 is expanded inside another spacer 140, for example, to increase the total stiffness of the spacers. In a preferred embodiment of the invention, spikes 146 of inner spacer 142 match the hollows of spikes 144 of outer spacer 140. Alternatively or additionally, spacer 140 may function as a mold for expansion of inner spacer 142 (for example as in FIG. 2G). In some embodiments, this may require the spikes to be sharper on the inner spacer and/or the internal structure of the outer spacer to be more guiding, such that the expanding inner-spacer spikes are suitably guided.

Alternatively, spikes 146 may not match spikes 144, for example as shown by dotted line 148. Preferably, the two spacers are selected so that none of the spikes match or so that spikes only on one side and/or one portion of the spacers match.

Generally, the inner spacer is inserted into the first spacer if it is determined that the stiffness of the first spacer is too small. In some cases this may be the result of the expansion of spacer 140 being limited, so the base of spikes 144 is wide (resulting in a weak spike). Preferably, the inner spacer is inserted during the same procedure. Alternatively, an inner spacer may be inserted later, possibly a few days after the first procedure is completed.

Alternatively or additionally to inserting spacers one inside the other, multiple spacers may be used for a single intervertebral space (or other body space) in other configurations. In one configuration, a disc is replaced by two parallel spacers, on one each side of the spinal column. Generally, the two spacers do not touch. Alternatively, the two spacers may be bent and touch at one or two of their ends. In another example, two, three, four or more spacers may be inserted to be coaxial, for example in series and/or to be co-planar, for example side-by side. Typically, the spikes on the two spacers interlock, at least as a result of friction and/or inherent flexibility of the spikes. In some cases, the spike spacing and/or spike shapes may be selected to encourage or discourage such an interlock. When the spacers are inserted in series, the spacers may include forward folding and/or rear-folding spikes, to encourage interlocking. The multiple spacers may be expanded in parallel. Alternatively, a second spacer is expanded only after a first spacer is already expanded. Possibly however, the expansion of the first spacer may be adjusted to match the expansion of the second spacer. In some cases, the spacers are not coaxial, for example their axes being somewhat perpendicular, for example as described with reference to FIG. 2P.

Alternatively or additionally, multiple spacers may be used to fill a space where, possibly, a single straight spacer would have sufficed. However, in some cases better control over the spacing and/or spinal support are achieved using multiple spacers.

In one preferred embodiment of the invention, the spacers may comprises different materials, for example to provide composite and/or locally adapted mechanical characteristics. Alternatively or additionally, different materials may be used to provide a small electro-chemical potential between the spacers, for example to encourage bone growth. Alternatively or additionally, a small voltage potential may be provided using a two layer material to construct the spacer, with an isolator between the spacer layers. Possibly, a voltage source is connected between the spacers, with the circuit closed by body fluids.

Spiral Cut Spacer

FIGS. 5A-5C illustrates a spacer 150 in which slits 152 are defined on the spacer in a spiral pattern. In this embodiment, spacer 150 may be expand by applying a rotational force to the spacer, rather than an axial force. In a preferred embodiment of the invention, one end of the spacer is modified to grip bone, to provide a suitable anchor for bone, for example as exemplified by a pair of extensions 154. In a preferred embodiment of the invention, extensions 154 fold out, for example as shown by dotted line 156, to radially grasp the bone prior to the expansion of the spacer. Preferably, the extensions are made of an elastic or super-elastic material which is maintained in an axial configuration until the spacer is inserted in place. Such anchoring may also be useful for other embodiments of the invention, described herein. However, in other preferred embodiments of the invention, no bone anchors are provided, as the spacer can expanded in place without anchoring.

Spike Variants

Figure 6A:
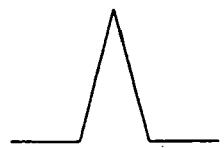
FIGS. 6A-6V illustrate variants of spikes and/or spike orientations, in accordance with alternative preferred embodiments of the invention.
Figure 6B:
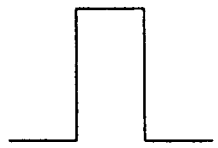
FIGS. 6W and 6X illustrate spikes having portions which twist when the spacer is expanded.
Figure 6C:
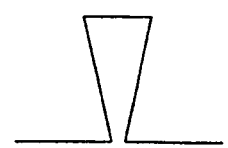
Figure 6D:
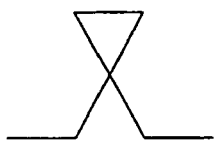
Figure 6E:
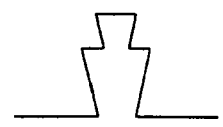
Figure 6F:
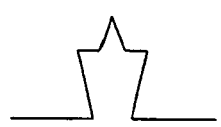
Figure 6G:
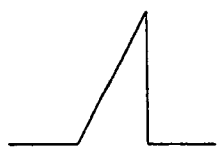
Figure 6H:
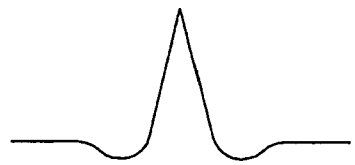
Figure 6I:
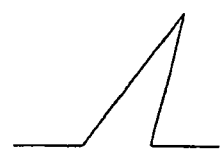
Figure 6J:
Figure 6K:
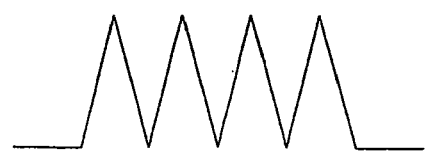
Figure 6L:
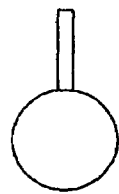
Figure 6M:
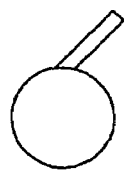
Figure 6N:
Figure 6O:
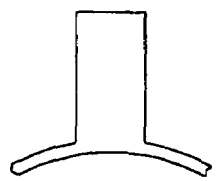
Figure 6P:
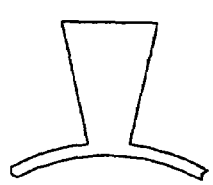
Figure 6Q:
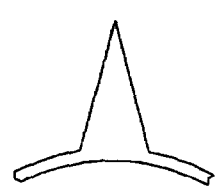
Figure 6R:
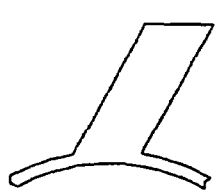
Figure 6S:
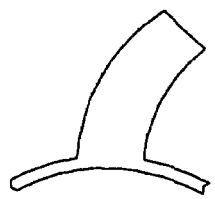
Figure 6T:
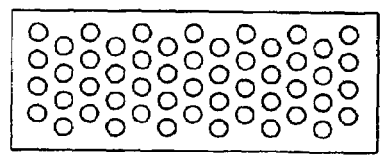
Figure 6U:
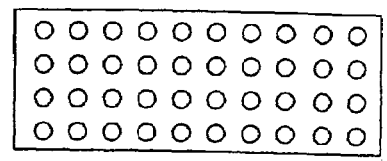
Figure 6V:
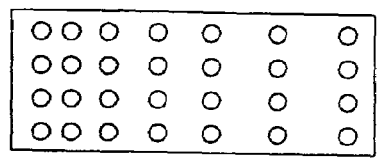

FIGS. 6A-6V illustrate variants of spikes and/or spike orientations and/or spike layout patterns, in accordance with alternative preferred embodiments of the invention.

Spike Side Profiles

FIGS. 6A-6K illustrate various spike side profiles (i.e., viewing from the side of the spacer), in accordance with preferred embodiments of the invention. Generally, the profiles on both sides of the spike match. However, in some preferred embodiments of the invention, the profile may vary over the width of a spike. Thus, a projection of the spike onto a plane perpendicular to the spike and parallel to the spacer axis may yield a square shape, but may also yield a triangle shape or a more complex shape, for example an hourglass.

FIG. 6A illustrates a triangular profile, however, the tip of the spike will usually be rounder.

FIG. 6B illustrates a rectangular profile.

FIG. 6C illustrates an inverse triangular profile.

FIG. 6D illustrates an hourglass profile. Profiles 6C and 6D have the possible advantage of having a large area in contact with adjacent bone. A possibly advantage of the spike of FIG. 6D is a resistance to collapsing and the possibility of any collapsing being partial, whereby the spike becomes shorter, rather than completely collapsing. Another advantage of these inverted spikes is that their inverted bases abut against adjacent spike's bases, possibly stiffening the spacer.

FIG. 6E and FIG. 6F. illustrate two level spikes. One possible advantage of such spikes is a is that the upper level spike portion can collapse without affecting the lower level spike portion. Another possible advantage is providing a lower portion of a spike which can resist large loads and an upper portion of a spike which better engages the adjacent bone tissue. Another possible advantage of such spike is the provision of a greater contact surface between the spike and the bone.

FIG. 6G illustrates an asymmetric spike. In addition, the other spikes described herein may be constructed to be asymmetric.

FIG. 6H illustrates a spike having portions which are below a surface of the spacer.

FIG. 6I illustrates a spike which overhangs and which is at a non-normal angle to the spacer. The angle maybe between 89° and 20°, for example about 40° about 60°, about 70° or about 80°. Alternatively or additionally, the spike profile may be curved.

FIG. 6J illustrates a spike in which only one arm of the spike is connected to the spacer. This spike form is preferably manufacture by pre-loading such a strip to be extended and maintaining the spike in a flat position until the spacer is inserted and/or axially contracted. In a preferred embodiment of the invention, when the spacer is shortened, the spike element is above the surface of the spacer and, so, is guided by the surface of the spacer to a more extended configuration. Possibly, the surface of the spacer across the spike protrudes from the spacer, to further urge this spike in a radial direction (rather than allowing axial translation).

FIG. 6K illustrates a spike including a plurality of sub-spikes.

Spike Orientation

FIGS. 6L-6N illustrate (using an axial view) variations in an angle between the spike and the spacer, in a plane perpendicular to the spacer axis. Although right-leaning spikes are shown, in some preferred embodiments of the invention left leaning spikes are used.

FIG. 6L illustrates a spike that is normal to the spacer surface.

FIG. 6M illustrates a spike which is at an intermediate angle to the spacer surface, for example between 10° and 80°, for example about 30°, about 50° or about 70°.

FIG. 6N illustrates a spike which is parallel to the spacer surface.

FIGS. 6O-6S illustrate (using an axial view) variations in a spike profile in the plane perpendicular to the spacer axis. It is noted that variations in this profile of the spike may be affected by cutting the spike-defining slit in the form of the desired profile. Preferably, portions of the surface of the spacer are removed so that the spike defining region has a rectangular form. However, this is not required. Only the front profiles are shown. Generally, the back profiles match the front profiles. However, the front and back profiles may be different, in some preferred embodiments of the invention.

FIG. 6O illustrates a rectangular profile.
FIG. 6P illustrates a trapezoid profile.
FIG. 6Q illustrates a triangular profile.
FIG. 6R illustrates an angled profile.
FIG. 6S illustrates a bent profile.

Spike Layouts

FIGS. 6T-6V illustrate spread layouts of spikes on the surface of a collapsed spacer, in accordance with various preferred embodiments of the invention. In the illustrations, the spacer is expanded, axially slit, flattened, and viewed from above. The spike locations are indicated as circles, even though, they may have other forms when viewed from above, typically that of a rectangle. The radial and/or axial and/or spatial density of spikes may vary in some embodiments from what is shown in the figures.

FIG. 6T illustrates an alternating spike pattern, in which the spikes are arranged in rings which have an angular offset between them. The number of spikes per ring may be the same for all the rings or may be different, periodically and/or as a function of axial position. The pattern may also be viewed as a hexagonal grid layout.

FIG. 6U illustrates an even spike distribution, arranged on grid vertexes of a rectangular grid.

FIG. 6V illustrates a spike distribution in which the axial spike density varies as a function of the axial location. Alternatively or additionally, the radial density may vary as a function of the axial position. Alternatively or additionally, the radial density may vary as a function of the radial position. Alternatively or additionally, the axial density may vary as a function of the radial position.

Multi-Leg Spikes

Figure 6W:
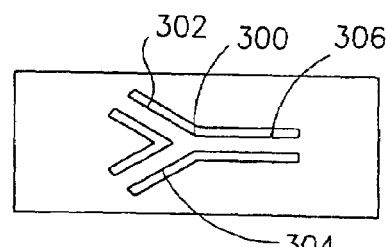
Figure 6X:
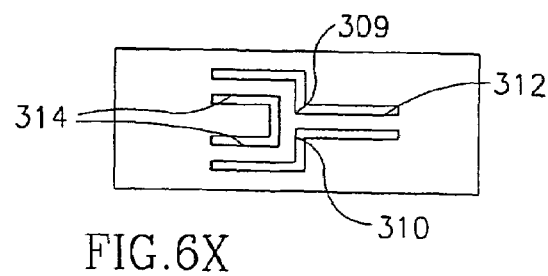
Figure 6X:
Figure 6X:
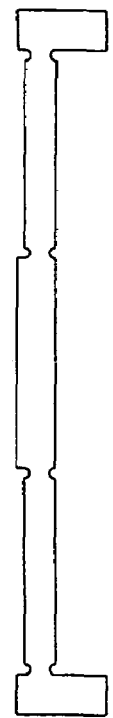
Figure 6X:
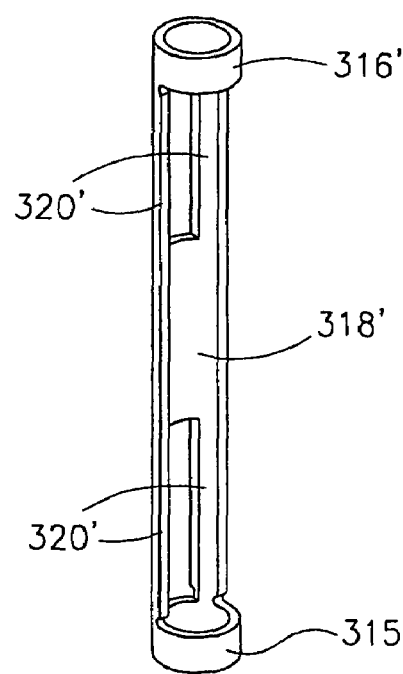
Figure 6X:
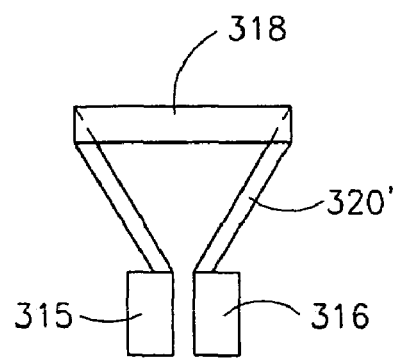
Figure 6X:
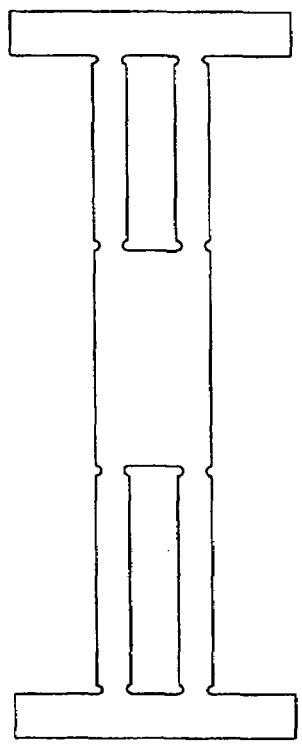

FIGS. 6W and 6X illustrate spikes that have more than two legs. In particular a spike 300 of FIG. 6W has three legs: 302, 304 and 306. In FIG. 6X a spike 308 also has three legs: two legs 314 and one leg 312. A bar 310 connects the two legs 314 to leg 312. It is noted than when spike 308 is extended (perpendicular to the figure), bar 310 twists, rather then bending as in some of the previously described spikes. An additional type of deformation available is a pivot type deformation, in which a joint is defined in the spacer. Possibly, such a joint is defined by using a different material (or differently treated material) for the joint than for the rest of the spacer. These types of deformations (bending, twisting and pivoting) and/or other deformation types may also be used for defining struts and wires. It is noted with respect to FIG. 6X it is noted that the base of spike 308 may have a zero width, for example if leg 312 moves axially to be between legs 314.

Lift-Up spikes

FIGS. 6XA-6XC illustrate a lift-up mechanism, whereby a spike (in this example a flat top spike) is lifted up from the plane of the unexpanded spacer. FIG. 6XA is a side view, FIG. 6XB is a perspective view and FIG. 6XC is a plan layout. Referring to FIG. 6XB and to FIG. 6XG (below), when two ends 315 and 316 of the spacer portion are brought together, legs 320 bend and a portion 318 of the spacer is lifted out of the spacer, in the direction of the arrow. In a preferred embodiment of the invention, the legs 320 are weakened at their ends so that the legs bend only at the weakened areas and/or in a direction dictated by the weakening.

FIGS. 6XD-6XH illustrate an alternative lift-up mechanism, in which a plurality of legs 320' and a lifted up portion 318' are substantially in a same hemisphere of the spacer, so that two symmetrically opposing lift-up spikes may be fabricated on a single spacer segment. FIG. 6XH is a plan layout of the spacer; FIGS. 6XD and 6XE are side views of the collapsed spacer; and FIG. 6XF is a perspective view of the collapsed spacer. FIG. 6XG, which is equally applicable to FIGS. 6XA-6XC illustrates a side view of an expanded spacer, with portion 318 lifted up form the spacer.

One advantage of the lifted up spikes is that they may easily be formed of curved pieces of material, since the lifted up part is not bent.

Another advantage of lift-up spikes is the ability to provide a greater surface contact area (surface fill factor), which contact area can be smooth, rather than spiked.

Selective Weakening

FIGS. 6XIA-6XLB illustrate (using a side view, with an axial portion of the spacer removed) examples of weakening of spacer material to aid in achieving some exemplary spikes profiles of those shown in FIGS. 6A-6K. The weakening illustrated are etching and/or cutting of material in a direction perpendicular to the spacer surface. However, weakening may also be achieved using other means, for example, chemical or metallurgic treatment of by drilling small holes, for example in joints. Addition, the direction of the weakening may be at other orientations, for example along the surface of the spacer (as in FIG. 6XA) or at an angle thereto. Additionally or alternatively, the weakening and/or strengthening of the spacer is applied to provide a preferential distortion direction. FIGS. 6XIA and 6XIB show a weakening pattern which aids in achieving a symmetric spike. FIGS. 6XJA through 6XJD show a weakening pattern which aids in achieving an asymmetric spike. FIGS. 6XKA-6XKC show a weakening pattern which aids in achieving a flat top spike. FIGS. 6XLA and 6XLB show a weakening pattern which aids in achieving an arc shaped spike.

Spike Combinations

Although the above figures illustrate individual spacer geometries, in some preferred embodiments of the invention, geometries from two or more of the above figures may be combined in a single spacer, possibly in a single spike. In addition, the particular spike configuration selected may depend, inter alia, on the intended use of the spacer. In particular, spike combinations and/or configurations may be selected responsive to a desired interaction between spikes, for example adjacent spikes leaning on each other or engaging each other.

Protrusions

Figure 7A:
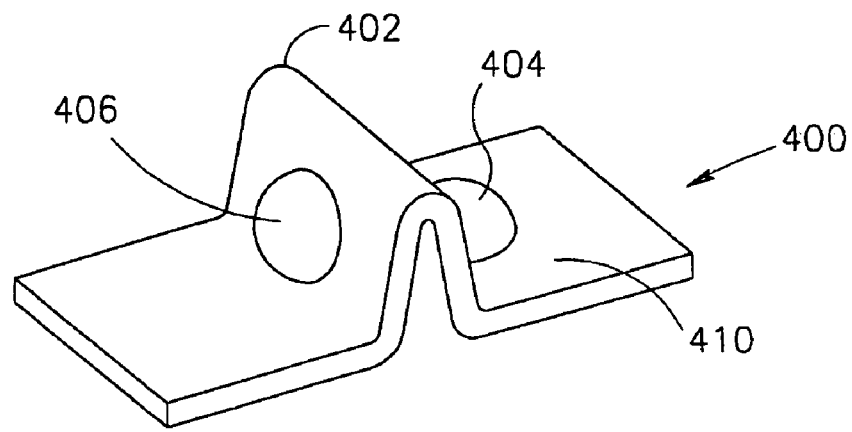
FIGS. 7A and 7B illustrates protrusions on a spacer portion, in accordance with a preferred embodiment of the invention.
Figure 7B:
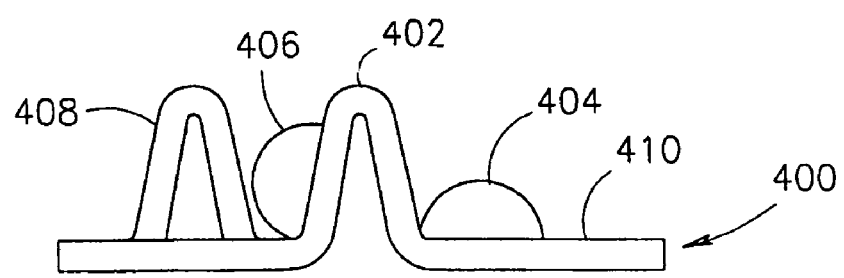

FIGS. 7A and 7B schematically illustrates protrusions on a spacer portion 400, in accordance with a preferred embodiment of the invention. The portion is show in a side view and in a perspective view. Portion 400 includes a spike 402 and a base portion (in some cases a ring segment) 410. In a preferred embodiment of the invention, a protrusion 404 and/or a protrusion 406 are provided to increase the stiffness of spike 402 and/or prevent its collapse under pressure. In the example of protrusion 404, spike 402 cannot fold to the right, because protrusion 404 is blocking the movement In the example of protrusion 406, such movement is again blocked. Protrusion 406 may have an alternative or additional function of stiffening the spacer by filling in gaps between spike 402 and a neighboring (axially and/or radially offset) spike 408.

In a preferred embodiment of the invention, the protrusions are created by a variation in the thickness of the spacer. Alternatively, a protrusion may comprise a portion of the tube which folds out (or in). Preferably, the portion is manufactured to be in an out position and is maintained in an "in" position, while the spacer is collapsed, for example using an external collar. Alternatively, the protrusion may be created by the expansion, for example the protrusion comprising a small spike.

Axial Shrinkage Limitation

Figure 8B:
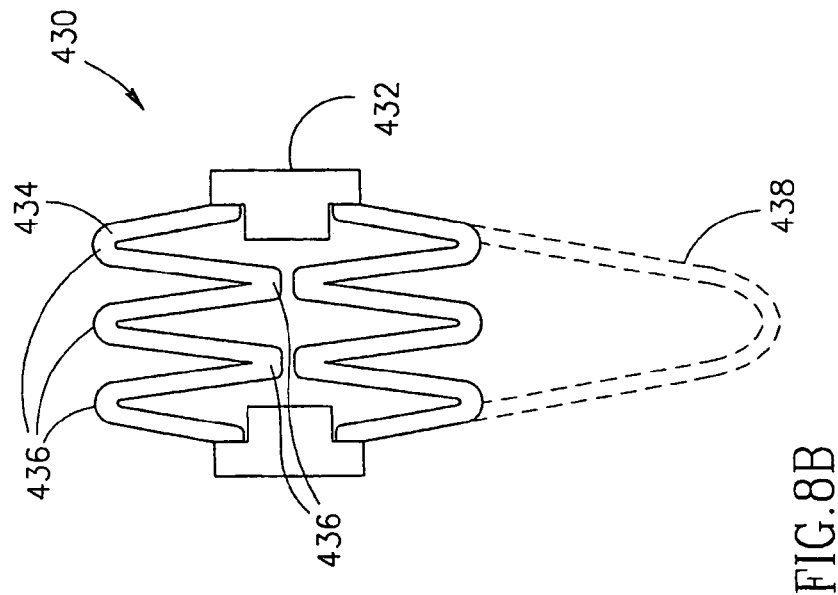
FIGS. 8Ai-8B illustrate spacers for which axial shrinkage of the spacer is limited by the design of a tube portion of the spacer, in accordance with preferred embodiments of the invention.
Figure 8A:
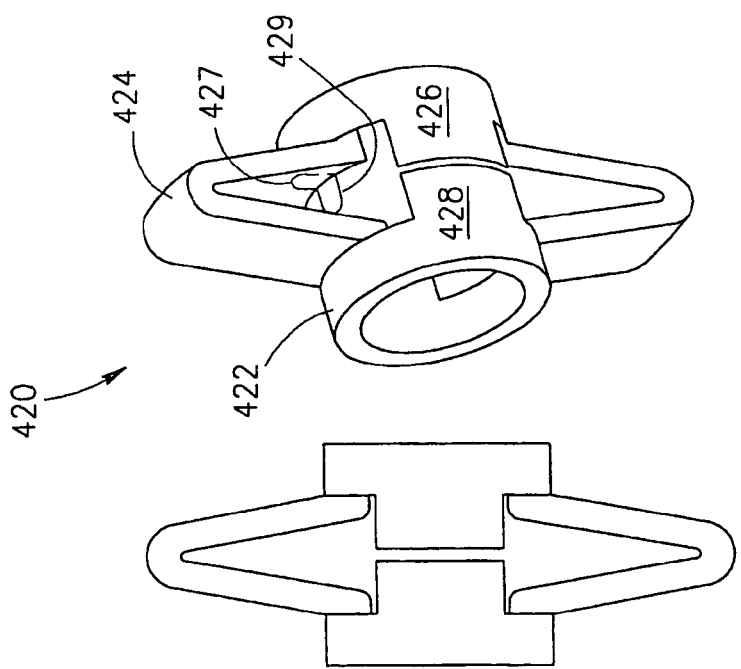

FIGS. 8Ai and 8Aii illustrates a spacer 420 in which axial shrinkage of the spacer is limited by the design of a tube portion 422 of the spacer, in accordance with a preferred embodiment of the invention. when spacer 420 is expanded, tube 422 axially contracts and spike 424 is extended. Additionally tube portions on either side of the spike advance towards each other. These portions are marked as a tab 428 and a tab 426 in the Figure. It is noted however, that only one such tab is required, since the other tube portion may be flush with the spike base or even back therefrom. When the two tabs meet, further axial contraction is impossible or is severely restricted. Further contraction, if it were to occur, would require either that one of the tabs collapse or that one tab travels over the other tab. As noted above with respect to FIG. 6J, such a tab may be useful to guide the extension direction of a spike.

In a preferred embodiment of the invention, an adjustment to mechanical characteristics of a spacer, for example tension, is achieved by moving the one tab relative to the other, for example using an externally applied needle, to allow them to continue their axial movement. Additionally, one such axial motion is allowed, the spacer may be further expanded.

It is noted that the final length and/or shape of the expanded spacer and/or individual spikes thereon may be considerably influenced by tabs 426 and 428. In a preferred embodiment of the invention, a spacer is adapted for a particular use by removing and/or bending such tabs so that they do or do not impede axial compression. In one example, such tabs may be removed in an operating room by a surgeon, after he makes final measurements on an x-ray image. In another example, if a spacer did not fit, the spacer is removed, adjusted and reinserted (or a new, adjusted, spacer is inserted).

In a preferred embodiment of the invention, the distribution of tabs 426 (and 428) is even over the length of the spacer. Alternatively, an uneven axial distribution is provided. Alternatively or additionally, an uneven radial distribution may be provided. Alternatively or additionally, the length of the tabs is different at different parts of the spacer. It is noted that an un-even distribution of tabs on the spacer may cause the expanded spacer to assume a bent configuration and/or for spikes to have un-even lengths.

Alternative Axial Shrinkage Limitation

FIG. 8B illustrates an alternative embodiment of the invention wherein a portion of a spacer 430 collapses upon itself to limit axial contraction of the spacer. In a preferred embodiment of the invention, such collapsing is achieved by weakening a strip of spacer 430 at a plurality of locations, for example those indicated by reference number 436. Preferably, the weakening comprises a thinning of the material on the side of the fold. Alternatively or additionally, the portion is pre-formed to be in a shape of a wave, and maintained in an un-collapsed state either by the un-extended spikes (e.g., before they are plastically deformed) or by a restraining device (for example as described above with reference to FIG. 2). Dotted line 438 indicates an extent of a spike when the spacer is expanded.

In another embodiment of the invention, a spike extends into the lumen of the spacer instead of out, thereby restricting axial contraction of the spacer.

In the embodiments shown in FIGS. 8Ai, 8Aii and 8B, the axial contraction restriction elements appear to be positioned instead of a spike. Although this is possible, it is not required. In alternative embodiments of the invention, at least some of the tabs and/or wave-folded tube portions may be radially located between spikes, for example, a radius including four spikes and four axial contraction restriction elements. Alternatively or additionally, a tab may be defined as part of the spike itself, for example as indicated by dotted lines 427 and 429 in FIG. 8Aii.

Excavating Tool

Figure 9A:
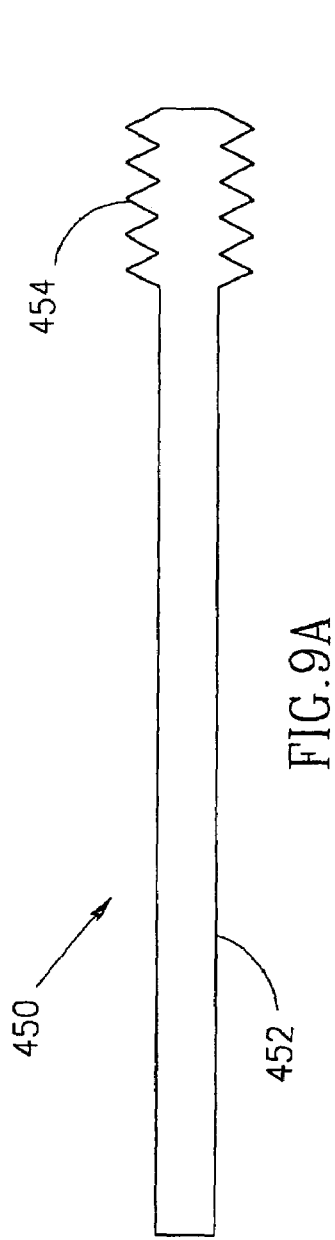
FIG. 9A illustrates an excavating tool, in accordance with a preferred embodiment of the invention.

FIG. 9A illustrates an excavating tool 450, in accordance with a preferred embodiment of the invention. In a preferred embodiment of the invention, tool 450 is used to pulverize a disc, prior to insertion of a spacer. Tool 450 preferably comprises a shaft 452 and a tip 454. In a preferred embodiment of the invention, tip 454 comprises a radially expandable element, as described above with reference to a spacer. Thus, the tool can be inserted in a collapsed diameter and expanded only in the space which is to be excavated. When shaft 452 is rotated, tip 454 rotates and pulverizes the disc material.

In a preferred embodiment of the invention, the entire tool 450 is made of a single material. Alternatively, a material with a different hardness, stiffness and/or abrasion resistance may be used for the tip. Alternatively or additionally, the sides and/or ends of the spikes in tip 454 may be sharpened and/or coated with an abrasive material, to assist in the pulverization.

Figure 9B:
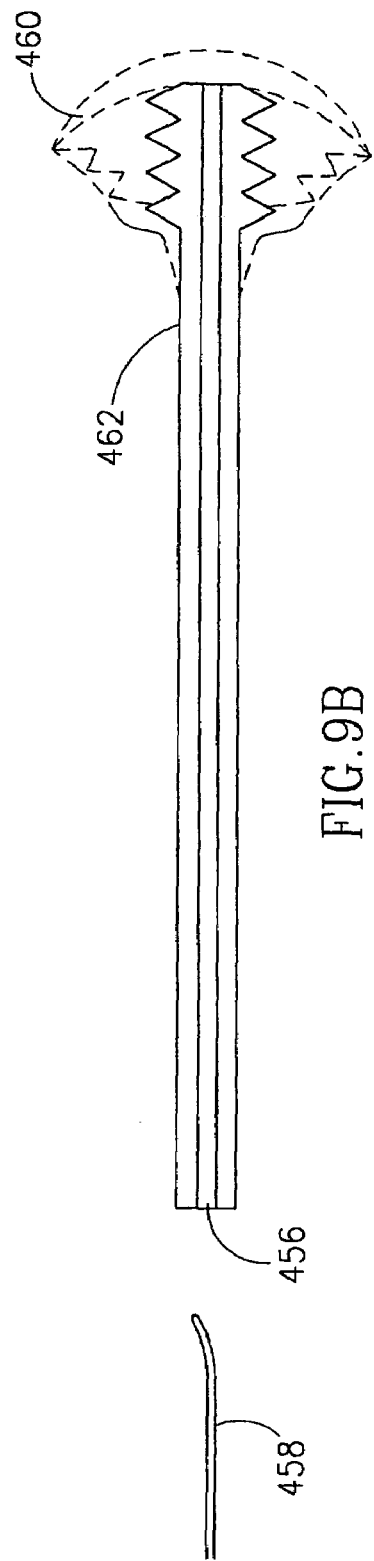
FIG. 9B illustrates the tool of FIG. 9A, in a bent configuration, in accordance with a preferred embodiment of the invention.

FIG. 9B illustrates the tool of FIG. 9A, in which bent configurations are shown using dotted lines, in accordance with a preferred embodiment of the invention. Typically, the geometry of the volume to be excavated does not have a circular cross-section. In a preferred embodiment of the invention, shaft 452 may be bent, at least in a vicinity 462 of tip 454, to allow a greater reach for tip 454. Alternatively or additionally, tip 454 itself may bend. In a preferred embodiment of the invention, the bending is achieved by inserting a bent stylet 458 into a lumen 456 defined in shaft 452. Alternatively, vicinity 462 is flexible and tip 454 is allowed to freely bend.

In a preferred embodiment of the invention, stylet 458 is not rotated with shaft 452, so that tip 454 is maintained in a constant angle, for example maintaining tip 454 in a position 460. Alternatively, the stylet and the shaft are rotated in synchrony.

Alternatively or additionally, tool 454 may be bent by axial contraction thereof. As indicated above, the axial contraction may be uneven on the two sides of the spacer, for by reason of uneven distribution of tabs 426 (FIG. 8Aii). In one example, a regular axial contraction yields a straight tool tip. When the axial contraction is increased (e.g., and more spikes are expanded and/or more tabs abut), the tool bends in one direction, and when the contraction is further increased, the tool bends in another, possibly opposite, direction.

A lumen in tool 450 may have other uses, in some preferred embodiments of the invention. These uses may use the same lumen as lumen 456 or may require a separate lumen. The uses may be applied while the shaft is rotating and/or while the shaft is at rest. One use of such a lumen is to vacuum out the pulverized disc material. Another use is for injecting fluids, for example, pharmaceuticals, tissue softening materials and/or medical imaging contrast materials. Alternatively or additionally, the lumen may be used to provide a cutting action, for example by providing laser light, a knife edge, cryosurgery tools, RF coils or electric cutters through the lumen. Alternatively or additionally, a high pressure flow of abrasive material may be provided. Alternatively or additionally, the lumen may be used to provide endoscopic surgery tools and/or tissue connectors, such as clips or staples. Alternatively or additionally, the lumen may be used to provide an imaging means, such as an optical viewing means or an ultrasonic viewing means. Alternatively or additionally, a spacer may be provided and/or expanded and/or collapsed through the lumen. Optionally, in one preferred embodiment of the invention, the tool itself may be further expanded and used as a spacer, after the disc is removed.

The above uses of a lumen may also be practiced on a spacer, in accordance with some preferred embodiments of the invention. In particular, a tool 450 may be provided through a spacer. In another example, a second spacer may be inserted past a first spacer, by passing a member 60 of the second spacer through the expanded spacer.

Alternative Uses for Spacer Geometry

Figure 10A:
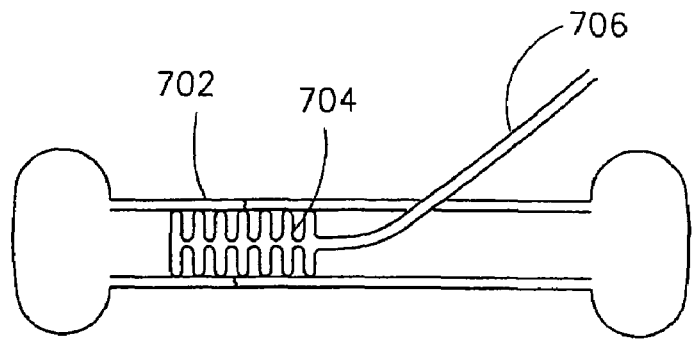
FIGS. 10A-10C illustrate an expandable bone implant, in accordance with a preferred embodiment of the invention.
Figure 10B:
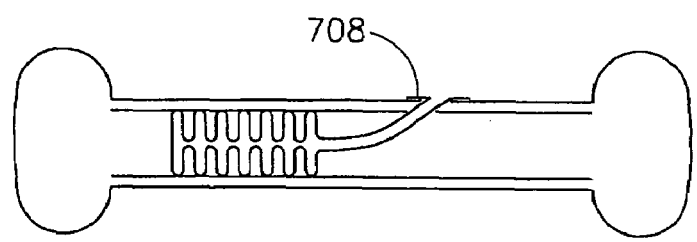
Figure 10C:
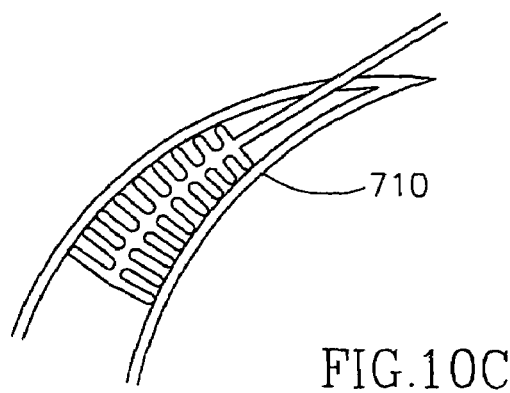

As described above, the expandable spacer is especially suitable for spinal fusion. However, a similar geometry device may have other uses. One type of usage is as a bone fixation device, for example fulfilling the general requirements described in the above referenced PCT publication WO 98/38918. FIG. 10A illustrates a bone 700 with a fracture location 702 into which a spacer 704 (in this example being used as a bone fixator) is being inserted. An optional elongate member 706 may be a guide or may for an extension of the spacer, for example as described herein above with reference to FIG. 2. It is noted that the spacer of the present invention, in some embodiments thereof may be inserted through a small hole in a bone, possibly without open surgery. Optionally, the spacer includes an outside thread, at least at its tip, so that the spacer can be screwed into the bone. Preferably, the spacer may also be removed through the same or a new hole made in the bone, preferably without requiring an open surgical incision. Optionally, as shown in FIG. 10B, when the insertion of the spacer is completed, a flared opening 708 is maintaining in the bone, possibly by an extension of the spacer, to aid in adjusting and/or removing the spacer. Alternatively, it is noted that the spacer does not usually block a large volume of the bone, so it may not be required to remove it. FIG. 10C illustrates the insertion of a spacer into a bent bone 710, for example a rib. Also, it is noted that such a spacer may be inserted into a small bone, for example a finger bone.

Dental Implant

Figure 11:
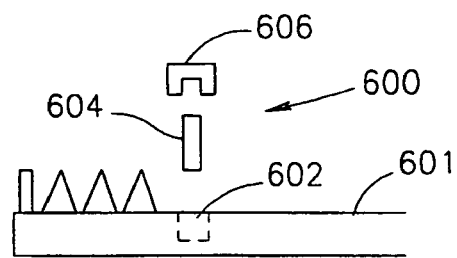
FIG. 11 is an exploded view of a dental implant device in accordance with a preferred embodiment of the invention.

FIG. 11 is an exploded view of a dental implant 600 in accordance with a preferred embodiment of the invention. A tooth is missing in a jaw 601, leaving behind a hole 602. In a preferred embodiment of the invention, an expandable spacer 604 is inserted into the hole and expanded therein, to form a support for a dental cap 606. Preferably, a filler material, such as powdered bone or tooth material is used to fill hole 602. Alternatively or additionally to forming a complete support for a dental cap, an expandable spacer may be used to fill-in a space between a support and the walls of hole 602. Alternatively or additionally, an expandable spacer may be used to replace a single root of a multi-root natural tooth. It is noted that bone tissue, tooth material, nervous tissue and/or blood vessels may grow into the hollows of spacer 604. Optionally, an inner support is also inserted into the spacer, to strengthen it, for example a screw as described above with reference to FIG. 2.

Soft Tissue Connector

Figure 12A:
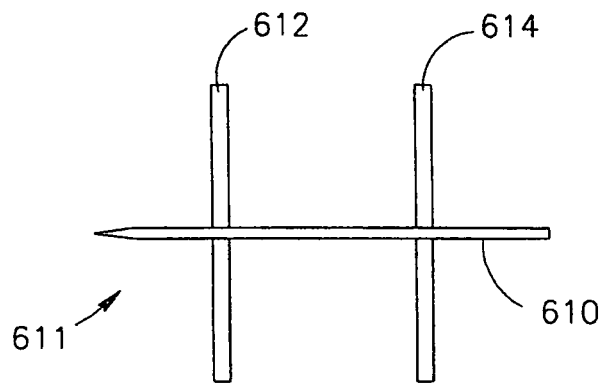
FIGS. 12A-12C illustrate the use of an axially contracting tissue fastener, in accordance with a preferred embodiment of the invention.
Figures 12B, 12C:
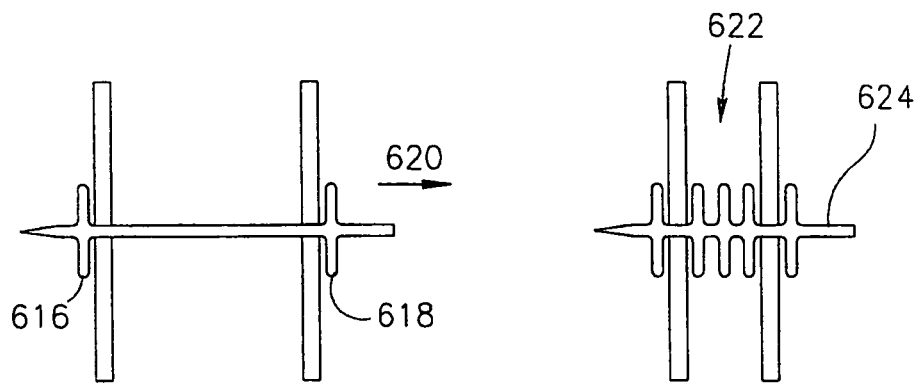

FIGS. 12A-12C illustrate the use of an axially contracting tissue fastener 610, in accordance with a preferred embodiment of the invention. A tissue 612 is to be fastened to tissue 614. A tip 611, preferably sharp, possibly barbed or curved, of fastener 610 preferably penetrates the two tissues, as shown in FIG. 12A. It is noted that fastener 610 may be narrow and/or flexible, thus being suitable for application using a catheter, an endoscope and/or using an external syringe-like device.

In FIG. 12B, a first set of spikes 616 and/or a second set of spikes 618 are preferably extended, to stop the tissues from moving away from each other. In the case that only one set of spikes is extended, for example spikes 616, the fastener may be axially moved, for example in the direction of arrow 620, in order to bring the two tissue together. It should be noted that tissue 612 and/or tissue 614 may have a considerable thickness. In such a case the spikes will preferably expand into the tissue, instead of behind it as shown in FIG. 12B. However, the function of engaging the tissue will preferably be performed.

In FIG. 12C, the rest of fastener 610 is axially contracted, bringing the two tissues in close proximity. The width of an intermediate section 622 of the fastener may depend on the distance between the tissue when spikes 6161 and 618 are expanded and/or it may depend on whether or not the fastener is moved during the procedure. However, in general, the distance between the two tissues will be considerable smaller than in FIG. 12A and the two tissue will be coupled by section 622, preferably to allow little or no relative motion. Optionally, the fastener (or a spacer, as described above) is formed of a plurality of links which can rotate one relative to the other. Thus, the two attached soft tissue can rotate one relative to each other, if each is grasped by a different link of the spacer. In a preferred embodiment of the invention, each such link may be expanded or collapsed separately.

As described above, the spikes of fastener 610 are preferably expanded in a certain order. However, the action of FIGS. 12A-C will occur also if all the spikes are expanded at the same time. Generally, after a short axial contraction, spikes 616 will expand enough so that they will not retract through the hole made in tissue 612 by tip 611. Although further axial contraction will increase the tension on the hole (by stretching/moving tissue 612) it will also increase the spike size, so retraction of the spikes is unlikely.

In a preferred embodiment of the invention, exact placement of fastener 610 is not required, since once tissues 612 and 614 are skewered by fastener 610 and are each located between two spike positions, further axial contraction of the fastener will invariably engage the tissues and bring them together.

In some preferred embodiments of the invention, the spikes in section 622 are longer than in the rest of fastener 610, allowing a greater axial contraction. It is noted that, in some applications, it is desirable to allow some "free" space between the fastened soft tissues.

In a preferred embodiment of the invention, once the process of FIGS. 12A-12C is complete, fastener 610 is disengaged at its end 624 from a member (not shown) which was holding it in place. Alternatively, fastener 610 comprises an elastic or super elastic element which is injected into a tissue and allowed to self-expand, without being held by a member. Alternatively fastener 610 may comprise a portion of a continuously extruded fastener. When required to fasten soft tissue, a short segment of the fastener is used as in FIGS. 12A-12C and then the remainder of the fastener is cut off. Thus, multiple fastening activities may be performed with a minimum required diameter and a minimum of tool exchanging and/or toll motion.

As an alternative embodiment (not shown) a single spike may span spikes 616 and 618. Referring back to FIG. 2K (multi-sub-spike spike example) a single spike may include two or more sub spikes, for example a sub-spike 616 and a sub-spike 618. When such a single spike partially extends, the two sub spikes engage the soft tissues. As the spike continues to extend (axial compression of the fastener) each of the sub spikes increases in radial extent and is brought closer together. Such behavior may be controlled by suitable weakening of the spikes, as described above, for example with reference to FIGS. 6XIA and 6XIB, noting however, that if a spike is weakened by different amounts in different locations, the weaker location will typically fold first and then the strongest location, when axial compression is applied.

Alternatively to fastening soft tissue to soft tissue, a fastener similar to fastener 610 may be used for attaching soft tissue to bone. In one example, if tip 611 comprises a bone anchor, the process of FIGS. 12A-C may be performed to attach tissue 614 to a bone 612, except that there is generally no need to expand spikes 616 in the bone. Alternatively, spikes 616 are expanded a small amount, to better hold the bone. Alternatively, spikes 616 are expanded by a large amount, for example if tip 611 passes through a cortical portion of the bone into a trabecular portion thereof.

Additionally or alternatively, to fastening soft tissue to bone, a similar fastener may be used to attach a bone to a bone and/or to apply attractive forces between two bones. In this embodiment, it may be unnecessary for the spikes to extend when the spacer is axially shortened. In a preferred embodiment of the invention, a spike shape as shown in FIG. 6K is used, in which the spikes extend a minimal amount. Alternatively, the spikes may "extend" into the lumen, preferably using a spike profile which is the inverse of that of FIG. 6K.

Space Filling Using a Spacer

Another possibly use of the expanding spacer is to fill intra body cavities and/or change mechanical properties of body tissues, for example stiffness, elasticity, minimum compressed dimension. For example, such a spacer may be used to stiffen a intra-vertebral disc. Additionally or alternatively, such a spacer is used as a framework for new tissue growth.

Additionally or alternatively, such a spacer is used to enhance drainage. Changing the mechanical properties of body tissue may also be used for cosmetic purposes, for example to reduce sagging and to disguise flabby flesh.

In some such cases, the spacer is composed, at least in part, of softer, thinner and/or more flexible materials than described with reference to FIGS. 4A-4C. In one example, the spacer is made of plastic. In another example, the spacer comprises polymer coated metal.

Another possible use of such a spacer is for opening crushed or otherwise blocked air passageways. One advantage of some embodiments of the above spacer is that they are inherently non-blocking, if for example a spacer fails to open properly.

External Control of Spacer Geometry

In a preferred embodiment of the invention, a spacer, for example as described above, can be controlled from outside the body, after it is inserted. In one example, referring back to FIG. 2J, screw 124 may be turned by coupling a magnetic force from outside the body, for example if a small permanent magnet is coupled to the screw. When a strong permanent magnet is rotated outside the body, torque is applied to the small magnet, turning the screw. In another example, externally applied magnetic and/or electric fields may be used to control a pressure valve, which valve allows pressurized fluid to inflate or deflate a balloon, thereby axially and/or radially expanding or collapsing the spacer. In some embodiments, the control of spacer expansion uses logic (electrical or mechanical) which is integrated into the spacer, for example, to periodically axially compress the spacer. The power and/or control signals may be supplied from inside the body or from a power source (or computer) outside the body.

It will be appreciated that the above described apparatus and methods of expandable inserts may be varied in many ways. In addition, a multiplicity of various features, both of methods and of devices have been described. It should be appreciated that different features may be combined in different ways. In particular, not all the features shown above in a particular embodiment are necessary in every similar preferred embodiment of the invention. Further, combinations of the above features are also considered to be within the scope of some preferred embodiments of the invention. It should also be appreciated that many of the embodiments are described only as methods or only as apparatus, however the scope of the invention includes both methods for using apparatus and apparatus for applying the methods. The scope of the invention also covers machines for creating the apparatus described herein. In addition, the scope of the invention includes methods of using, constructing, calibrating and/or maintaining the apparatus described herein. Section headings where they appear are meant for clarity and ease of browsing the application and are not to be construed as limiting the applicability of subject matter described within. When used in the following claims or in the text above, the terms "comprises", "comprising", "includes", "including" or the like mean "including but not limited to".

The invention claimed is:

1. An expandable spacer, comprising:
an axial tube having a surface provided along an initial contour, a proximal end, a distal end and a length,
wherein, said surface defines a plurality of axially displaced slits, said plurality of slits defining at least two axially displaced extensions, such that when said tube is axially compressed, said extensions extend out of said initial contour and define a geometry of an expanded spacer;
wherein when the tube is axially compressed, the at least two extensions have respective peaks farthest radially from the tube, the peaks of the extensions being separated from each other along the tube axis by portions of said surface situated radially inwards of said peaks in the axially compressed configuration;
wherein said spacer is adapted for support of two vertebral plates on either side of the spacer, and
wherein at least one of the extensions is designed to carry greater stress and has an increased strength over another extension, wherein a trans-axial cross-section diameter of said expanded geometry varies along an axis of said expanded geometry; and
wherein said cross-section is rectangular and wherein said cross-section diameter increases along said expanded geometry axis.

2. An expandable spacer, comprising:
an axial tube having a surface provided along an initial contour, a proximal end, a distal end and a length,
wherein, said surface defines a plurality of axially displaced slits, said plurality of slits defining at least two axially displaced extensions, such that when said tube is axially compressed, said extensions extend out of said initial contour and define a geometry of an expanded spacer;
wherein when the tube is axially compressed, the at least two extensions have respective peaks farthest radially from the tube, the peaks of the extensions being separated from each other along the tube axis by portions of said surface situated radially inwards of said peaks in the axially compressed configuration;
wherein said spacer is adapted for support of two vertebral plates on either side of the spacer, and
wherein at least one of the extensions is designed to carry greater stress and has an increased strength over another extension, said spacer further comprising a ratchet mechanism to maintain said spacer in an expanded configuration.

3. An expandable spacer, comprising:
an axial tube having a surface provided along an initial contour, a proximal end, a distal end and a length,
wherein, said surface defines a plurality of axially displaced slits, said plurality of slits defining at least two axially displaced extensions, such that when said tube is axially compressed, said extensions extend out of said initial contour and define a geometry of an expanded spacer;
wherein when the tube is axially compressed, the at least two extensions have respective peaks farthest radially from the tube, the peaks of the extensions being separated from each other along the tube axis by portions of said surface situated radially inwards of said peaks in the axially compressed configuration;
wherein said spacer is adapted for support of two vertebral plates on either side of the spacer, and
wherein at least one of the extensions is designed to carry greater stress and has an increased strength over another extension, said spacer further comprising at least one portion of said spacer that prevents axial contraction of said spacer, wherein said at least one portion comprises a strip that folds and forms a thickness between two opposing sides of said spacer, preventing the opposing sides from meeting.

4. An expandable spacer, comprising:
an axial tube having a surface provided along an initial contour, a proximal end, a distal end and a length,
wherein, said surface defines a plurality of axially displaced slits, said plurality of slits defining at least two axially displaced extensions, such that when said tube is axially compressed, said extensions extend out of said initial contour and define a geometry of an expanded spacer;
wherein when the tube is axially compressed, the at least two extensions have respective peaks farthest radially from the tube, the peaks of the extensions being separated from each other along the tube axis by portions of said surface situated radially inwards of said peaks in the axially compressed configuration;
wherein said spacer is adapted for support of two vertebral plates on either side of the spacer, and
wherein at least one of the extensions is designed to carry greater stress and has an increased strength over another extension, wherein said spacer is formed of a combination of distinct zones of different materials.

5. An expandable spacer, comprising:
an axial tube having a surface provided along an initial contour, a proximal end, a distal end and a length,
wherein, said surface defines a plurality of axially displaced slits, said plurality of slits defining at least two axially displaced extensions, such that when said tube is axially compressed, said extensions extend out of said initial contour and define a geometry of an expanded spacer;
wherein when the tube is axially compressed, the at least two extensions have respective peaks farthest radially from the tube, the peaks of the extensions being separated from each other along the tube axis by portions of said surface situated radially inwards of said peaks in the axially compressed configuration;
wherein said spacer is adapted for support of two vertebral plates on either side of the spacer, and
wherein at least one of the extensions is designed to carry greater stress and has an increased strength over another extension, wherein said spacer is formed of a super-elastic material, which is super-elastically deformed by an extension deformation.

6. An expandable spacer, comprising:
an axial tube having a surface provided along an initial contour, a proximal end, a distal end and a length,
wherein, said surface defines a plurality of axially displaced slits, said plurality of slits defining at least two axially displaced extensions, such that when said tube is axially compressed, said extensions extend out of said initial contour and define a geometry of an expanded spacer;
wherein when the tube is axially compressed, the at least two extensions have respective peaks farthest radially from the tube, the peaks of the extensions being separated from each other along the tube axis by portions of said surface situated radially inwards of said peaks in the axially compressed configuration;

wherein said spacer is adapted for support of two vertebral plates on either side of the spacer, and wherein at least one of the extensions is designed to carry greater stress and has an increased strength over another extension, wherein said spacer is adapted to axially deform only under axial forces of over 20 Kg force.

7. An expandable spacer, comprising:

an axial tube having a surface provided along an initial contour, a proximal end, a distal end and a length, wherein, said surface defines a plurality of axially displaced slits, said plurality of slits defining at least two axially displaced extensions, such that when said tube is axially compressed, said extensions extend out of said initial contour and define a geometry of an expanded spacer;

wherein when the tube is axially compressed, the at least two extensions have respective peaks farthest radially from the tube, the peaks of the extensions being separated from each other along the tube axis by portions of said surface situated radially inwards of said peaks in the axially compressed configuration;

wherein said spacer is adapted for support of two vertebral plates on either side of the spacer, and wherein at least one of the extensions is designed to carry greater stress and has an increased strength over another extension, wherein said spacer is adapted to axially deform only under axial forces of over 30 Kg force.

8. An expandable spacer, comprising:

an axial tube having a surface provided along an initial contour, a proximal end, a distal end and a length, wherein, said surface defines a plurality of axially displaced slits, said plurality of slits defining at least two axially displaced extensions, such that when said tube is axially compressed, said extensions extend out of said initial contour and define a geometry of an expanded spacer;

wherein when the tube is axially compressed, the at least two extensions have respective peaks farthest radially from the tube, the peaks of the extensions being separated from each other along the tube axis by portions of said surface situated radially inwards of said peaks in the axially compressed configuration;

wherein said spacer is adapted for support of two vertebral plates on either side of the spacer, and wherein at least one of the extensions is designed to carry greater stress and has an increased strength over another extension, wherein said spacer is adapted to axially deform only under axial forces of over 50 Kg force.

9. An expandable spacer, comprising:

an axial tube having a surface provided along an initial contour, a proximal end, a distal end and a length, wherein, said surface defines a plurality of axially displaced slits, said plurality of slits defining at least two axially displaced extensions, such that when said tube is axially compressed, said extensions extend out of said initial contour and define a geometry of an expanded spacer;

wherein when the tube is axially compressed, the at least two extensions have respective peaks farthest radially from the tube, the peaks of the extensions being separated from each other along the tube axis by portions of said surface situated radially inwards of said peaks in the axially compressed configuration;

wherein said spacer is adapted for support of two vertebral plates on either side of the spacer, and wherein at least one of the extensions is designed to carry greater stress and has an increased strength over another extension, wherein said spacer is adapted to axially deform only under axial forces of over 70 Kg force.

10. An expandable spacer, comprising:

an axial tube having a surface provided along an initial contour, a proximal end, a distal end and a length, wherein, said surface defines a plurality of axially displaced slits, said plurality of slits defining at least two axially displaced extensions, such that when said tube is axially compressed, said extensions extend out of said initial contour and define a geometry of an expanded spacer;

wherein when the tube is axially compressed, the at least two extensions have respective peaks farthest radially from the tube, the peaks of the extensions being separated from each other along the tube axis by portions of said surface situated radially inwards of said peaks in the axially compressed configuration;

wherein said spacer is adapted for support of two vertebral plates on either side of the spacer, and wherein at least one of the extensions is designed to carry greater stress and has an increased strength over another extension, wherein said spacer is adapted to axially deform only under axial forces of over 90 Kg force.

11. An expandable spacer, comprising:

an axial tube having a surface provided along an initial contour, a proximal end, a distal end and a length, wherein, said surface defines a plurality of axially displaced slits, said plurality of slits defining at least two extensions, such that when said tube is axially compressed, said extensions extend out of said initial contour and define a geometry of an expanded spacer;

wherein when the tube is axially compressed, the at least two extensions have respective peaks farthest radially from the tube, the peaks of the extensions being separated from each other along the tube axis by portions of said surface situated radially inwards of said peaks in the axially compressed configuration;

wherein said spacer is adapted for support of two vertebral plates on either side of the spacer, and wherein said spacer comprises at least one portion that prevents axial contraction of said spacer, the at least one portion including a pair of tabs that abut when the spacer is axially contracted or a strip that folds and forms a thickness between two opposing sides of said spacer, preventing the opposing sides from meeting.

12. A spacer according to claim 11, wherein said at least two extensions comprises at least three extensions, which three extensions extend in at least three different directions from said tube.

13. A spacer according to claim 11, wherein said at least two extensions comprises at least four extensions, which four extensions extend in at least four different directions from said tube.

14. A spacer according to claim 11, wherein said slits are straight.

15. A spacer according to claim 11, wherein said slits are curved.

16. A spacer according to claim 11, wherein said slits are narrow.

17. A spacer according to claim 11, wherein said slits are substantially parallel to said tube axis.

18. A spacer according to claim 11, wherein said slits are not parallel to said tube axis.

19. A spacer according to claim 11, wherein said slits are arranged in pairs of same length.

20. A spacer according to claim 11, wherein slits associated with one extension axially overlap slits associated with a second, axially displaced, extension.

21. A spacer according to claim 11, wherein said proximal end of said tube defines a proximal end-cap, which end-cap extends outside of a volume defined by the geometry of said extended extensions.

22. A spacer according to claim 11, wherein said distal end of said tube defines a distal end-cap, which end-cap extends outside of a volume defined by the geometry of said extended extensions.

23. A spacer according to claim 21, wherein at least one of said extensions is flush with said proximal end of said tube.

24. A spacer according to claim 21, wherein at least one of said extensions is flush with said distal end of said tube.

25. A spacer according to claim 11, further comprising at least one spur axially extending from said spacer, to engage tissue adjacent said spacer.

26. A spacer according to claim 25, wherein said at least one spur comprises at least two spurs axially extending from said spacer.

27. A spacer according to claim 11, further comprising an inner bolt.

28. A spacer according to claim 27, wherein said inner bolt has a smooth exterior.

29. A spacer according to claim 27, wherein said inner bolt has a threaded exterior.

30. A spacer according to claim 27, wherein said bolt has a head, which head locks against at least one end of said tube, to prevent axial expansion of said tube, wherein said head comprises at least one protrusion extending from said head toward said tube, to engage said tube.

31. A spacer according to claim 11, wherein at least one of the extensions is designed to carry greater stress and has an increased strength over another extension, wherein said spacer comprises a plurality of segments, each segment defining one or more extensions that extend from said spacer; and
wherein said segments comprises at least two segment types, each segment type defining extensions that extend in different directions relative to said tube, wherein said two segment types comprise a horizontal segment defining two extensions that extend along a line and a segment defining four extensions that extend at about ±45° to said two extensions.

32. A spacer according to claim 11, wherein a trans-axial cross-section diameter of said expanded geometry varies along an axis of said expanded geometry; and
wherein said cross-section is rectangular and wherein said cross-section diameter increases along said expanded geometry axis.

33. A spacer according to claim 11, wherein said spacer further comprising a ratchet mechanism to maintain said spacer in an expanded configuration.

34. A spacer according to claim 11, wherein said spacer further comprising at least one protrusion on at least one of said extensions, to prevent collapsing of said extension.

35. A spacer according to claim 11, wherein the at least one portion includes at least one pair of tabs that prevent axial contraction.

36. A spacer according to claim 11, wherein said spacer is adapted to axially deform only under axial forces of over 20 Kg force.

37. A spacer according to claim 11, wherein said spacer is adapted to axially deform only under axial forces of over 30 Kg force.

38. A spacer according to claim 11, wherein said spacer is adapted to axially deform only under axial forces of over 50 Kg force.

39. A spacer according to claim 11, wherein said spacer is adapted to axially deform only under axial forces of over 70 Kg force.

40. A spacer according to claim 11, wherein said spacer is adapted to axially deform only under axial forces of over 90 Kg force.

41. A spacer according to claim 11, wherein said spacer is adapted to remain expanded in a vertebra of an active human, when placed with the tube axis perpendicular to a spine of said human.

42. A spacer according to claim 11, wherein said spacer is coated with a bio-active coating.

43. A spacer according to claim 42, wherein said bio-active coating retards bone ingrowth.

44. A spacer according to claim 42, wherein said bio-active coating promotes bone ingrowth.

45. A spacer according to claim 11, wherein said spacer comprises at least one protrusion on at least one of said extensions, to prevent collapsing of said extension.

46. A spacer according to claim 11, wherein said spacer is formed of a super-elastic material, which is super-elastically deformed by an extension deformation.

47. A spacer according to claim 11, wherein said spacer is formed of a combination of distinct zones of different materials.

48. A spacer according to claim 11, wherein a plurality of annealed locations are provided on said spacer to assist in expansion of said spacer.

49. A spacer according to claim 11, wherein at least one of said extensions comprises at least four legs that are coupled by an extension top.

50. A spacer according to claim 11, said spacer further comprising at least one protrusion on at least one of said extensions, to interlock said at least two extensions.

51. A spacer according to 11, wherein said slits are arranged in pairs of different lengths.

* * * * *